(12) United States Patent
Yushin et al.

(10) Patent No.: US 9,994,715 B2
(45) Date of Patent: Jun. 12, 2018

(54) FORMATION AND MODIFICATIONS OF CERAMIC NANOWIRES AND THEIR USE IN FUNCTIONAL MATERIALS

(71) Applicants: Sila Nanotechnologies Inc., Alameda, CA (US); GEORGIA TECH RESEARCH CORPORATION, Atlanta, GA (US)

(72) Inventors: Gleb Yushin, Atlanta, GA (US); James Benson, Atlanta, GA (US); Danni Lei, Atlanta, GA (US); Eugene Berdichevsky, Oakland, CA (US)

(73) Assignees: Sila Nanotechnologies Inc., Alameda, CA (US); Georgia Tech Research Corporation, Atlanta, GA (US)

( * ) Notice: Subject to any disclaimer, the term of this patent is extended or adjusted under 35 U.S.C. 154(b) by 0 days. days.

(21) Appl. No.: 15/395,930

(22) Filed: Dec. 30, 2016

(65) Prior Publication Data

US 2017/0233579 A1    Aug. 17, 2017

Related U.S. Application Data

(60) Provisional application No. 62/295,989, filed on Feb. 16, 2016, provisional application No. 62/307,864, filed on Mar. 14, 2016.

(51) Int. Cl.
    *B05D 7/00*      (2006.01)
    *C09C 1/40*      (2006.01)
    (Continued)

(52) U.S. Cl.
    CPC ............... *C09C 1/407* (2013.01); *C01F 7/30* (2013.01); *C07F 5/069* (2013.01); *C09D 1/00* (2013.01);
    (Continued)

(58) Field of Classification Search
    CPC ................................. C09C 1/407; C01F 7/30
    (Continued)

(56) References Cited

U.S. PATENT DOCUMENTS

| | | | |
|---|---|---|---|
| 6,444,862 B1 * | 9/2002 | Burkhardt | C07C 29/70 568/851 |
| 7,311,754 B2 * | 12/2007 | Virkar | B22F 1/0018 75/370 |
| 8,110,510 B1 | 7/2012 | Fanfair et al. | |

OTHER PUBLICATIONS

Yoo et al., "Synthesis of aluminum isopropoxide from aluminum dross," Korean Journal of Chemical Engineering, vol. 23, No. 4, pp. 683-687, Jul. 1, 2006.

(Continued)

*Primary Examiner* — Tabatha Penny
(74) *Attorney, Agent, or Firm* — Steven Driskill

(57) ABSTRACT

A catalyst-free synthesis method for the formation of a metalorganic compound comprising a desired (first) metal may include, for example, selecting another (second) metal and an organic solvent, with the second metal being selected to (i) be more reactive with respect to the organic solvent than the first metal and (ii) form, upon exposure of the second metal to the organic solvent, a reaction by-product that is more soluble in the organic solvent than the metalorganic compound. An alloy comprising the first metal and the second metal may be first produced (e.g., formed or otherwise obtained) and then treated with the organic solvent in a liquid phase or a vapor phase to form a mixture comprising (i) the reaction by-product comprising the second metal and (ii) the metalorganic compound comprising the first metal. The metalorganic compound may then be separated from the mixture in the form of a solid.

24 Claims, 28 Drawing Sheets

(51) Int. Cl.
    *C01F 7/30*         (2006.01)
    *C07F 5/06*         (2006.01)
    *C09D 1/00*         (2006.01)
    *C23C 16/455*       (2006.01)

(52) U.S. Cl.
    CPC .... *C23C 16/45525* (2013.01); *C01P 2004/16* (2013.01)

(58) Field of Classification Search
    USPC .......................................................... 427/212
    See application file for complete search history.

(56) References Cited

OTHER PUBLICATIONS

Li et al., "Oxide-metal nanowires by oxidation of a one-dimensional Mn-Pd Alloy, Stability and Reactivity," Langmuir, vol. 26, No. 21, pp. 16474-16480, Jun. 8, 2010.
Lei et al., "Transformation of bulk alloys to oxide nanowires," Science, vol. 355, pp. 267-271, Jan. 20, 2017.
International Search Report and Written Opinion dated Mar. 30, 2017 in International Application No. PCT/US2017/012042.

\* cited by examiner

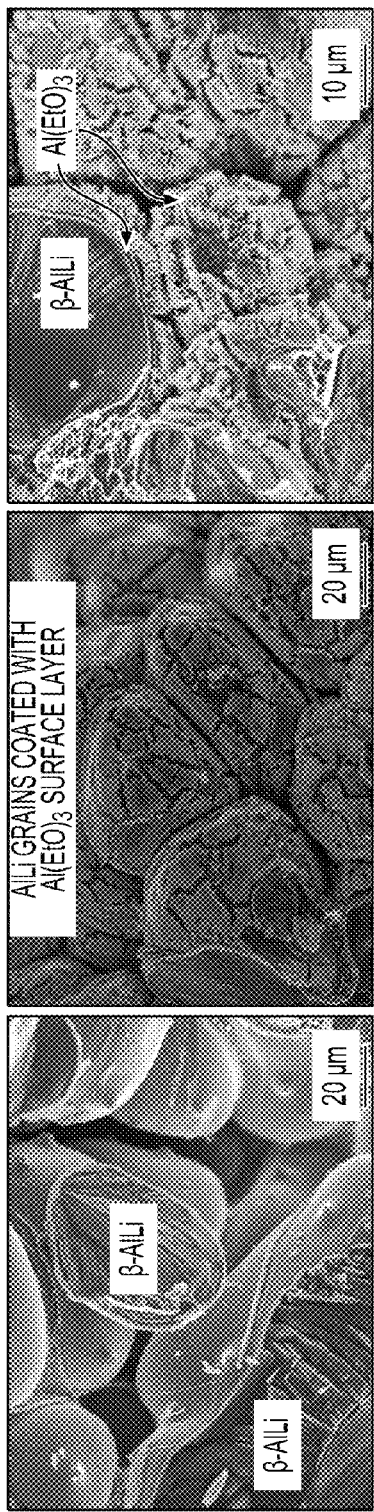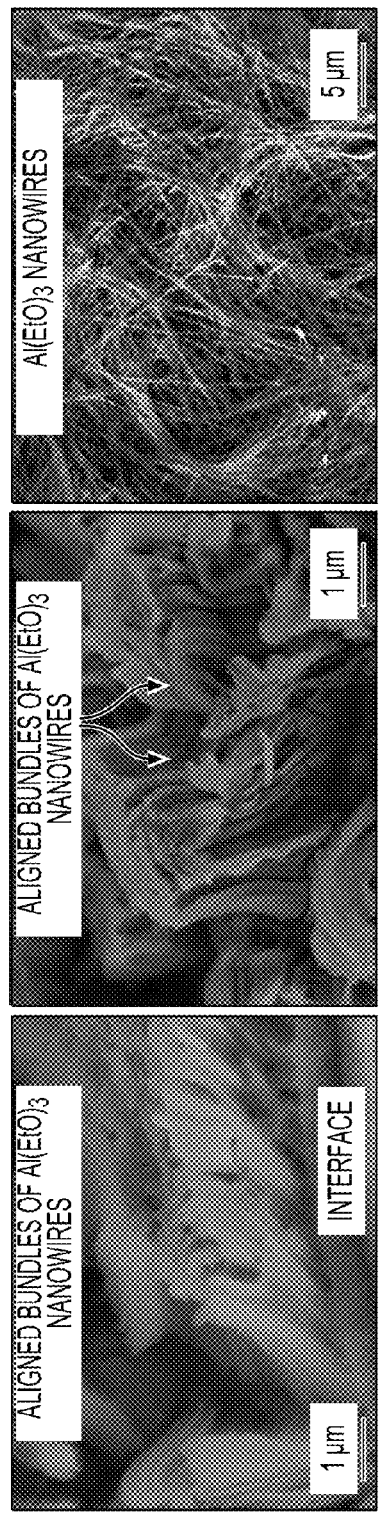

FORMATION AND MODIFICATIONS OF CERAMIC NANOWIRES AND THEIR USE IN FUNCTIONAL MATERIALS

CLAIM OF PRIORITY UNDER 35 U.S.C. § 119

The present application for patent claims the benefit of U.S. Provisional Application No. 62/307,864, entitled "Formation and Modifications of Ceramic Nanowires and their use in Functional Materials," filed Mar. 14, 2016, and U.S. Provisional Application No. 62/295,989, entitled "Low Cost, Aluminum Oxide Nanowires for a Safer, Higher Power, and Energy Dense All-Ceramic Li-Ion Battery Separator," filed Feb. 16, 2016, each of which is expressly incorporated herein by reference in its entirety.

BACKGROUND

Field

The present disclosure relates generally to the synthesis and fabrication of nanomaterials and nanocomposites, and more particularly to the synthesis of nanowires, whiskers, elongated nanomaterials, porous elongated nanomaterials, and the like, and their use in polymer, ceramic, glass, and metal composites, as well as in catalysts, energy storage devices, membranes/separators, filters, optical devices, and other applications.

Background

Owing in part to their relatively light weight, high surface area, and good mechanical properties, elongated ceramic materials with a diameter less than around 10 microns down to a few nanometers, a length from around 10 nm to around 1 mm, an aspect ratio from around 4 to around 20,000, and specific surface area in the range from around 2 to around 3,000 $m^2/g$ may be utilized in a broad range of composites and nanocomposites for enhancement of various mechanical properties, optical properties, thermal stabilities, and other properties. The production of such materials, often called ceramic nanowires, nanofibers, or whiskers (depending on their dimensions and morphology), with controlled dimensions and at a low cost would be desirable for a wide range of composite applications as reinforcement. Thermally stable nanowires and whiskers may be particularly attractive in high temperature applications. In contrast to carbon nanotubes and carbon (nano)fibers (other types of elongated nanomaterials made primarily of carbon atoms), ceramic nanowires may offer improved dispersion, optical transparency, stability against oxidation at elevated temperatures, electrical insulation, more easily modifiable surfaces, and other properties, which make them attractive for various applications.

However, despite the useful properties and the commercial potential of ceramic nanowires, nanofibers, and whiskers, their applications have been rather limited due to the high cost of the conventionally-employed synthesis techniques (such as chemical vapor deposition, hydrothermal synthesis, and others) and the limited experimental ability to tune their characteristic dimensions, surface morphology, and other properties.

Accordingly, there remains a need for improved methods for synthesis of ceramic nanowires, nanofibers, whiskers, and other related materials, as well as their modification and use in composites. There additionally remains a need for improved materials and improved manufacturing processes.

SUMMARY

Embodiments disclosed herein address the above stated needs by providing improved methods of synthesis of nanowires, whiskers, elongated nanomaterials, porous elongated nanomaterials, and the like.

Embodiments disclosed herein also address various applications of nanowires, whiskers, elongated nanomaterials, porous elongated nanomaterials, and the like, including those for improved battery components, improved batteries made therefrom, and methods of making and using the same.

As an example, a catalyst-free synthesis method is provided for the formation of a metalorganic compound comprising a desired (first) metal. The method may include, for example, selecting another (second) metal and an organic solvent, with the second metal being selected to (i) be more reactive with respect to the organic solvent than the first metal and (ii) form, upon exposure of the second metal to the organic solvent, a reaction by-product comprising the second metal that is more soluble in the organic solvent than the metalorganic compound comprising the first metal. An alloy comprising the first metal and the second metal may be first produced (e.g., formed or otherwise obtained) and then treated with the organic solvent in a liquid phase or a vapor phase to form a mixture comprising (i) the reaction by-product comprising the second metal and (ii) the metalorganic compound comprising the first metal. The metalorganic compound may then be separated from the mixture in the form of a solid, as described in more detail below.

In some designs, the second metal may have a reactivity with respect to the organic solvent that is at least five times higher than that of the first metal. Example elements for the first metal include Ti, Cr, Fe, Co, Ni, Cu, Zr, Nb, Mo, Ru, Rh, Pd, Ag, Ta, W, Re, Os, Ir, Pt, Al, Zn, Cd, In, Sn, Sb, Bi, P, La, Ce, Ca, Mg, Sr, and Be. Example elements for the second metal include Li, K, Ca, and Na.

When the organic solvent is in the form of a liquid, the treating may be performed at a temperature in the range of about −20° C. to about +200° C., for example.

In some designs, the metalorganic compound may comprise porous particles. In addition or as an alternative, the metalorganic compound may comprise elongated particles. The elongated particles may exhibit, for example, a width in the range of about 2 nm to about 10 microns, a length in the range of about 50 nm to about 50 mm, and a corresponding width-to-length aspect ratio in the range of about 1:4 to about 1:10,000,000. 9. Example metalorganic compounds include various alkoxides.

For some applications, the method may further comprise converting the metalorganic compound to a metal oxide compound in the form of elongated particles. The elongated metal oxide particles may be porous. The converting may be performed at a temperature in the range of about −20° C. to about +1500° C. in an oxygen-containing environment.

In some designs, a coating layer may be deposited on a surface of the elongated metal oxide particles or a precursor thereof. The coating layer may be a metal, a polymer, or a ceramic material, for example. The coating layer may be deposited via chemical vapor deposition or atomic vapor deposition.

For some applications, elongated particles of the metalorganic compound may be formed into a membrane or body and converted into elongated metal oxide compound particles to form a porous oxide membrane or body. The converting may partially bond at least some of the elongated metal oxide compound particles to each other. For some applications, the porous oxide membrane or body may be infiltrated with a filler material (e.g., a metal, a glass, or a polymer).

In an example application, the porous oxide membrane or body may be integrated into an electrochemical energy storage device as a separator. In this case, a polymer layer may also be deposited onto the surface of the porous oxide membrane or body (e.g., to close the pores of the porous oxide membrane or body to prevent ion transport at temperatures above a threshold temperature in the range of about 70° C. to about 130° C.).

BRIEF DESCRIPTION OF THE DRAWINGS

The accompanying drawings are presented to aid in the description of embodiments of the disclosure and are provided solely for illustration of the embodiments and not limitation thereof. Unless otherwise stated or implied by context, different hatchings, shadings, and/or fill patterns in the drawings are meant only to draw contrast between different components, elements, features, etc., and are not meant to convey the use of particular materials, colors, or other properties that may be defined outside of the present disclosure for the specific pattern employed.

FIGS. 1A-1G, 2A-2C, 3, 4A-4C, 5, 6A-6C, 7, 8A-8B, 9A-9B, and 10A-10C illustrate examples of nanowire (small wire) formations, modifications, and characterizations.

FIGS. 11A-11C and 12A-12C illustrate other example aspects of nanowire formation.

DETAILED DESCRIPTION

Figure 1G:
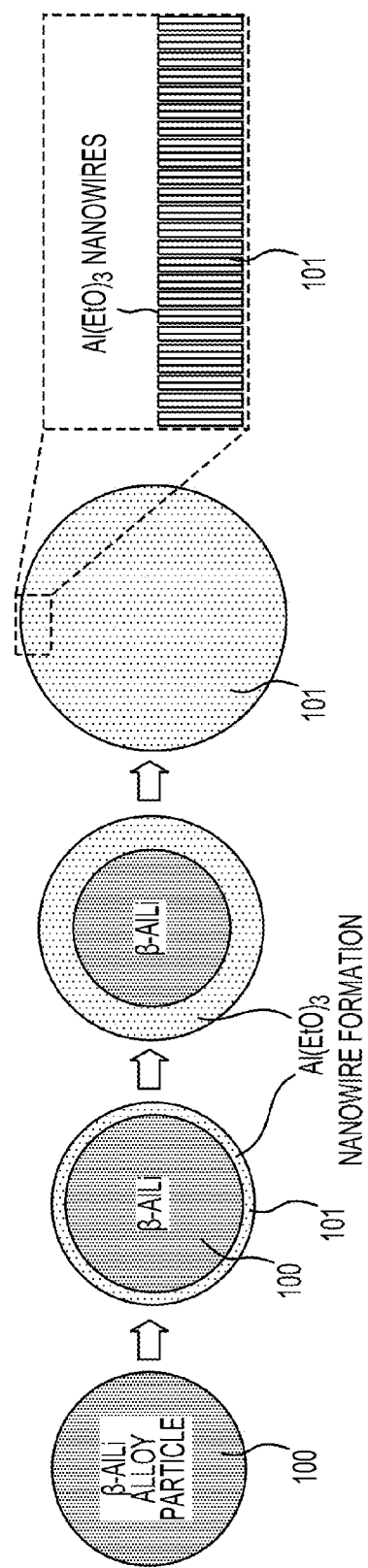

Aspects of the present invention are disclosed in the following description and related drawings directed to specific embodiments of the invention. The term "embodiments of the invention" does not require that all embodiments of the invention include the discussed feature, advantage, process, or mode of operation, and alternate embodiments may be devised without departing from the scope of the invention. Additionally, well-known elements of the invention may not be described in detail or may be omitted so as not to obscure other, more relevant details.

While the description below may describe certain examples in the context of aluminum—(Al) or oxygen—(O) comprising small (nano)wires, whiskers, fibers, and other elongated particles, as well as various porous materials (including porous elongated particles), it will be appreciated that various aspects may be applicable to other compositions.

The description below may describe certain examples of the formation of alkoxides of nonreactive metal(s) (metals and semimetals that typically exhibit very small reactivity upon direct contact with alcohols) by forming alloys with significantly more reactive metals in the context of Al as a nonreactive metal and Li as a reactive metal. However, it will be appreciated that alkoxides of many other nonreactive metals (not just Al) or mixtures of nonreactive metals may be formed using this approach and other reactive metals (not just Li) and reactive metal mixtures may be utilized as alloy elements.

While the description below also may describe certain examples of the formation of certain organometallic compounds of nonreactive metal(s) in the context of alkoxides, it will be appreciated that various aspects of the present disclosure may be applicable to other organometallic (metalorganic) compounds, where alloys of nonreactive metals with reactive metals (e.g., metals having a reactivity, with respect to a given organic compound, that is preferably 5 times higher or more than the reactivity of the nonreactive metals) are used in the synthesis instead of pure nonreactive metals (or instead of their salts and other compounds). Similarly, the solubility of metalorganic compound(s) of reactive metals in the organic solvent (or solvent mix) used in the reaction may preferably be 5 times higher or more than the solubility of the metalorganic compound(s) of nonreactive metals in this solvent.

While the description below also may describe certain examples in the context of the formation of certain oxides of metal(s) (of various particle shapes as well as porous bulk materials), it will be appreciated that various aspects of the present disclosure may be applicable to the formation of other ceramic materials (not necessarily oxides, but also fluorides, oxy-fluorides, carbides, oxy-carbides, nitrides, oxy-nitrides, phosphides, oxy-phosphides, sulfides, selenides, and others) as well as metals and metal alloys.

For simplicity and illustration purposes, all elongated particles of suitable size, shape, aspect ratios, density, porosity, crystal structure, and morphology may be generally referred to herein as "small wires." In various aspects of the present disclosure, the suitable diameter (or width) of individual small wires may range from around 2 nm to around 10 microns and the suitable length of individual small wires may range from around 50 nm to around 50 mm. The suitable aspect ratio (width-to-length) of individual small wires may range from around 1:4 to around 1:10,000,000. Depending on the application, the suitable true density (taking into consideration closed porosity) may range from around 0.1 to around 4 g/cm$^3$ (for small wires comprising only Al metal in their composition) and to around 7 g/cm$^3$ (for small wires comprising metals other than Al in their composition). Depending on the application and the processing conditions, the suitable pore volume within individual small wires may range from around 0 to around 5 cm$^3$/g. Depending on the application and the processing conditions, the microstructure may range from amorphous to nanocrystalline to polycrystalline to single crystalline to a mixture of those to other types. Depending on the application and synthesis conditions, the suitable surface roughness of the small wires may range from around 0 to around 50 nm.

Conventional techniques for the synthesis of ceramic nanowires, whiskers, and fibers include catalyst-assisted chemical vapor deposition (CVD), cylindrical template-based synthesis, hydrothermal synthesis, electrospinning, formation of small rolls from platelets, and others. Such techniques typically suffer from high cost and small yield (particularly in the case of CVD, electrospinning, and hydrothermal synthesis at high pressures), often short length and low aspect ratio of the elongated particles (particularly in the case of rolling platelets and hydrothermal syntheses), poor control over the dimensions (diameter and length) of the elongated particles, often the inability to produce porous elongated particles with high aspect ratios, limited (or the lack of) control in porosity and surface morphology of elongated particles, and other limitations.

Carbon nanotubes (CNTs) are typically used as conventional fillers for many polymer and metal composites to improve various mechanical and other properties. However, CNTs are difficult to disperse uniformly and are difficult to form an interface having controllable strength therewith. In addition, they are not transparent and are typically electrically conductive (which may be undesirable for some applications), suffer from poor thermal stability in oxygen-containing environments (due to oxidation), and have other limitations.

The present disclosure offers routes to overcome (or significantly reduce) the above limitations.

Conventional production of many metal alkoxides (e.g., aluminum alkoxides) as well as many other metalorganic compounds typically requires the use of catalysts. For example, formation of aluminum ethoxide ($Al(EtO)_3$) and aluminum isopropoxide ($Al(i-PrO)_3$) typically requires the use of $HgCl_2$, $I_2$, $AlCl_3$, $FeCl_3$, $SnCl_4$, or $B_2O_3$ catalysts (some of which are toxic and corrosive). This makes the synthesis process relatively expensive, requires additional purification steps, and limits the purity of the end result.

The present disclosure describes examples of methods for a low cost and large volume (bulk) production of these materials. Furthermore, it provides avenues for the formation of organometallic compounds (for example, aluminum alkoxides) in the form of elongated particles (which are referred to herein as "small wires") of controlled dimensions and high aspect ratios. This may be attractive for different applications, including those that involve further chemical modifications of these materials to produce other materials (such as metal (e.g., Al) oxyhydroxides, hydroxides, oxides, oxy-halides, halides, oxy-carbides, carbides, nitrides, oxy-nitrides, phosphides, oxy-phosphides, sulfides, selenides, tellurides, and various mixed ceramics and doped ceramic materials, among others, to name a few examples) in the form of high surface area small wires as well as membranes and various porous structures having high specific surface area (e.g., from around 1 to around 3,000 $m^2/g$) and other useful properties (e.g., high strength, high toughness, high activity, high thermal stability, low thermal expansion, high surface area, etc., depending on the final material form).

In one illustrative example, aluminum alkoxides may be produced by the reaction of an Al alloy of a suitable composition with an alcohol. Suitable Al alloy compositions may include both aluminum and a significant atomic fraction (e.g., typically greater than 40 at. %) of a metal that is highly reactive with alcohols, forming, for example, alkoxides of the corresponding metal. It is typically preferable that these reaction product(s) (metal alkoxides) be dissolved in the alcohol solution during the reaction while having a majority of the aluminum alkoxide product remaining undissolved (which would typically require these metal alkoxides to have significantly higher solubility than aluminum alkoxide, preferably by at least 5 times higher or more; even more preferably 50 times higher or more). Reactivity of metals (or materials, in general) as well as their solubility depends not only on the element, but also on the solvent (such as an organic compound or water or their mixture) and the reaction temperature and pressure. However, for many solvents and for moderate temperatures (e.g., 0-100° C.) and for near atmospheric pressures some of the metals (electropositive elements) may typically be relatively reactive. Examples of such reactive metals include, but are not limited to, alkali metals (e.g., Li, Na, K, etc.) and alkaline earth metals (e.g., Ca, Mg, Sr, Be, etc.), to provide a few examples. Combinations of the reactive metals may also be used in the alloy. In a more particular example, an aluminum-alkali metal alloy (e.g., aluminum-lithium alloy) may react with an alcohol (e.g., with ethanol, methanol, propanol and many others alcohols, discussed in turn below), forming aluminum alkoxides. This finding by the inventors was unexpected because Al is generally understood not to be reactive with alcohols. The inventors hypothesize that when Al atoms are finely intermixed with more reactive metal atoms in the alloy (particularly, when aluminum forms intermetallic compounds (e.g., line compounds in the corresponding phase diagrams) with such elements), formation of aluminum alkoxide becomes possible. In addition to aluminum alkoxides, such a method (the use of alloys of "non-reactive" metals with "reactive" metals) may be suitable for the formation of "non-reactive" or "poorly reactive" alkoxides of other metals. These include, but are not limited to, various alkoxides of transition metals (e.g., Ti, V, Cr, Mn, Fe, Co, Ni, Cu, Y, Zr, Nb, Mo, Ru, Rh, Pd, Ag, Hf, Ta, W, Re, Os, Ir, Pt, Au, etc.), various poor metals (Al, Zn, Ga, Cd, In, Sn, Sb, Hg, Tl, Pb, Bi, P, etc.), various rare earth metals (La, Ce, Gd, etc.), and nonmetals (B, Si, P, As, Ge, Se, Te, etc.). Similarly, using alloys of nonreactive (or substantially less reactive) metals with reactive metals (instead of pure nonreactive metals or their salts and other compounds) may allow low-cost synthesis of a broad range of other organometallic (or metalorganic) compounds. Depending on the nature of the metal-carbon bond, these include, but are not limited to: (i) various ionic organometallic compounds, (ii) various organometallic compounds containing metal-carbon sigma bonds, (iii) various ylides, (iv) various organometallic compounds with multicenter bonds, and (v) various organometallic compounds with pi bonded ligands, among others. It should be noted, however, that the term "reactivity" is relative. In some examples, two relatively reactive metals (for example, Li and Mg) could be utilized to form an alloy (e.g., Li—Mg alloy), where preferential or faster reaction and dissolution of Li into selected organic solvents (such as alcohols) may lead to a faster formation of Mg-containing organometallic nanostructures (such as Mg alkoxides). If the amount of solvent is limited, Mg (in this example) organometallic dissolution may be minimized in order to separate solid Mg-containing compounds (such as Mg-containing nanostructures).

Returning to the example of exposure of the aluminum alloy to an alcohol, the formation of aluminum alkoxides and reactive metal (e.g., alkali metal) alkoxides may take place. In the simplest case, such a reaction may proceed in a liquid phase (e.g., in an alcohol or an alcohol-comprising solution). The reaction temperature may vary in a broad range from around the freezing point of the alcohol (or alcohol-comprising solution) to above the boiling point of the alcohol (or alcohol-comprising solution). If the reaction proceeds at above atmospheric pressure, the temperature of the reaction may be increased to significantly above the boiling point of the alcohol (or alcohol-comprising solution). Overall, depending on the synthesis conditions, alcohols, the desired form of the final compounds (alkoxides), and thermal stability of the alkoxides, the suitable temperature range may vary from around −120° C. to around +1000° C. Lower temperatures typically reduce reaction rates and change the diameter of the resultant small wires. Higher temperatures may induce melting of alkoxides and too high of a temperature may induce decomposition of alkoxides. For economic and other reasons, it may be preferred in some applications to conduct such reactions at around atmospheric pressure and in a temperature range from around −20° C. to around +200° C. As will be discussed below, by changing the reaction temperature, the shape and morphology of the produced aluminum alkoxide may be tuned as desired. Upon exposure of aluminum-lithium alloy to an alcohol (or alcohol-comprising) solution, formation of aluminum alkoxides and lithium alkoxides was found to take place. Higher solubility of lithium alkoxides leads to their dissolution into the alcohol or alcohol-comprising solution. As a result, aluminum alkoxides may be easily separated from such a solution in the form of the solid products (e.g., in the form of aluminum alkoxide small wires).

The suitable composition of such an aluminum alloy may vary. For example, such an alloy may primarily (e.g., 97-100%) comprise: (i) aluminum and (ii) reactive metal (e.g., alkali, alkali earth, or various mixtures of alkali and/or alkali earth elements). As illustrative examples, an alloy composition may be $Al_{0.5}Li_{0.5}$ or $Al_2Li_3$ or $Al_4Li_9$ or various other compositions $Al_xLi_{1-x}$, where x>0, etc. In some configurations, it may be preferred that the majority (50-100%) of alkali metal atoms in the alloy are Li atoms. In the case of an $Al_xLi_{1-x}$ alloy, too high of an atomic fraction of Al atoms (e.g., greater than around 53%) typically leads to a microstructure comprising a mixture of Al and AlLi phases. If the size of Al phase grains is large (e.g., greater than around 2-10 nm, depending on reaction conditions), the reaction of the alloy with a suitable alcohol (or alcohol-comprising) solution may yield a mixture of Al and Al alkoxides. In some cases (particularly when the atomic fraction of Al atoms in such an alloy is relatively high (e.g., greater than around 60%), Al may form an interconnected porous network, which may be useful for some applications. For example, formation and further dissolution of Al alkoxide in such an Al—Al alkoxide composite may yield porous Al, which may also be a useful product for electronic, energy storage, energy conversion, energy dampening, and various structural or multifunctional applications. In cases where the atomic fraction of Al atoms in an $Al_xLi_{1-x}$ alloy is reduced and becomes too low (e.g., less than around 40%), the yield of the Al alkoxide (as the wt. % of the initial alloy) will naturally be reduced. However, by varying the relative Al content, one may tune the morphology of the Al alkoxide products and the rate of the alkoxide formation reaction, which may be advantageous for industrial production. In addition to using alloys that primarily (e.g., 97-100%) comprise aluminum and alkali metal (e.g., Li) atoms, a suitable alloy may also comprise 3% or more of other elements (e.g., either as impurities or as useful alloy components).

As discussed briefly above, another significant advantage of the disclosed formation of nonreactive metal (e.g., Al) alkoxide products is that the disclosed process may result in the formation of elongated particles (small wires) of alkoxides. Furthermore, the size, morphology, and aspect ratio of such small wires is tunable in a broad range by changing the synthesis reaction conditions, the composition of the alloy, and the composition of the reactive alcohol solution. A low cost, large volume (bulk) production of alkoxides (or other compounds) of Al or other metals of controllable (tunable) dimensions may be particularly attractive in many applications.

In some applications, it may be advantageous to convert alkoxide (e.g., aluminum alkoxide) or other metalorganic or metallic samples into oxide samples. In particular, if the alkoxide (e.g., aluminum alkoxide) or other metalorganic or metallic samples are in the form of small wires (either individual or bonded), it may be advantageous for some applications to transform them into oxide small wires (either individual or bonded, thus forming a porous oxide body or a porous oxide membrane). In one example, such a conversion may take place by heating alkoxide samples in an oxygen-comprising (or, in some cases, ozone-comprising) gaseous environment (e.g., in air). Pressure for such a conversion reaction may vary over a broad range, from around 0.0000000001 atm to around 100,000 atm. Lower pressure typically reduces the reaction rate. For economical or other reasons, it may be preferred for the conversion reaction to proceed at around atmospheric pressure. Suitable reaction temperatures depend on the particular chemistry of the alkoxide, reaction pressure, the composition of the gaseous environment, the partial pressure of oxygen, and other parameters. Higher temperatures increase conversion reaction rates, but may induce sintering and coarsening of the oxide particles or oxide melting (which may be undesirable in some applications). Typically, suitable reaction temperatures are in the range from around 0° C. to around 2000° C. Even more typically, suitable reaction temperatures are in the range from around 20° C. to around 1500° C. In some applications, it may be preferable to gradually increase the annealing temperature in an oxygen-containing environment in order to initially form a more thermally stable shell around the particles and thus prevent significant shape change of the alkoxide particles during heating to higher temperatures (alkoxide particles (small wires) may otherwise sinter, coarsen, and melt). For example, melting points of aluminum ethoxide, aluminum methoxide, aluminum propoxide, and many other aluminum alkoxides is in the range from around 120 to around 200° C. It is, therefore, advantageous for some applications to prevent alkoxide small wires from melting during heating (e.g., by the formation of such a more thermally stable shell/surface layer). In some applications, such a shape preserving shell may also be formed prior to heating in a gaseous or liquid environment. In some applications when formation of porous oxide membranes or porous oxide bodies is desirable, bonding (cross-linking or sintering) of individual small wires during heating may be preferable. As such, depending on the particular application and the desired end-product, the conditions, environment, and protocol of the alkoxide-to-oxide conversion reaction may vary. It is noted that alkoxide-to-oxide conversion reactions typically lead to a significant volume reduction of the material. In some applications, such a volume reduction may lead to the formation of porous oxide samples (e.g., porous oxide small wires) with either internal (closed) or external (open) pores, or both. Formation of pores may increase the surface area of the oxide samples and may also reduce their density, which may be preferred in some applications.

In addition to the conversion of various organometallic compounds to oxides, it may be advantageous for some applications to convert organometallic compounds (particularly in the form of small wires or porous materials) into other chemical compounds (materials), such as metal oxy-hydroxides, hydroxides, etc., and other ceramic materials, such as oxy-halides, halides, oxy-carbides, carbides, nitrides, oxy-nitrides, phosphides, oxy-phosphides, sulfides, selenides, tellurides, and various mixed ceramics and doped ceramic materials, among others, to name a few examples. It may similarly be advantageous if the shape of the samples do not change significantly during such transformations. Like the previously described case of oxide(s) formation, a similarly broad range of temperatures and pressures and similar methods may be utilized, depending on the particular chemistry. If the conversion takes place in a gaseous environment, the environment may comprise other reactive species with electronegative ceramic-forming elements instead of (or in addition to) oxygen-containing reactive gases, such as reactive gases comprising: halogens (F, Cl, I, Br), sulfur (S), selenium (Se), nitrogen (N), phosphorous (P), carbon (C), and other ceramic-forming elements (depending on the desired composition of the nanostructured ceramic materials).

In some designs, it may be advantageous to convert species from the initially formed metalorganic compounds into final compounds using one or more intermediate steps. For example, in some applications (e.g., to further produce oxide small wires with reduced or no porosity (including formation of single crystalline oxide small wires) during subsequent treatments), it may be advantageous to convert metalorganic (e.g., alkoxide, such as aluminum alkoxide) samples (e.g., aluminum alkoxide small wires, etc.) to oxyhydroxide (e.g., boehmite (AlOOH) or another polymorph crystalline or amorphous microstructure) or hydroxide (e.g., $Al(OH)_3$—having, for example, bayerite, gibbsite, nordstrandite, pseudoboehmite, or another polymorph microstructure) samples. In some applications, it may be further advantageous to preserve the elongated shape and individuality of the small wire samples during such transformations. In other applications, it may be advantageous and useful to produce porous structures of controlled porosity and dimensions from the initial alkoxide small wires (or porous alkoxide material). Several methods may be employed for this conversion. For example, one may use a controlled hydrolysis of aluminium alkoxide samples in water-containing solvent(s) or water under controlled temperature to produce either aluminum hydroxide or aluminum oxyhydroxide/monohydroxide AlO(OH) either of amorphous microstructure (typically at temperatures lower than around 50-70° C.) or crystalline (e.g., boehmite) structure (typically at higher temperatures, e.g., at or above around 70-90° C.). Treatment/reaction time may range from around 1 minute to around 30 days. Shorter time is typically difficult to control. Longer time may become less economical. In some applications, it may be advantageous to heat the water-free alkoxide powder-comprising solution to the desired temperature before introducing a water-comprising solution (e.g., also preheated) to conduct hydrolysis. It may be preferred that this solution exhibits minimal solubility (e.g., below around 0.02M) for both the alkoxide and the final product (e.g., oxyhydroxide, hydroxide, etc.) in order to largely preserve the elongated shape of the small wires and avoid significant material losses. Alkali metal alkoxides (e.g., lithium alkoxide) or alkaline earth metal alkoxides (e.g., magnesium alkoxide or calcium alkoxide) or other compounds that have higher solubility in these solutions may be pre-dissolved in them in order to reduce the solubility of aluminum alkoxides or the final product in these (e.g., in water or water-containing) solutions. In some applications, it may be preferred for the alcohol tail(s) of all the alkoxides to be identical (e.g., if aluminum ethoxides are being transformed it may be preferred in some applications to use alkali metal ethoxide for the pre-dissolution in the solution). In some applications, a water solution in ionic liquids may be used for the transformation reactions. Once alkoxide samples (e.g., small wires) are first converted to oxyhydroxide or hydroxide samples (preferably crystalline small wires), these samples may be further converted to oxide samples (e.g., oxide small wires) having minimal (or no) pores and having an ordered crystalline microstructure. By controlling the concentration of water, the composition of the reactive solution, and the reaction temperature, one may control the morphology, chemistry, and crystal structure of the converted oxyhydroxide or hydroxide samples.

Changing one or more properties (e.g., increasing pH) of the water or water-containing solution may be another tool employed for controlling microstructure, composition, and morphology of the converted oxyhydroxide or hydroxide samples. LiOH may be used to increase the pH of the treatment (hydrolysis) solution. KOH or NaOH or other bases may similarly be used for this purpose. Higher pH may favor transformation to $Al(OH)_3$. Higher treatment temperature similarly favors formation of crystalline microstructure. In some applications, it may be further advantageous to first transform Al alkoxide particles to AlOOH before further transforming to $Al(OH)_3$. Similarly, control of pH (typically in the range from about 5 to about 14) may be utilized to tune the morphology of other conversion (or transformation) reaction products as well as the morphology of the nanostructured materials produced by the selective dissolution of one (or more) metals from metal alloys.

In some designs, it may be advantageous to add organic or inorganic salts or "inert" co-solvents to the "reactive" solvent (by which it will be understood that "reactive" refers to the solvent which may form organometallic compounds upon immersion of the suitable alloy into it) in order to tune the morphology of the desired organometallic compound (e.g., alkoxide) or in order to reduce the solubility of at least one of the alloy components. In some designs, the added salt may comprise the component of the alloy (e.g., Al salt such as $AlCl_3$ and others, etc., or Li salt such as LiCl and others in the case of a reaction with an AlLi alloy).

In some designs and alloy compositions, water may be used in addition to (or instead of) organic solvents to selectively dissolve one or more metals from metal alloys and produce nanostructured (porous materials, small wire-shaped particles, nanoparticles, etc.) metal-comprising compounds of less reactive metals. A broad range of pressures and temperatures may be utilized, as described above for the formation of alkoxides.

In some designs, instead of transforming (converting) metalorganic small wires (or porous materials) (e.g., formed as disclosed herein) into oxide or other ceramic small wires or porous materials by direct (or indirect) transformation reaction(s), one may transform nanostructured metalorganic compounds into small metal wires or porous metals. In contrast to conventional methods for the formation of small metal wires and porous metal structures, here metalorganic small wires or metal-containing ceramic (e.g., oxides, sulfides, nitrides, selected chalcogenides, etc.) small wires (or the corresponding porous structures) may be first formed (step A) according to (or conceptually similar to) the above-discussed methodology and then (step B) reduced to the corresponding metal form. Such a reduction process may proceed, for example, by using a gaseous reducing agent or in a liquid environment by using a liquid reducing agent (e.g. in a solution). In one example method, formation of the small metal wires (or porous metal structures) may involve an initial formation of silver oxide or silver-based metalorganic small wires (or porous structures) (e.g., by forming Ag—Li, Ag—Na, Ag—Ca, Ag—K, Ag—Mg, or another suitable Ag alloy and its reaction with a suitable solvent under suitable conditions to form silver-containing small wires (or porous structures)), which may be then transformed into silver oxide wires (e.g., upon annealing in an oxygen containing environment) and then reduced into small silver wires. In some cases, metal (e.g., silver) oxide or other metal ceramic or metal-based metalorganic small wires (or porous structures) may be directly transformed into metal small wires or porous metal structures. In some cases, metal (e.g., silver) alloys may be directly transformed into metal small wires or porous metal wires or other porous structures upon preferential dissolution of the more reactive metal into a suitable solvent. Various suitable organic compounds (solvents) may be used instead (not just suitable alcohols) for the formation of organometallic wires. Other metal (not just Ag) and metalloid small wires and porous materials may be produced similarly. Examples of such metals and metalloids include, but are not limited to, Au, Pt, Cu, Ti, Ni, Co, Zn, W, Hf, Ta, Nb, Mo, Ru, Rh, Pd, Bi, La, In, Sn, Ge, and Si, to name a few.

Such small metal wires may be used in various composites, optically transparent conductive coatings, as magnetic materials (in a broad range of applications of soft and hard magnets), scanning probe microscopy tips, surface enhanced Raman scattering techniques, metamaterials (negative refractive index materials), nano-optics, molecular electronics, biological tags, anti-bacterial materials, field emission electron emitters, gas sensors, catalysts, electrically conductive additives (e.g., to enhance electrical conductivity of various paints, plastics, battery or capacitor or supercapacitor electrodes, etc.), conductive inks, current collectors and other applications. In some designs, it may be advantageous for metal small wires (e.g., Cu or Ag and others) to be incorporated into fabrics to provide antibacterial properties. In some designs, it may be advantageous for metal small wires (e.g., Cu or Ag and others) (particularly the small wires produced according to the disclosed methods herein) to be components of the anti-static paints, electromagnetic shielding, conductive inks for touchscreen displays, sensors, smart lenses, and other applications. In some designs, it may be advantageous for metal small wires and porous metal structures (particularly those produced according to the disclosed methods) to be component(s) of rocket fuel or explosives. Different metals (in the form of porous structures or small metal wires) may be more effectively utilized in different applications. For example, small Ta wires and porous Ta may be particularly attractive for applications in electrolytic capacitors. In another illustrative example, Cu, Ag, Cu—Ni alloys and other alloys (in the form of small wires or porous structures) may be attractive for applications in anti-bacterial coatings or paints, or anti-bacterial clothing or fabrics. In yet another illustrative example, Pt, Au, Cu, Ni, and other metal small wires or porous structures may be particularly effective when utilized as catalysts. In yet another illustrative example, Au, Cu, Ni, and Ti small wires may be very effective when used as conductive additives. Some of these applications (e.g., sensors, molecular electronics, biological tags, catalyst, etc.) may benefit from the formation of porous metal wires, which are also enabled by the disclosed methodology herein. In addition to pure small metal wires, the described methodology may allow formation of mixed metal alloys. In this case, alloys of two or more "nonreactive" metals and one or more "reactive" metals may be used as the initial materials.

In addition to the above-discussed solution-based methods for the formation of nanostructured metal-comprising compounds or for various transformation reactions, gas phase conversion may also be utilized in a similar way.

Several example embodiments and corresponding synthesis procedures are described, in turn, below. In a first example, the first synthesis step included formation of β-AlLi by mixing and melting Al and Li components. Battery grade lithium foil and 0.25 mm thick aluminum foil (either 1145 Al alloy or 99.999% pure Al, with the results being nearly identical in terms of the composition and morphology of the final products) were cut into 12.7 mm rounds and Li was sandwiched between Al foils. The mass of Li in this example was chosen to be approximately 20 wt. % (50 at. %) of the total (approximately 80 wt. % and 50 at. % of Al) in order to produce β-AlLi at the congruent melting point. A graphite crucible was used as a sample holder for melting. Samples were rapidly heated to 750° C. at a heating rate of 895° C./min in the graphite crucible with an induction heater. The temperature was measured via an optical pyrometer during heating. After reaching 750° C. the heating was stopped immediately while the molten sample was allowed to cool in an inert environment (Ar gas) at a cooling rate of 150° C./min.

The second step included exposure of the AlLi samples to various solvents (alcohols in this example). More specifically, the produced AlLi pellet samples were placed in 20 mL of an alcohol in a glovebox. The chemical reaction resulted in the formation of hydrogen and possibly other gases, which may be evacuated (e.g., via a bubbler) or collected. All solvents selected in this example were anhydrous alcohols, such as four different homologous series: various linear chain alcohols (e.g., methanol, ethanol, 1-propanol, 1-butanol, 1-hexanol, 1-octanol, among others), various branched alcohols (e.g., ethanol, 2-propanol, t-butanol, among others), various cyclic alcohols (e.g., phenol, among others), and various multi OH group alcohols (e.g., ethylene glycol, among others). A low content of water in alcohols was found to be preferable for the Al alkoxide small wire formation. The maximum tolerable (for small wire formation) $H_2O$ content in alcohols was found to depend on the particular alcohol. Typically, it was found that alcohols should preferably contain below 1000 ppm (often preferably below 100-150 ppm and in some cases (e.g., in the case of ethanol and other low molecular weight alcohols) preferably below 40-50 ppm) of moisture to reproducibly yield Al alkoxide in the shape of small wires. Formation of other metalorganic or metallic nanostructures (including nanoporous and small wire structures comprising non-Al metals) may be more tolerant to water content. After completion of the reaction, solid Al alkoxide products were decanted from the solution to remove residual LiOH products.

FIGS. 1A-1E show an example of aluminum ethoxide $(Al(EtOH)_3)$ formation upon exposure of an AlLi alloy sample to an anhydrous ethanol at low temperatures of 20-60° C. FIGS. 1A-1F show scanning electron microscopy (SEM) images of the various stages of the small wire formation that starts from the surface of the AlLi grain and proceeds until all the AlLi grains are completely converted into $Al(EtOH)_3$ small wires. FIG. 1G shows a schematic of the process taking place in this example. It can be seen that the size of the initial AlLi grains (100) affects the average length of the $Al(EtOH)_3$ small wires (101) produced. Larger grains typically lead to longer small wires. In addition to the illustrated schematics, some of the small wires may grow in between the grains and thus be longer than the average grain radius.

SEM image analysis including small wire diameter measurements were performed manually using open source software ImageJ. Diameter measurements were performed with a sample size N≥150 for each sample type.

As small wires form uniformly around the crystalline grains (see FIGS. 1A-1G), there is evidently no dependence of the wire formation kinetics on β-AlLi grain orientation and no preferential growth on specific crystallographic planes. This suggests that the formation kinetics may be controlled by mass transport (diffusion). As the wire formation process involves both the extraction of Li from the β-LiAl alloy (with the associated tensile stresses at both the surface layer and the interface with the unreacted alloy) and the insertion of EtO groups (with the associated compressive stresses), it is believed that interfacial stresses are responsible for the 1D shape of the produced $Al(EtO)_3$ products.

Figure 2B:
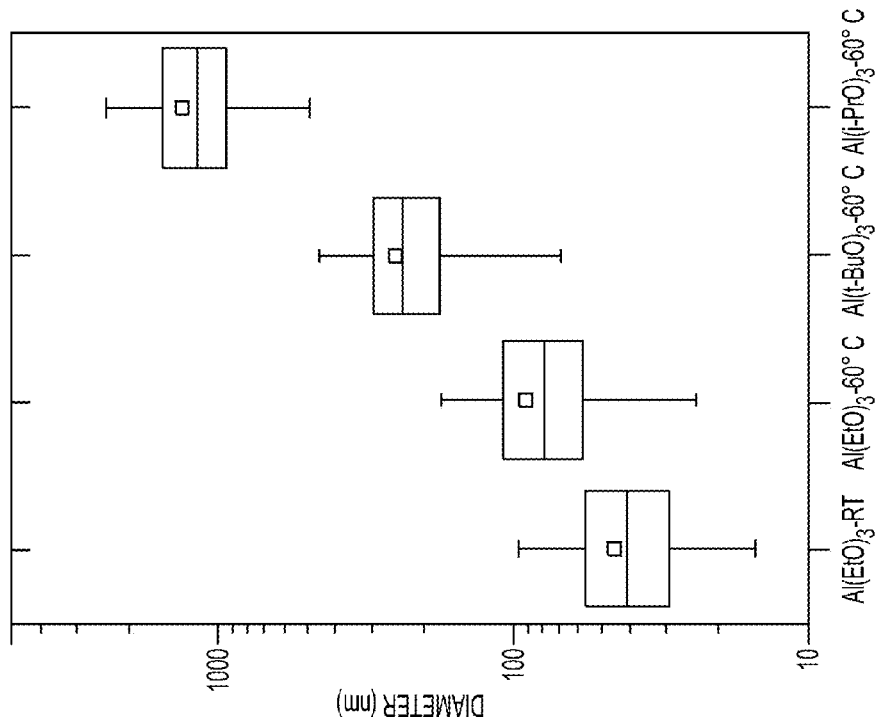
Figure 2A:
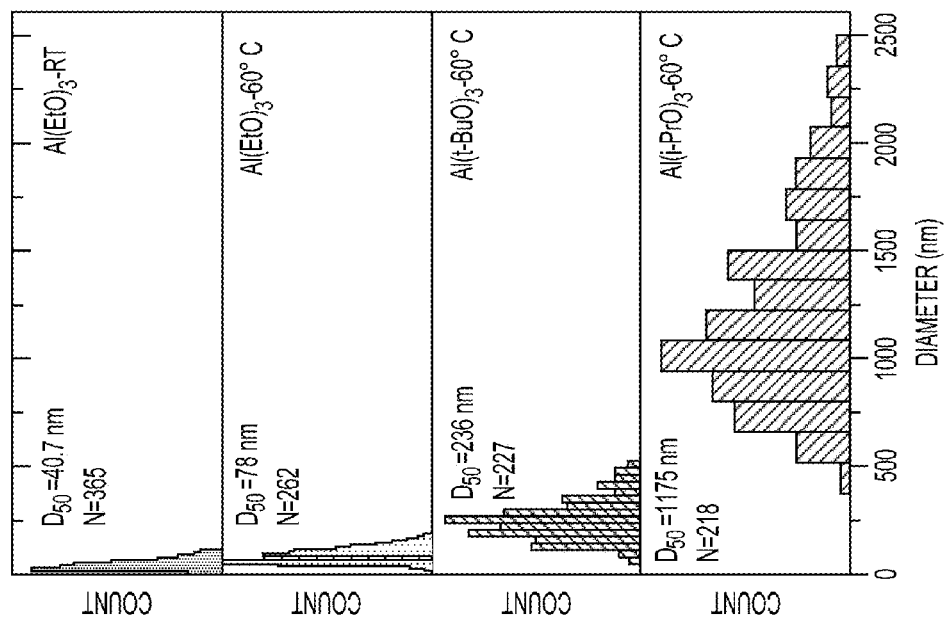
Figure 2C:
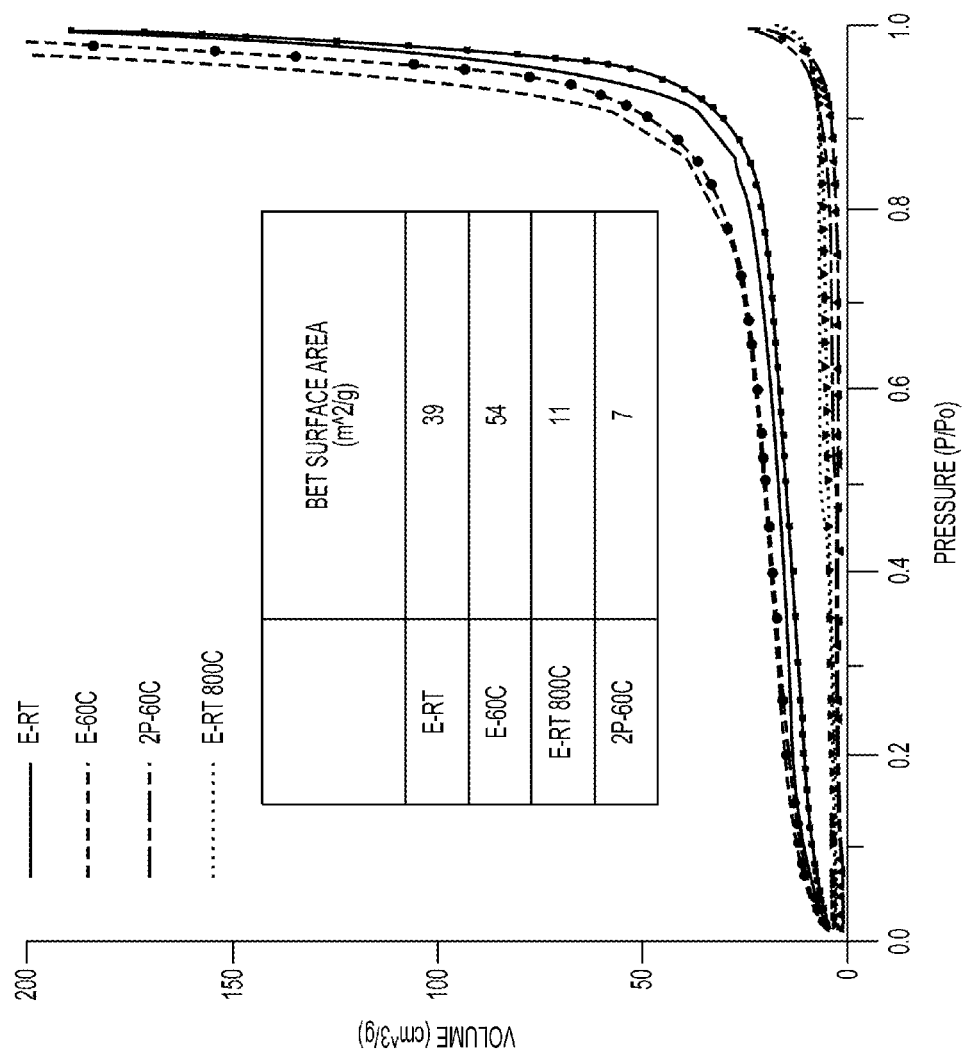

FIGS. 2A-2C show examples of how diameter and specific surface area of aluminum ethoxide $(Al(EtOH)_3)$ small wires may be tuned (changed) by changing the alcohol composition and treatment temperatures. Samples exposed to ethanol are labeled with "E"; to t-buthanol with "T"; and to isopropanol (2-propanol) with "2P". Room temperature experiments are labeled with "RT", while AlLi samples treated with alcohols at 60° C. are labeled with "60C". Overall, FIGS. 2A-2C show an analysis conducted on four samples produced: (i) E-RT, (ii) E-60C (produced by ethanol treatment at room temperature and at 60° C.), (iii) T-60C (produced by t-buthanol treatment at 60° C.) and (iv) 2P-60C (produced by propanol treatment at 60° C.). FIG. 2A shows the average diameter for Al alkoxide small wires for four of these samples. Increasing treatment temperature from room temperature to 60° C. increases the average small wire diameter. Changing the alcohol composition has an even stronger impact on the average width diameter. FIG. 2B shows a small wire diameter distribution measured for samples E-60C, T-60C, and 2P-60C. FIG. 2C shows nitrogen sorption isotherms collected on as-produced samples E-RT, E-60C, and 2P-60C as well as on the sample E-RT after annealing in air at temperatures of up to 800° C. FIG. 2C additionally shows different BET specific surface areas measured on such samples, showing significant modifications in the porosity, maximum $N_2$ gas adsorbed, and specific surface area among these samples.

Figure 3:
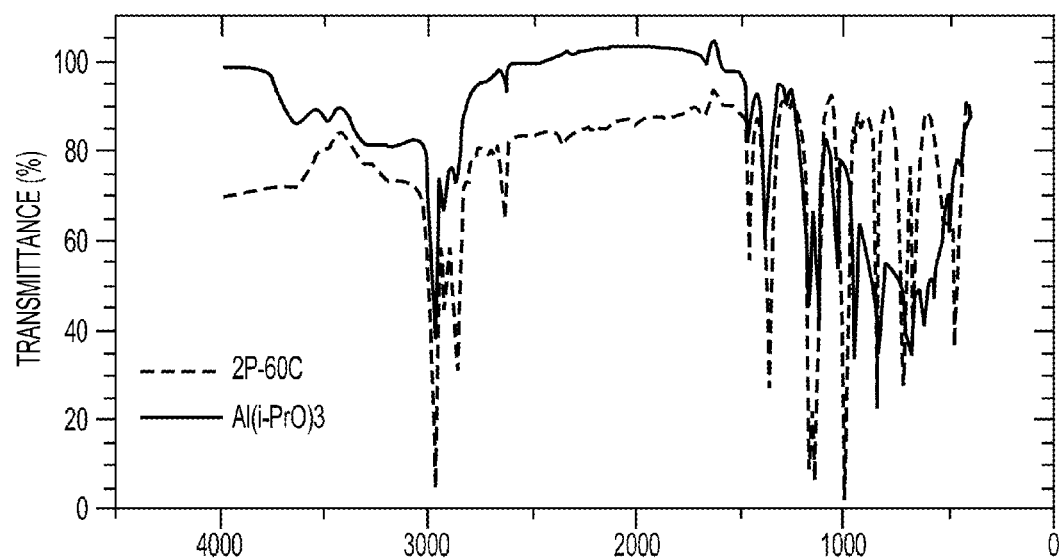
Figure 3:
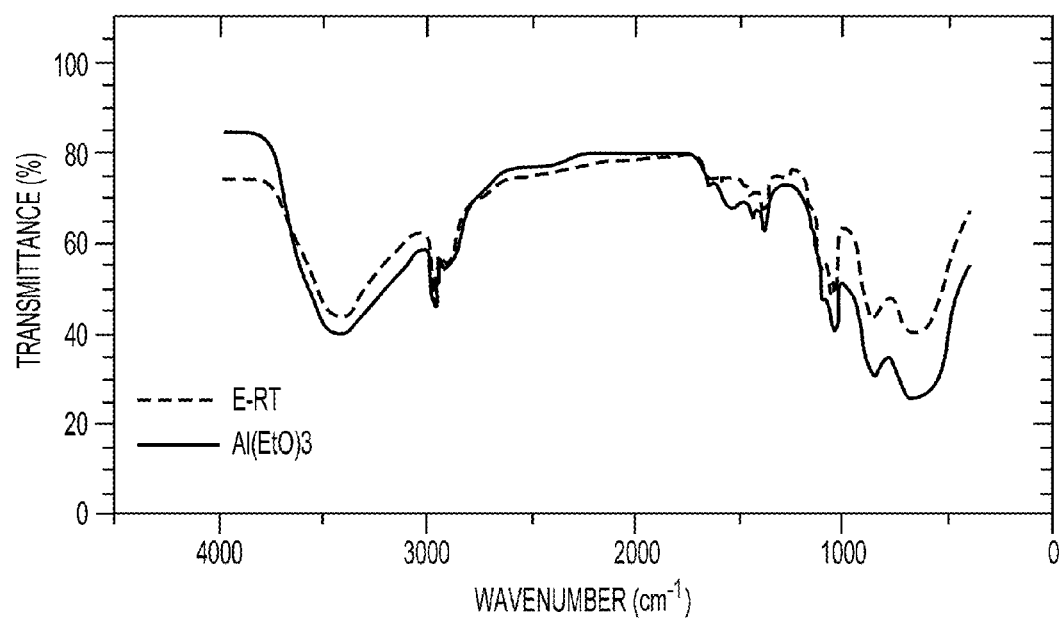

FIG. 3 shows examples of Fourier transform infrared spectroscopy (FTIR) measurements on selected small wires produced in comparison with that of commercially-available aluminum alkoxides of the corresponding alcohols. An excellent match of the peak positions is clearly visible. The shift and broadening of the 3340 cm$^{-1}$ and 935 cm$^{-1}$ peaks to higher and lower frequencies, respectively, are typical of Al(EtO)$_3$ samples and may suggest a partial hydrolysis during FTIR analysis.

Figure 4B:
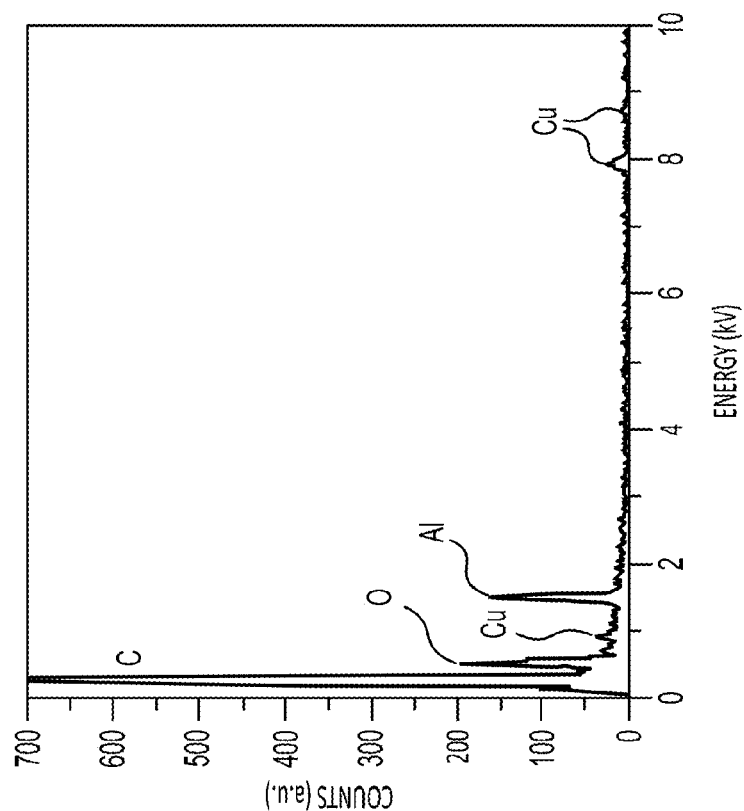
Figure 4A:
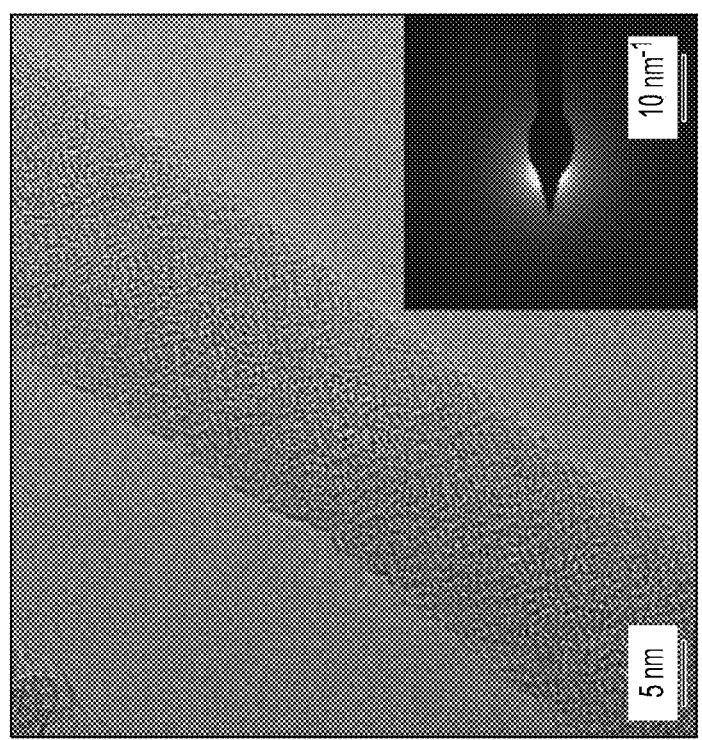
Figure 4C:
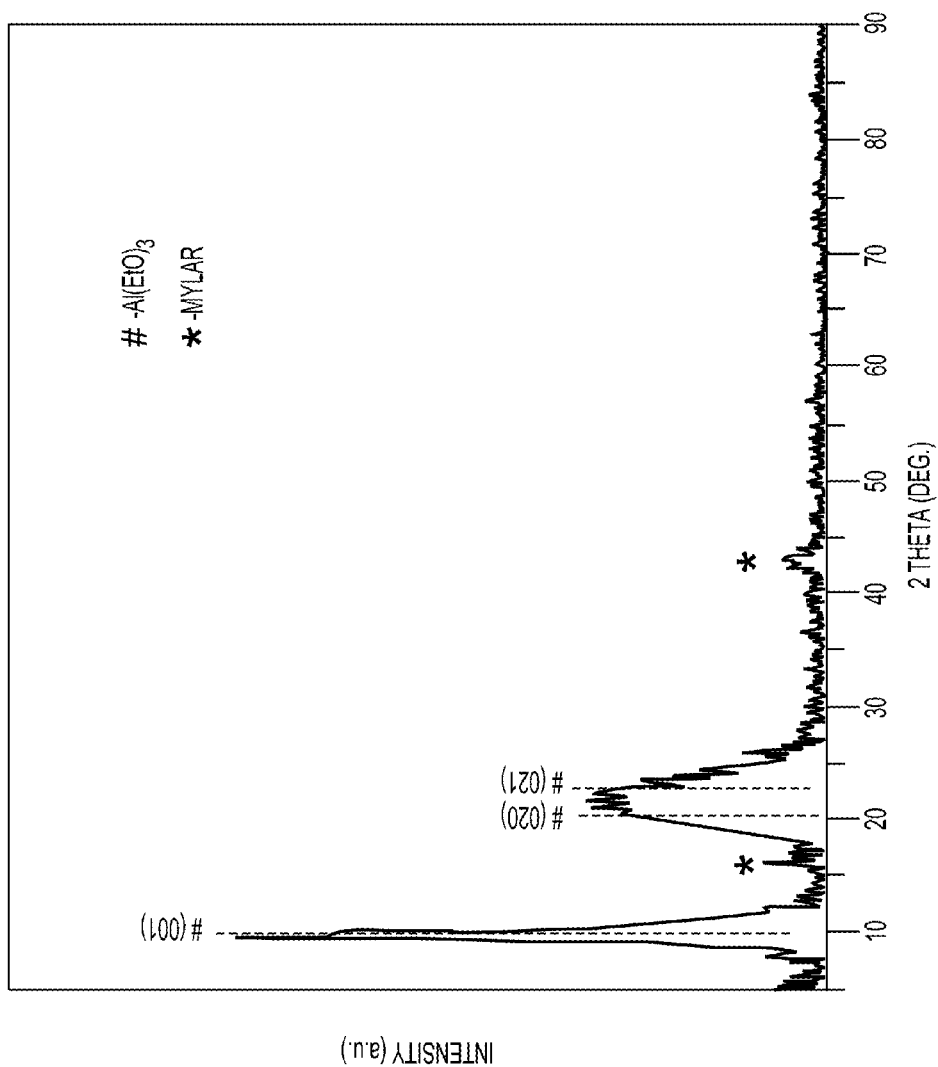

FIGS. 4A-4C provide additional characterization of the small Al(EtO)$_3$ wires formed. FIG. 4A shows an example of high resolution transmission electron microscopy (HRTEM) studies confirming a lack of catalysts at the tips of the formed wires and their amorphous (in this example) morphology. FIG. 4B shows an example energy dispersive spectroscopy (EDS) analysis, which confirms the expected chemical composition and the lack of detectable impurities, although it picked up a Cu signal from the TEM sample holder. As might be expected from the low melting point of Al(EtO)$_3$, the heat generated during TEM imaging (300 kV) was inducing visible damages and shape distortion of the nanowires, preventing recording of high-resolution micrographs during longer collection scans and also possibly affecting the electron diffraction. Thus, X-ray diffraction (XRD) was additionally conducted. To avoid hydrolysis from air interactions and possible crystallinity changes during drying of the produced Al(EtO)3 nanowires, the XRD studies were conducted on samples not exposed to air and suspended in ethanol using a specialized sample holder. FIG. 4C shows a typical XRD spectrum of the sample. While there is agreement in the literature on the monoclinic P21/m structure of Al(EtO)$_3$, there is still a debate on the correct lattice and unit cell size due to the known difficulty of producing high quality crystalline Al(EtO)$_3$ samples. Yet, according to a reference pattern, very broad peaks at around 10 and 22 degr. could be assigned to diffraction on (001) (10.3 degr.), (020) (20.35 degr.) and (021) (22.7 degr.) planes of Al(EtO)$_3$. Their large full width at half maximum gives an estimate of the grain size of only approximately 1.5 nm for the (001) peak, which is considered to be X-ray amorphous. The mostly amorphous nature of the produced Al(EtO)$_3$ is very typical, according to the literature.

Figure 5:
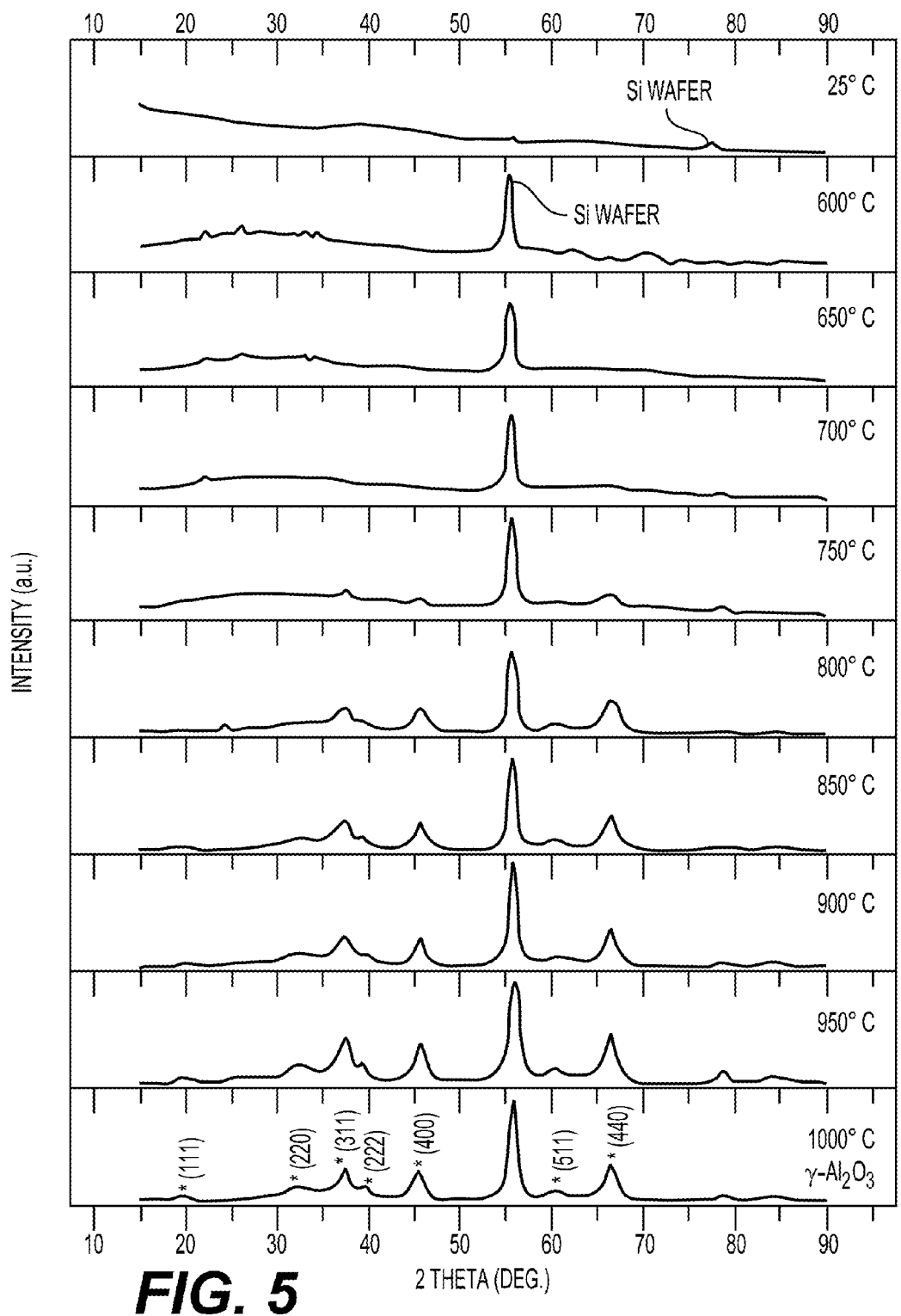

FIG. 5 shows examples of in-situ X-ray diffraction (XRD) studies conducted on an Al(EtO)$_3$ small wire sample (on a Si wafer substrate) in an oxygen-containing environment (such as air, in this example). It demonstrates changes in the microstructure of the sample during heating in air at a heating rate of 4° C./min. The XRD was performed using 30 min collection times and an incident angle $\Omega$=5°. As shown, the formation of clear $\gamma$-Al$_2$O$_3$ peaks become visible after the temperature was increased to around 750° C. in this example.

Figure 6B:
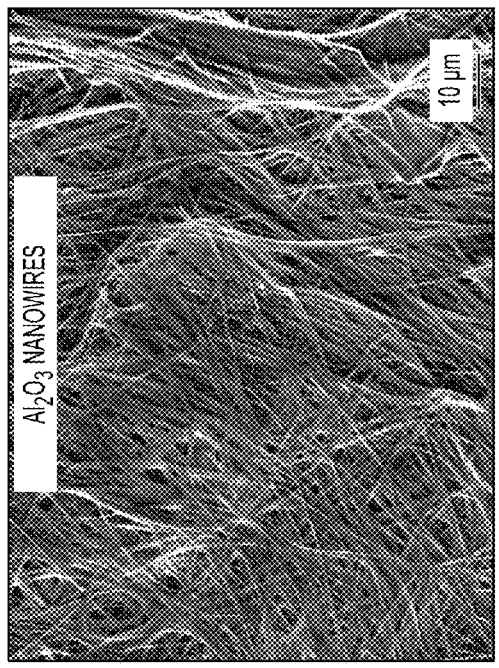
Figure 6C:
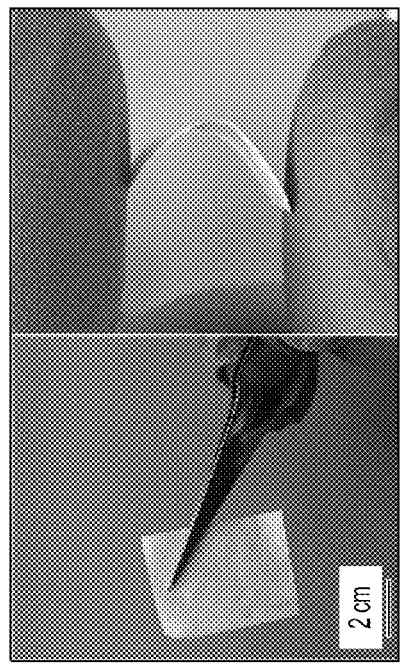
Figure 6A:
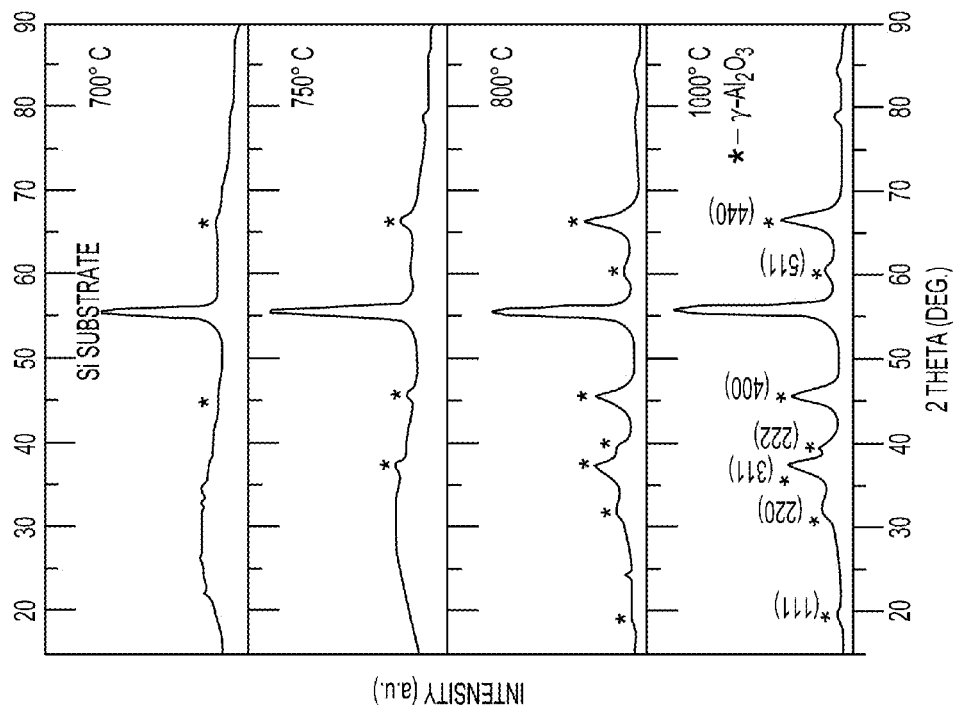

FIGS. 6A-6C show different aspects of the formation of an example flexible, binder-free, nonwoven fabric composed of $\gamma$-Al$_2$O$_3$ small wires using a simple tape casting of the initial Al(EtO)$_3$ small wire suspension in ethanol, followed by a heat-treatment in air. As discussed above, heat treatment of Al(EtO)$_3$ nanowires in air at atmospheric pressure converts them into aluminum oxide (Al$_2$O$_3$) wires. FIG. 6A shows XRD of the samples treated at 700, 750, 800 and 1000° C. Grazing incidence techniques were used to reduce the X-ray penetration depth to less than 50 μm to avoid measurements of the Al$_2$O$_3$ heating stage. FIG. 6B shows an SEM image of the $\gamma$-Al$_2$O$_3$ wires produced by heat-treatment at 1000° C. No signs of pulverization or significant microstructure changes compared to the initial Al(EtO)$_3$ samples could be observed. Such morphology retention may be an advantageous aspect of Al$_2$O$_3$ small wire synthesis for many practical applications. The overall morphology of the produced nonwoven fabric is somewhat similar to that of paper, where the cellulose fibers are replaced here with stronger and stiffer $\gamma$-Al$_2$O$_3$ small wires. Due to the fibrous nature of the produced free-standing films and the small diameter of the $\gamma$-Al$_2$O$_3$ small wires, they exhibit good flexibility. This is in sharp contrast to anodized Al$_2$O$_3$ membranes of comparable thickness that are known to be extremely brittle and difficult to handle. FIG. 6C shows optical images of the nonwoven fabric composed of $\gamma$-Al$_2$O$_3$ small wires.

Figure 7:
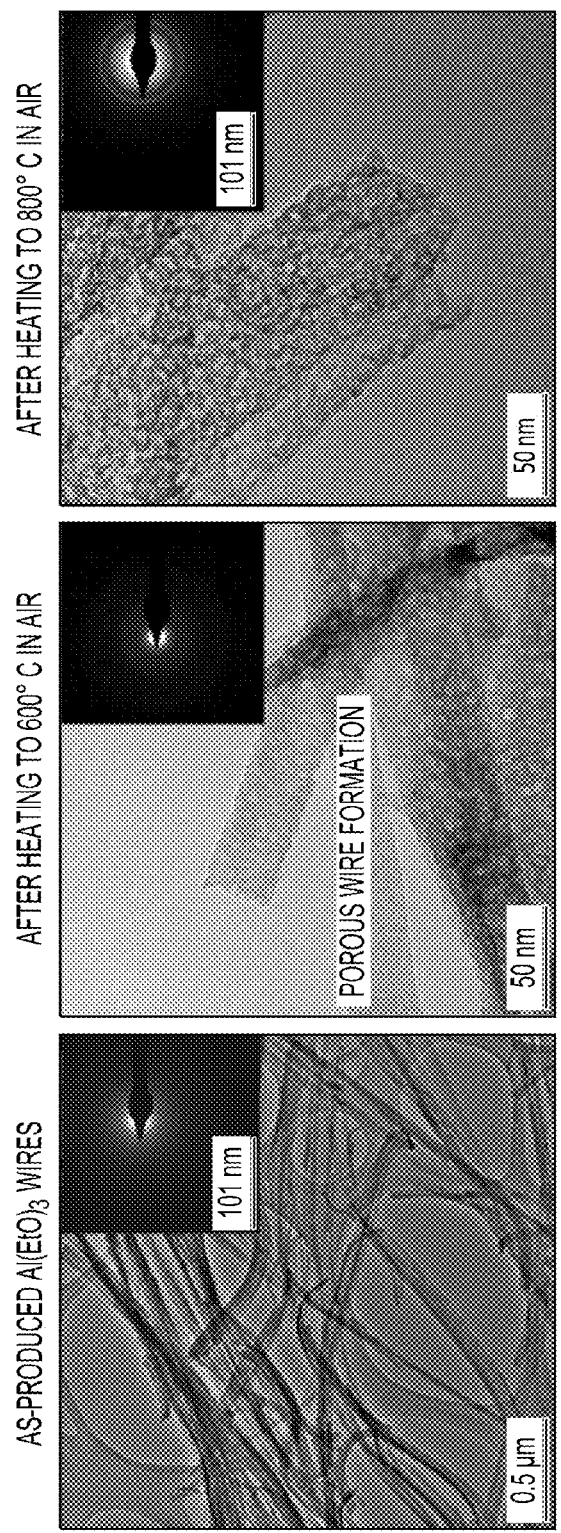

FIG. 7 shows examples of the formation of porous small wires after heating Al(EtO)$_3$ small wire samples in air at 600 and 800° C. Transmission electron microscopy (TEM) micrographs clearly show that initially smooth and nonporous small wires transformed into nanocrystalline (polycrystalline) porous small wires. The electron diffraction pattern of the 800° C.-heated sample corresponds to a $\gamma$-Al$_2$O$_3$ crystal structure of the small wires.

Figure 8A:
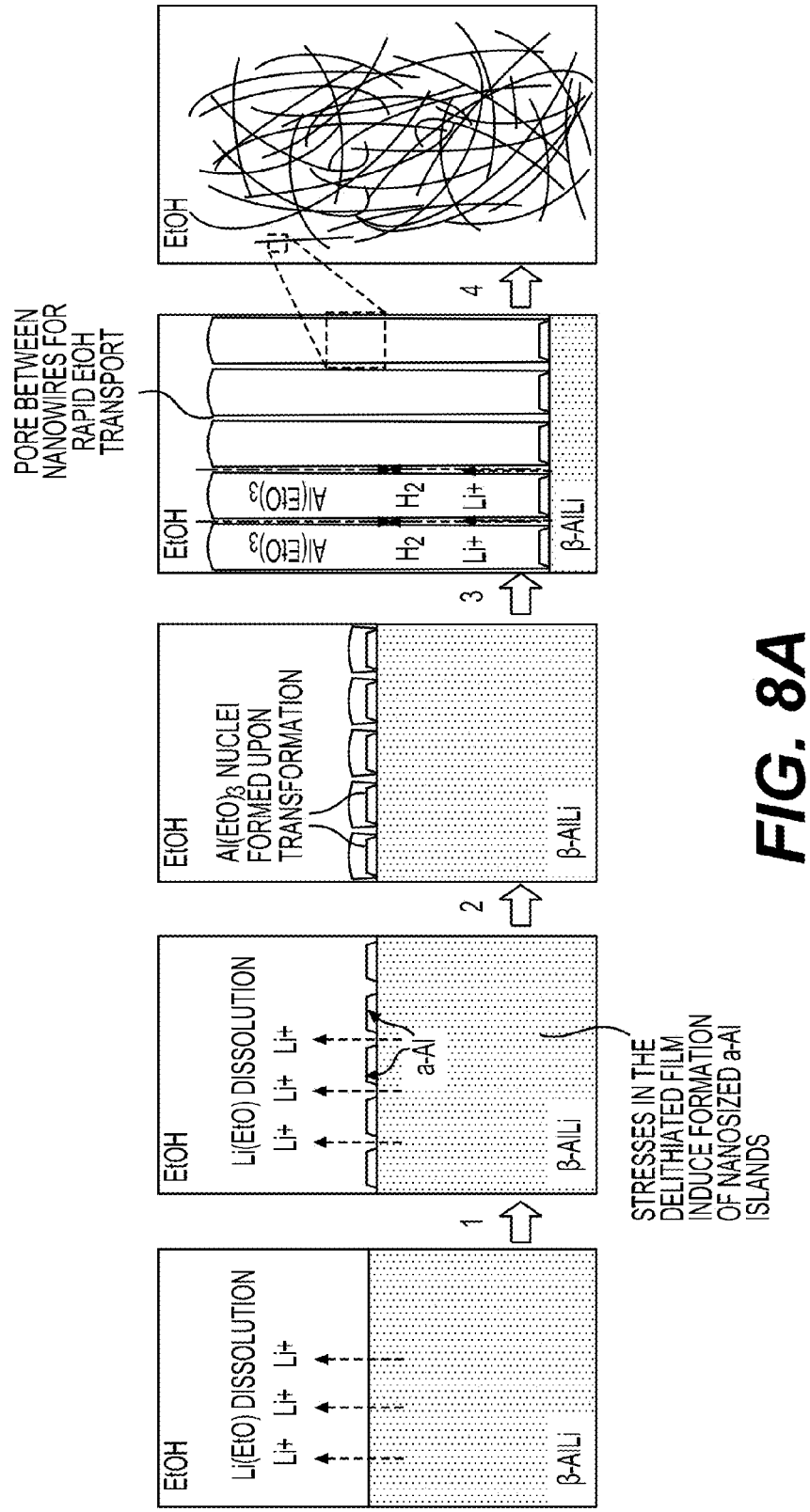
Figure 8B:
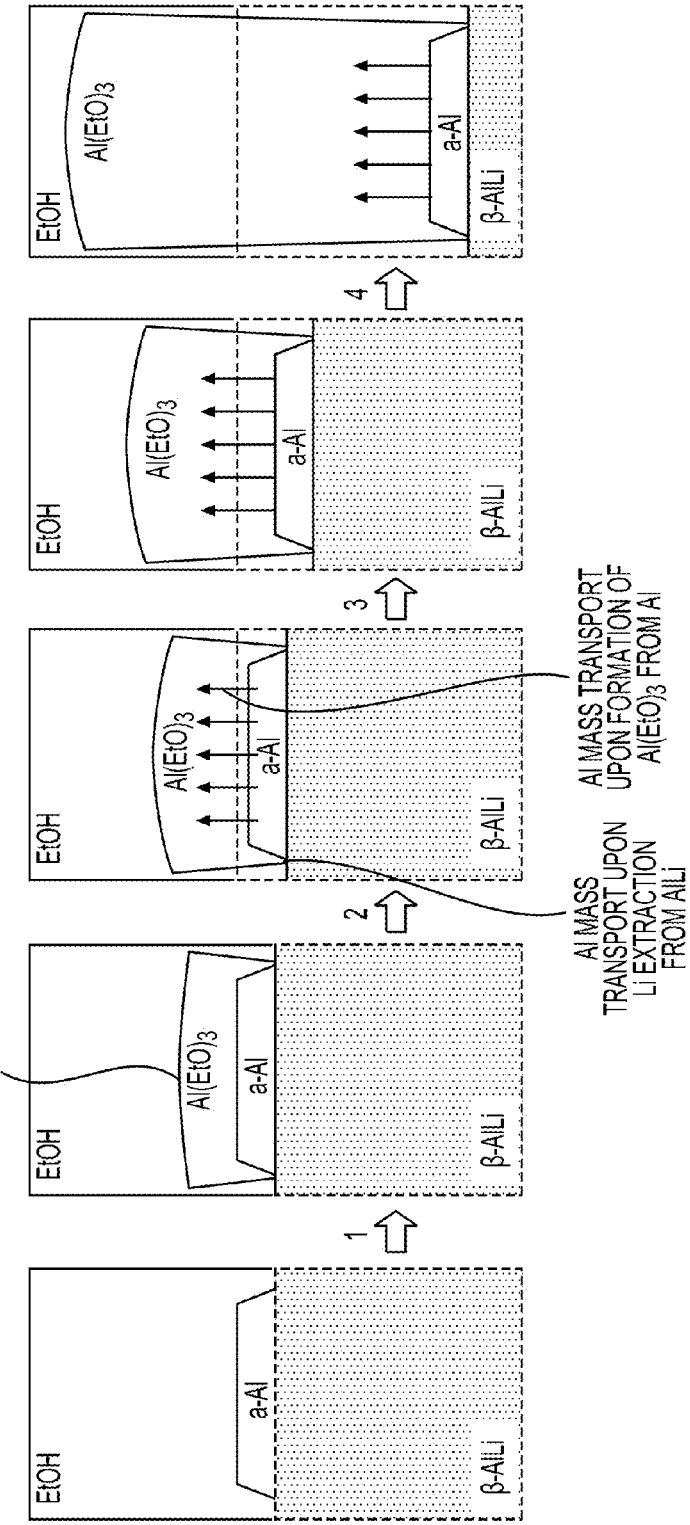

FIGS. 8A-8B show an example of a mechanism that may be involved in the formation of the small wires during preferential dissolution of one of the metal alloy components (such as preferential dissolution of Li from the $\beta$-AlLi as Li(EtO) into ethanol). As noted above, the Al(EtO)$_3$ small wire formation process involves both the extraction of Li from the $\beta$-LiAl alloy (with the associated tensile stresses at both the surface layer and the interface with the unreacted alloy) and the insertion of EtO groups (with the associated compression stresses). The tensile stresses may induce intermediate formation of nanosized cracks within the thin Al layer on the $\beta$-AlLi surface and the resultant (crack-separated) nanosized islands. Such islands may transform into Al(EtO)$_3$ and serve as stable nuclei for further small wire growth. The anisotropic swelling of the islands during this chemical transformation reaction by promoting vertical expansion while suppressing lateral expansion may take place when there is the formation of a sharp boundary between the transformed (expanded) and untransformed amorphous segment. In order to minimize strain energy at the Al/Al(EtO)$_3$ interface, the transformation-induced strain may be directed normal to this interface. As the $\beta$-AlLi de-lithiation and transformation of Al→Al(EtO)$_3$ proceeds the strain energy minimization leads to the Al(EtO)$_3$ expansion in the vertical direction, leading to the formation of Al(EtO)$_3$ small wires. FIG. 8A shows a schematic of the proposed formation mechanism and FIG. 8B illustrates details of the morphological evolution of a β-AlLi—Al surface region into Al(EtO)$_3$ small wires via strain energy minimization at the reaction boundary. The large pores between the individual wires assist with EtOH diffusion towards the unreacted β-AlLi surface and increase the rate of the out-diffusion of Li$^+$ and the reaction products, H$_2$ and LiEtO. Because of the significant (approximately 600%) overall volume increase upon transformation of β-AlLi alloy into Al(EtO)$_3$, the particles increase in diameter.

Other metalorganic (organometallic) and metallic small wires may form according to a similar mechanism.

Formation and size of both the Al and Al alkoxide nuclei in the example above depends on the interplay between the strain energy release upon the crack formation and increase in the interfacial energy. As such, the morphology of the Al alkoxide surface layer may be influenced by the alcohol composition.

Figures 9A, 9B:
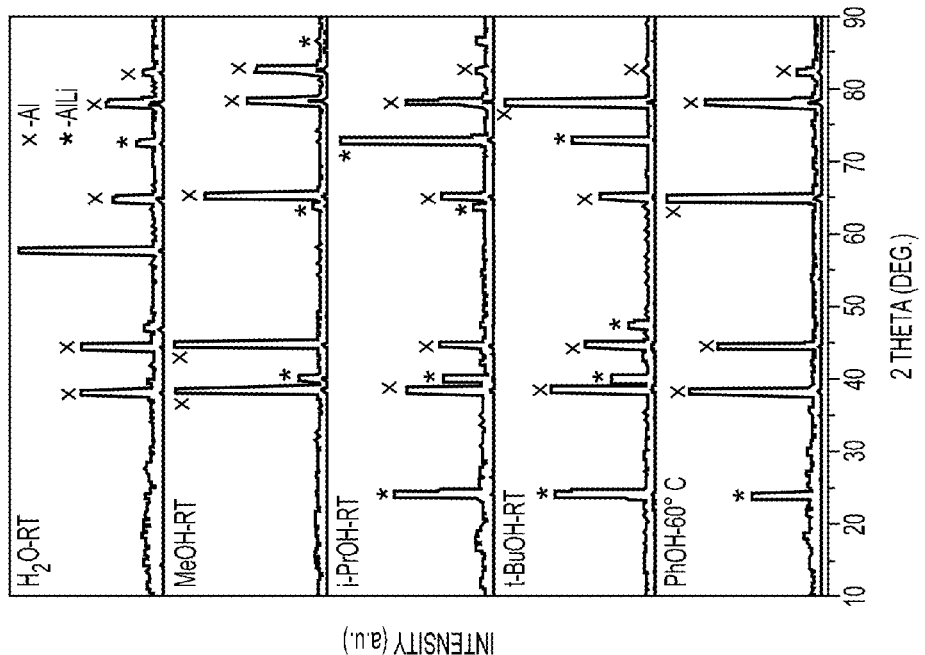

FIGS. 9A-9B show a table and XRD patterns with examples of the formation of different (nano)structures upon exposure of β-AlLi to either water or different alcohols at near room temperature and at 60° C. Formations of nanowires (NW), wires, powders and porous materials were observed, depending on the solvent composition and temperature. Because the mobility of Al$^{3+}$ ions and Al alkoxide molecules increase at higher temperature, the size of the nuclei and the resultant wire diameter may be temperature-dependent. Exposure of β-AlLi alloy to larger molecular weight alcohols (such as i-PrOH, t-BuOH, PhOH, 1-BuOH, 1-HxOH, 1-OXOH, EG, and others) at atmospheric pressure at room temperature typically resulted in the passivation of the surface layer and the formation of porous aluminum with varying degrees of residual β-AlLi. At room temperature, exposure of β-AlLi to dry methanol also resulted in the formation of a passivating layer. At 60° C., EtOH, MeOH, i-PrOH, and t-BuOH yielded Al alkoxides, while larger i-PrOH and other solvents yielded formation of porous aluminum with varying degrees of residual β-AlLi.

Figure 10B:
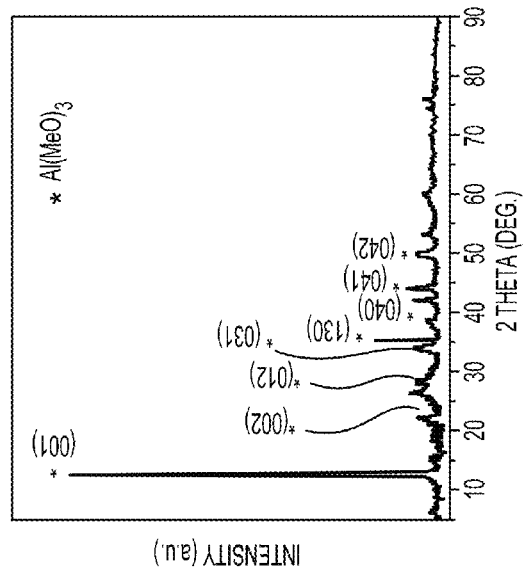
Figure 10A:
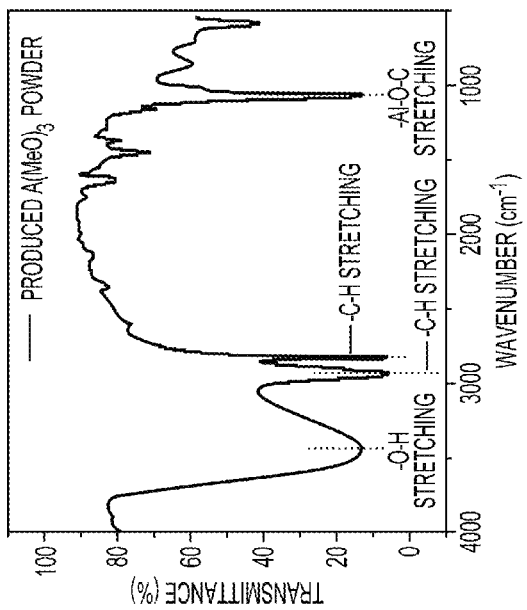
Figure 10C:
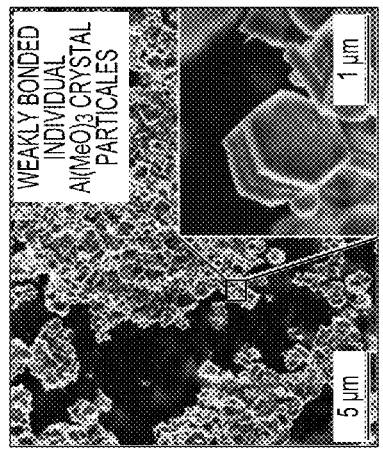

FIGS. 10A-10C show example aspects of the methoxide Al(MeO)$_3$ structures produced upon exposure of β-AlLi to smaller (compared to ethanol) methanol molecules at 60° C. This may be related to the prevention of nano-island (nuclei) formation in the surface layer due to faster reaction of delithiated Al with smaller methanol molecules and thus reduced fracture-inducing surface tensile stresses. Interestingly, the Al methoxide (Al(MeO)$_3$) sample may typically be in the form of a crystalline powder at such conditions, while the Al(EtO)$_3$, Al isopropoxide (Al(i-Pro)$_3$), and Al tert-butoxide (Al(tBuO)$_3$) formed nanowires. The high degree of crystallinity in Al(MeO)$_3$ produced at 60° C. may result in the formation of cracks or openings at grain boundaries and prevent the surface passivation. The lack of Al(MeO)$_3$ nanowires in this experiment may be related to their pulverization due to insufficiently high ductility and elasticity of Al(MeO)$_3$ required to accommodate chemical transformation-induced interface stresses of the relatively large (up to approximately 1 μm) diameter crystals.

Figure 11A:
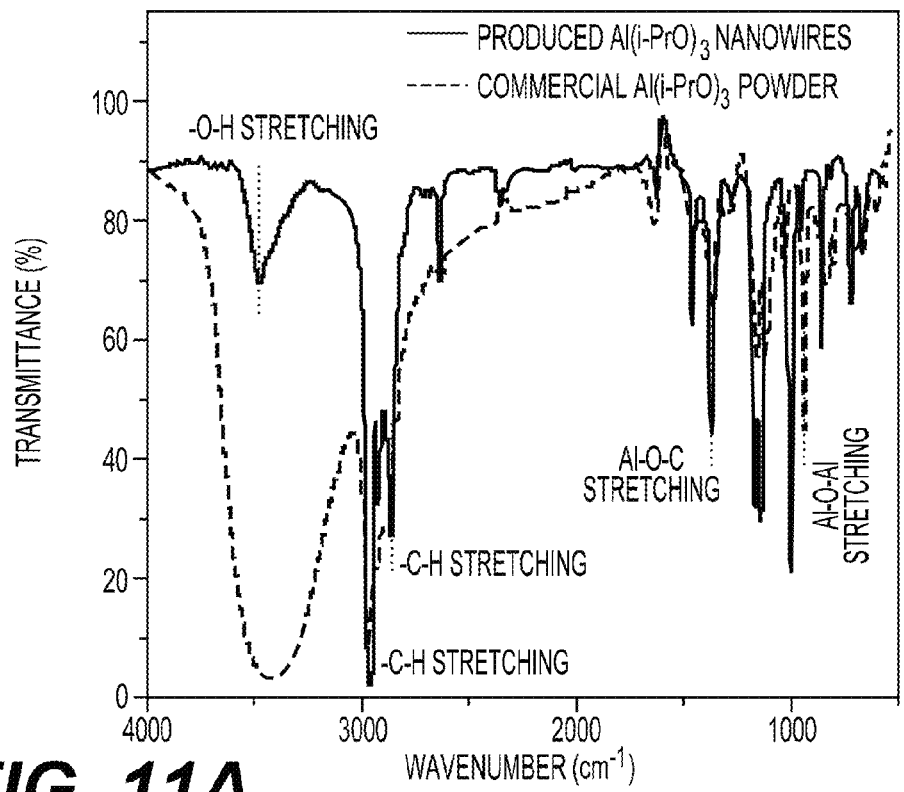
Figure 11B:
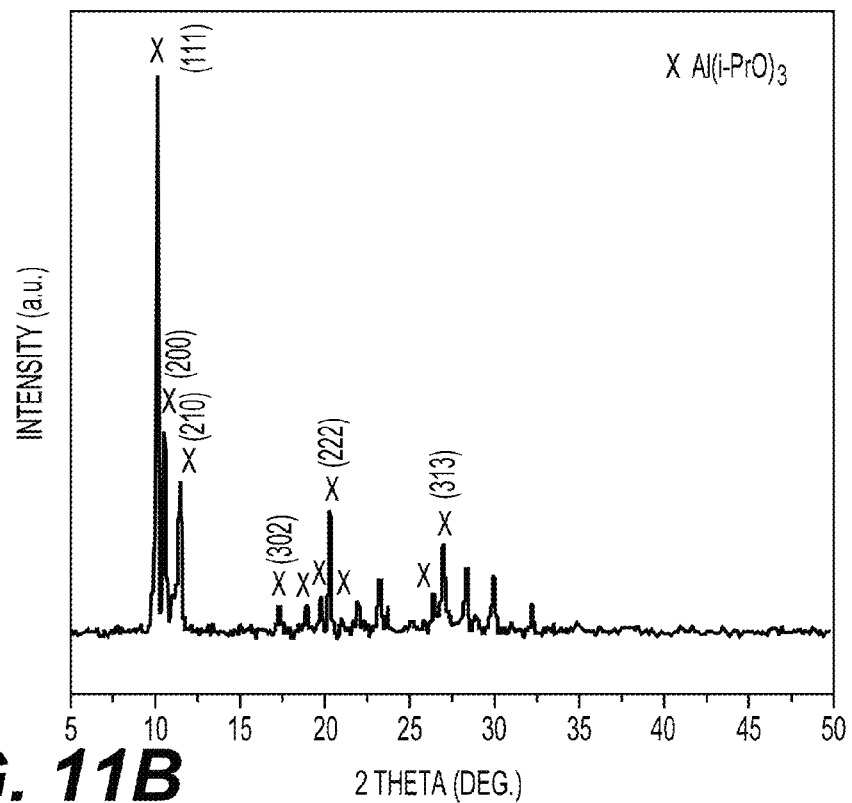

FIGS. 11A-11C show example aspects of the Al isopropoxide (Al(i-pro)$_3$) structures produced upon exposure of β-AlLi to dry isopropanol at atmospheric pressure at 60° C. The higher temperature allowed reaction of delithiated Al with larger isopropanol molecules, which successfully converted to 1D Al(i-PrO)$_3$ nanostructures of approximately 1.1 μm diameter. Faster diffusion of still moderately sized isopropanol molecules may have allowed this transformation reaction to proceed. In spite of the relatively large diameter of Al(i-PrO)$_3$ 1D structures, they did not pulverize into smaller crystals. This may be related to (i) partial dissolution of Al(i-PrO)$_3$ into i-PrOH (due to its significantly higher solubility in alcohols compared to that of Al(MeO)$_3$ and Al(EtO)$_3$) and associated accommodation of the interface stresses by the dissolution-induced pores, to (ii) different growth direction and smoother surface (and thus reduced probability of surface crack formation and propagation), or to (iii) their slower reaction rate when compared to that of Al(MeO)$_3$ (and thus lower stress-loading rate, which should lead to higher fracture toughness). Increasing temperature from 20 to 60° C. approximately doubled the average diameter of the Al(EtO)$_3$ nanowires from 41 to 78 nm. These analyses demonstrate the flexibility of the disclosed approach to produce 1D nanostructures of tunable diameter. The discovered formation of small wires and other nanostructures via an interplay of the surface tensile stresses upon the dissolution of one of the alloy components and strain energy minimization at the chemical transformation reaction boundary may be applicable for a broad range of chemistries, thus providing a new methodology for the low-cost synthesis of 1D (nano)materials and porous materials.

Figure 12B:
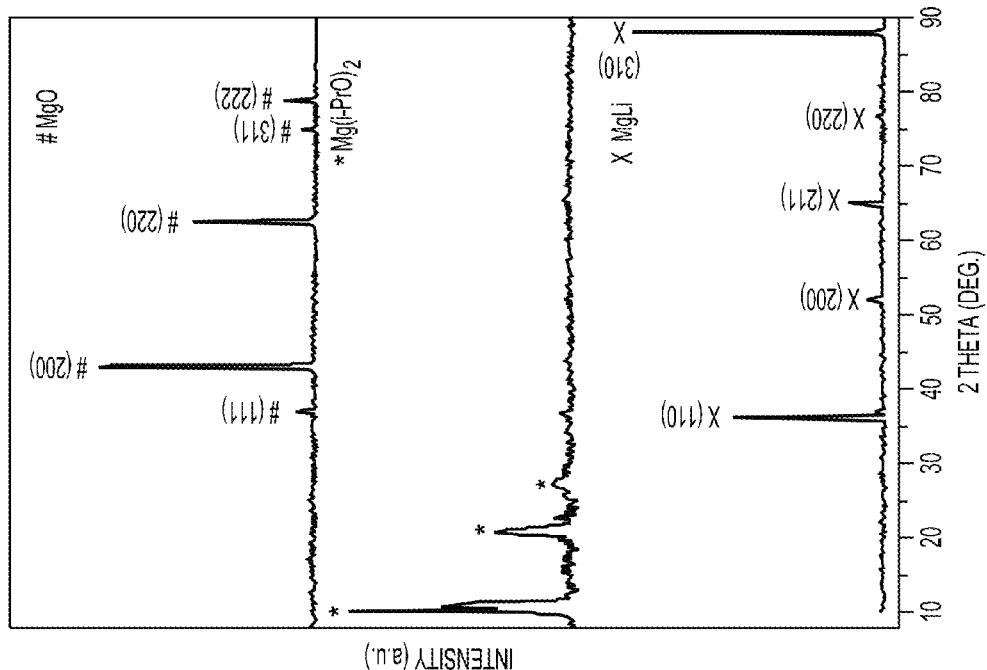
Figure 12A:
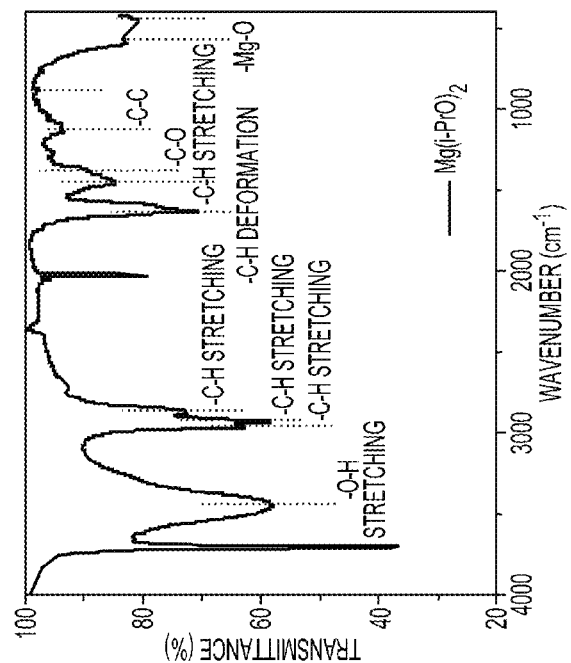
Figure 12C:
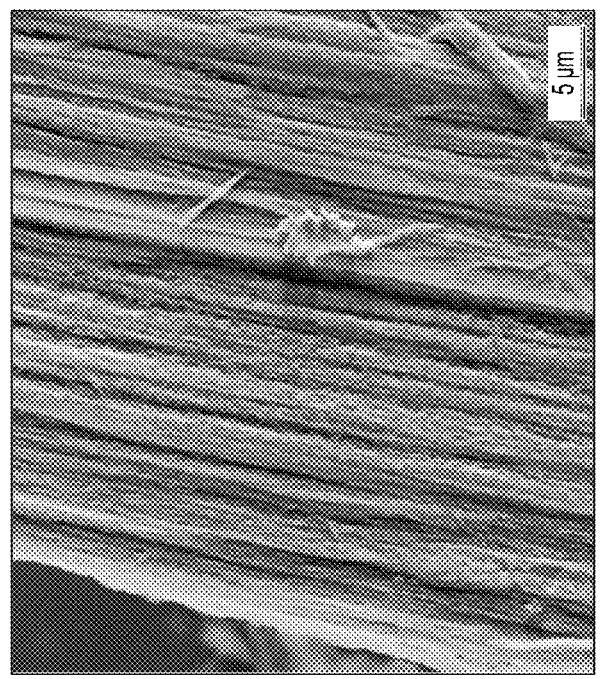

FIGS. 12A-12C show example aspects of the formation of Mg(i-PrO)$_2$ wires produced by exposing bulk MgLi alloy to i-PrOH. Reactivity and solubility of Li in i-PrOH is significantly higher than that of Mg (even though both are somewhat reactive), which leads to the selective dissolution of Li (in the form of Li isopropoxide) and the formation of Mg isopropoxide nanostructures at atmospheric pressure. Similar to the above-discussed results, heating Mg(i-PrO)$_2$ in air converts it to MgO.

In some aspects of the present disclosure, it may be advantageous to deposit a layer of another material on the surface of the metal, metal alkoxide, metal hydroxide, metal oxyhydroxide, metal oxide, and ceramic small wires or porous metal, porous metal alkoxide, porous metal hydroxide, porous metal oxihydroxide, porous metal oxide, porous ceramic and other porous materials. This may be for a desired modification of mechanical properties, modification of electrical or dielectric properties, modification of interfacial properties (such as interfacial energy, strength, wetting angle, tribological properties, etc.) (e.g., if used in composites), modification of optical properties, protection against undesirable actions of the outside environment, enabling enhanced chemical reaction rates (e.g., for catalysis), and other reasons. The suitable surface layer thickness may range from as thin as sub-monolayer (discontinuous monolayer, typically 0.01-0.2 nm in average thickness) to as thick as 1,000 nm. However, an average layer thickness ranging from around 0.3 nm to around 30 nm has been found to work well for many applications.

Depending on the applications of the produced metal, alkoxide, hydroxide, oxihydroxide, oxide, and ceramic small wires (or porous materials), the layer may be a metal, polymer, carbon, dielectric, or ceramic material. Examples of suitable ceramic surface layers include, but are not limited to, various oxides, various chalcogenides (e.g., sulfides) and oxi-chalcogenides, various halides (e.g., fluorides) and oxi-halides, various nitrides and oxi-nitrides, various carbides and oxi-carbides, various borides, their mixtures, and others. In some applications, it may also be advantageous to form a composite surface layer coating. In some applications, it may also be advantageous to form a porous coating layer.

The pores in the coating layer may be filled with another functional material. In some applications, the coating layer may leave closed pores within the porous alkoxide, hydroxide, oxihydroxide, and oxide materials (e.g., small wires). In some applications, these closed pores may be filled (pre-filled) with another functional material. In some applications, the pores may also be open.

In some applications, it may be advantageous to put two or more layers of materials as a coating. These layers may have different composition, density, porosity, surface chemistry, mechanical or electrical or optical properties, or other substantial differences. For example, if the inner alkoxide, hydroxide, oxihydroxide and oxide materials (e.g., small wires) have internal porosity, the inner layer of the coating may have smaller pores and the outer layer of the coating may have no pores.

Different methods may be suitable for the formation of surface layers on alkoxide, hydroxide, oxihydroxide, and oxide materials (e.g., small wires or porous materials). These include, but are not limited to: conversion and deposition reactions conducted in gaseous or liquid environments and their combinations. Examples of suitable deposition methods in a gaseous phase include, but are not limited to, various types of chemical vapor deposition (CVD) (including plasma enhanced deposition), atomic layer deposition (ALD), molecular beam epitaxy (MBE), physical vapor deposition (PVD, such as sputtering, pulsed laser deposition, thermal evaporation, etc.), and their various combinations. CVD and ALD may be preferable in some applications requiring more conformal and more uniform (yet relatively economical) deposition. Examples of suitable liquid phase depositions include, but are not limited to: electrodeposition, plating, electrophoretic deposition, layer-by-layer deposition, sol-gel, chemical solution deposition or chemical bath deposition (CSD or CBD), and others.

FIGS. 13-15 and 17 show example processes for the manufacturing of the disclosed small wires and selected functional materials from the disclosed small wires.

Figure 13:
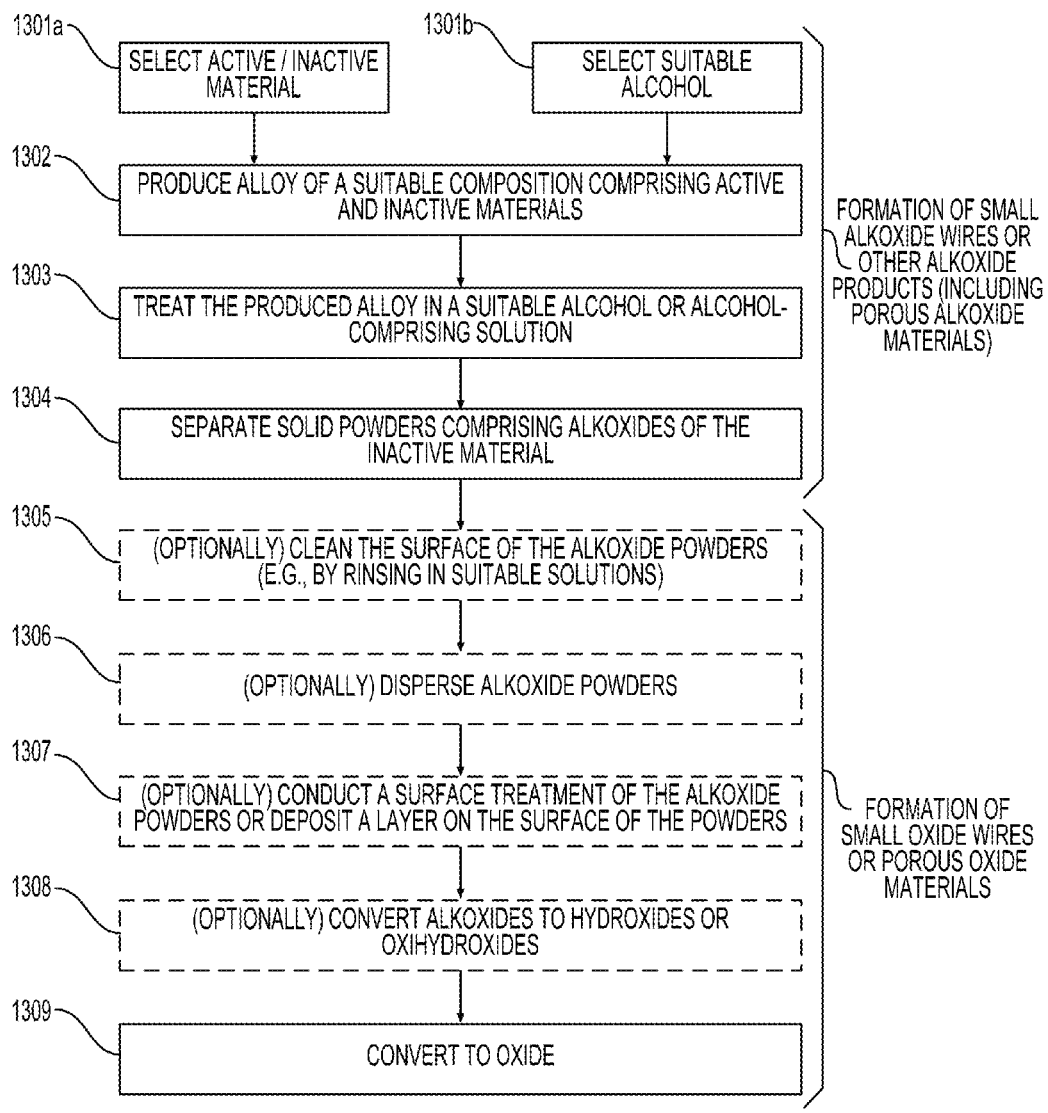
FIGS. 13-17 illustrate example methods and modifications of alkoxide and oxide nanowires (small wires) and porous oxide materials.

FIG. 13 shows an example process for the formation of alkoxides, such as aluminum alkoxides, as an example organometallic (or metalorganic) compound among others (including alkoxides having the shape of small wires). Active (in terms of its high reactivity with a selected alcohol) and inactive (in terms of its very low reactivity with a selected alcohol) materials are selected (block 1301a) along with a suitable alcohol (block 1301b). Such materials are then formed or otherwise produced into an alloy of a suitable composition (typically with the atomic fraction of active materials being greater than around 40%) (e.g., by heat treatment (e.g., using an inductive furnace), chemo-mechanical fusion, electrochemical alloying, or by other methods) (block 1302). It will be appreciated that "providing" or "producing" the alloy as used herein may encompass not only active processing steps, but also generally any method of procuring the alloy, including obtaining it from a third party and so on. The produced alloy is then subjected to treatment in a selected alcohol or a suitable alcohol-comprising solution in order to produce solid alkoxides of the inactive material (block 1303). Preferably, alkoxides of the active material are simultaneously dissolved in the alcohol or a suitable alcohol-containing solution. The solution may preferably have nearly no reactivity with the produced alkoxides of the inactive materials and may preferably not dissolve the produced alkoxides of the inactive materials. The solid alkoxides of the inactive material (e.g., in the form of small wires) may then be separated from the solution (e.g., by filtering, centrifugation, decanting, or other methods) (block 1304). The surface of the produced alkoxides may optionally be cleaned (e.g., by washing in alcohol(s) or other non-reactive solvents) (optional block 1305) and optionally dispersed in a solvent (optional block 1306). If a surfactant is used for the dispersion step, it may be important that it does not destroy the alkoxides by a chemical reaction (chemical attack). If a sonication is used for this dispersion step, it may also be important to use sufficiently low power to prevent undesirable breaking of the alkoxide particles (small wires). In addition to the alkoxide formation, a similar method may be utilized for the formation of other metalorganic structures as well as metal structures (such as porous and small wire-shaped structures), depending on the solvent chemistry and environmental conditions. The surface of the formed (e.g., alkoxide) particles (small wires) or porous structures may be optionally chemically modified or coated with a functional layer of suitable thickness and composition (depending on the application) (optional block 1307). The alkoxide particles (small wires) or porous structures may be optionally transformed to hydroxides and oxihydroxides (optional block 1308) prior to their final conversion to oxide small wires or porous oxide materials (block 1309). As discussed above, the conversion (block 1309) to oxide may proceed by heating of the precursor small wires in an oxygen containing gas (such as air). In addition to the oxide formation, other ceramic small wires may be produced by utilizing other reactive gases (e.g., halogen-containing or nitrogen-containing, to provide a few examples) or reactive solutions. For treatment in a gaseous environment, plasma may be effectively utilized to increase the conversion rate (particularly at lower temperatures).

Figure 14:
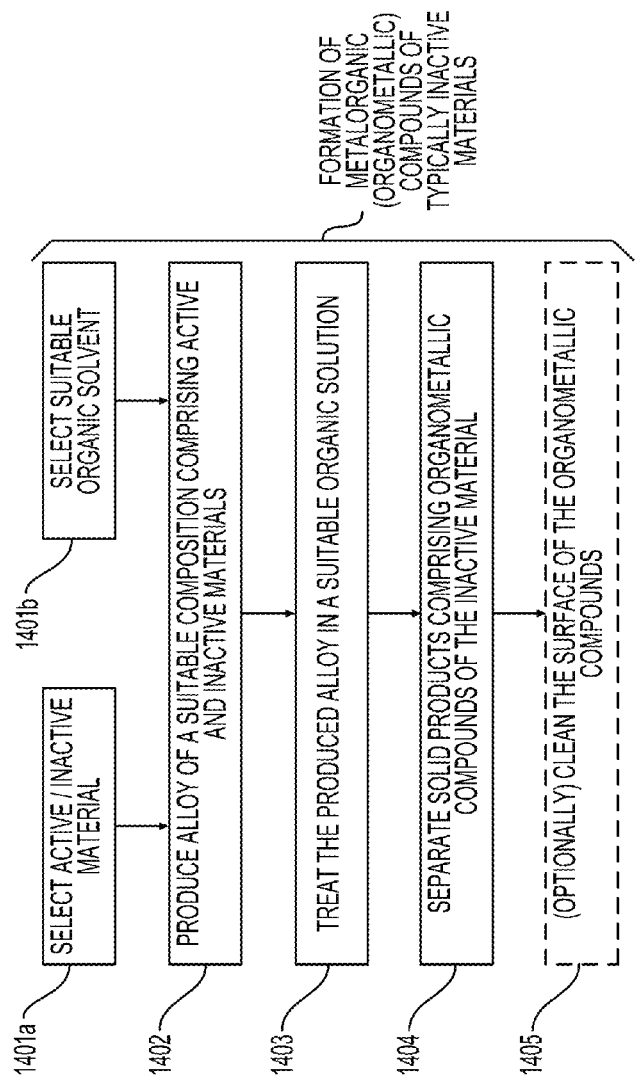

FIG. 14 shows an example process for the formation of a broad class of organometallic (or metalorganic) compounds comprising metals that typically exhibit very low reactivity with the corresponding organic species (ligands). Active (in terms of its high reactivity with a selected organic compound) and inactive (in terms of its very low reactivity with a selected organic compound) materials are selected (block 1401a) along with a suitable organic solvent/compound (block 1401b), and then formed or otherwise produced into an alloy of a suitable composition (typically with the atomic fraction of active materials being greater than around 40%) (block 1402). It will again be appreciated that "providing" or "producing" the alloy as used herein may encompass not only active processing steps, but also generally any method of procuring the alloy, including obtaining it from a third party and so on. The produced alloy is then subjected to treatment in the selected organic compound or a suitable solution comprising the desired organic compound in order to produce solid metalorganic (or organometallic) compounds of the inactive material (block 1403). Preferably, metalorganic (or organometallic) compound(s) of the active material are simultaneously dissolved in the solution. The solution may preferably have nearly no reactivity with the produced metalorganic (or organometallic) compound(s) of the inactive materials and may preferably not dissolve the produced metalorganic compound(s) of the inactive materials. The solid metalorganic (or organometallic) compound(s) comprising the inactive material may then be separated from the solution (block 1404). The surface of the produced metalorganic (or organometallic) compound(s) may optionally be cleaned (e.g., by washing in alcohol(s) or other non-reactive solvents) (optional block 1405).

As discussed above, instead of using organic solvents as shown in FIG. 14, one may also use water or aqueous solution (of various pH and composition (typically in the pH range from around 4 to around 14), including those that comprise metal salts, metal bases or acids) for the selective (preferential) dissolution of one (or more) (more reactive) components of the metal alloys and relatively fast formation of nanostructures (e.g., small wires, porous small wires, other porous structures, particles of controlled dimensions, etc.) comprising less reactive metals. Depending on the alloy composition and pH, one may produce useful nanostructures (e.g., small wires, porous structures, particles of controlled dimensions, etc.) of metals, metal hydroxides, metal oxyhydroxides, metal oxides, and other metal-comprising species. Higher pH and higher nobility of the less reactive metals in the alloys (of the more reactive and less reactive metals) may typically favor formation of metallic compounds. Examples of more noble metals suitable for the formation of nanostructured metallic compounds include, but are not limited to, palladium, platinum, gold, silver, titanium, copper, lead, molybdenum, uranium, niobium, tungsten, tin, tantalum, chromium, nickel, and their various alloys. In some designs, the produced small wires may be porous.

In some designs, it may be advantageous to utilize alloys (of more reactive and less reactive metals) in the form of the wires of well-defined dimensions, various porous structures of the desired pore size (e.g., a mesh or a foam) or particles of well-defined size and shape (e.g., spherical particles or wire-shaped particles) prior to the selective dissolution procedure. The size (e.g., diameter) of such particles may range from around 0.1 microns to around 10,000 microns, depending on the application. This method may allow formation of nanostructured or porous particles of less reactive metal (or less reactive metal compounds) with hierarchical morphology and additional control of their structure, dimensions, and properties.

Formation of porous nanostructures (including flexible porous structures, such as flexible membranes) comprising metal or ceramic compositions may be particularly attractive for some applications.

Figure 15:
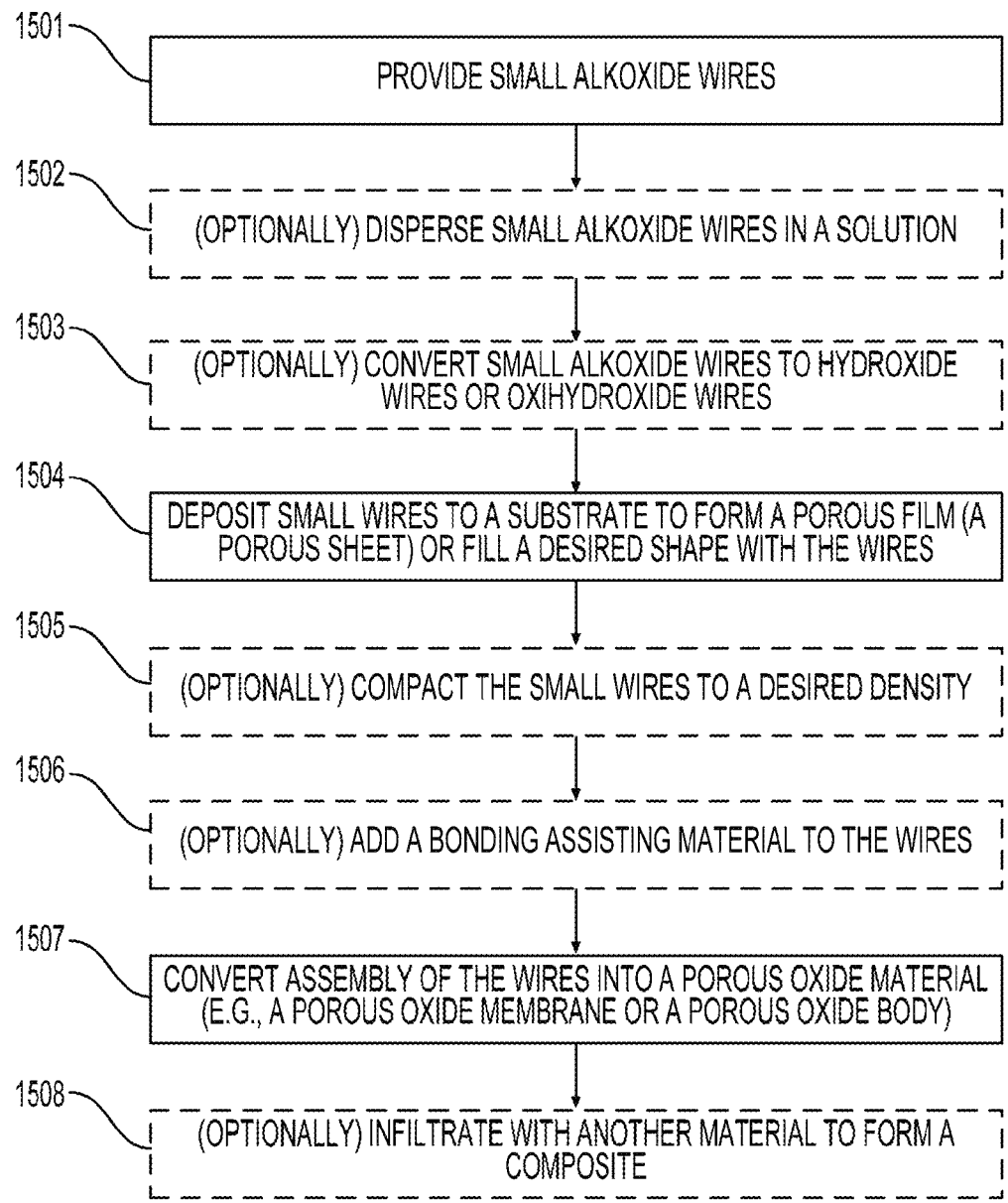

FIG. 15 shows an example process for the formation of porous oxide membrane(s) or porous oxide bodies of the desired shape. The process starts with providing alkoxide small wires (block 1501), which may be synthesized according to part of the process described in FIG. 13 (blocks 1301-1304). These small wires may be optionally dispersed (optional block 1502), optionally converted to hydroxide or oxihydroxide small wires (optional block 1503) and deposited on a substrate to form a (e.g., non-woven) film or a sheet (somewhat similar to a paper formation process except that cellulose fibers are replaced here with alkoxide small wires) (block 1504). In some applications, one may introduce a charge on the surface of the small wires and collect such small wires by application of an electric field (e.g., by applying an opposite potential to a substrate to attract these small wires). A field-assisted deposition may proceed in either liquid (when small wires are dispersed in a liquid) or in gaseous phases (when small wires are carried with the flow of gas), or by a hybrid technique (e.g., by electrospray deposition) or by combination(s) of these and other techniques. Small wires may also be deposited by using a spray deposition method, by electrophoretic deposition, by voltage assisted deposition from gaseous suspension or liquid or aerosol suspension, by casting from a liquid suspension, by layer-by-layer deposition, or by dip coating, to name a few suitable methods. Porosity may be further enhanced in such small wire-based membranes when small wires are deposited together with another sacrificial material (e.g., a salt, a polymer, or a suitable oxide, etc.) to form a membrane sample of the desired dimensions when this sacrificial material is at least partially removed (e.g., by dissolution, etching, oxidation, or other suitable methods). In some cases, stretching may also be utilized for a porosity enhancement. In some applications that require formation of bulk (as opposed to thin (e.g., 10 nm-0.5 mm) membranes or sheets) porous oxides, the small wires may be formed into a body of the desired shape (e.g., by using a mold filled with such small wires) (block 1504). In order to increase the density of the deposited small wires, they may be deposited in an aligned form. A flow of the small wire suspension may be used to orient such small wires prior (or during) the deposition. Alternatively, an electric field may be used for small wire orientation. Deposited small wires may also be optionally compacted (compressed) to a desired density (optional block 1505). In some cases, it may be advantageous to add another material (e.g., one that would assist bonding of the individual small wires) to the assembly of small wires (optional block 1506). Such a material may be a polymer, a salt, or an oxide precursor (e.g., hydroxide or oxihydroxide) and may comprise the same metal as the small wires. Such a material may be sprayed into the sheet, for example, by using jets of air or a compatible gas or liquid to provide better structural properties to the film. In some cases, this material may be deposited in the form of the fibers. The final step may involve transformation of the deposited small wires to a porous flexible oxide membrane or a porous bulk body, composed of the oxide small wires bonded together (either by chemical or physical bonds) (block 1507). As described above, treatment in oxygen-containing gas (e.g., in air) may be utilized for such a transformation. In some designs, instead of formation of oxide (block 1507), an oxy-halide (e.g., oxy-fluoride) or halide (e.g., fluoride) or other flexible ceramic membrane or porous body may be formed. In some designs, conversion to oxide or another ceramic material may be conducted in plasma. The pores in the produced porous oxide material (e.g., aluminum oxide) or porous ceramic material (e.g., aluminum oxy-fluoride or aluminum fluoride or oxyfluoride or fluoride of another metal or carbide, etc.) may be optionally partially or completely infiltrated with another material (e.g., polymer, metal, ceramic, glass, composite, functional particles, etc.) to form a composite with the desired properties (optional block 1508). The surface of the small wires (before or after conversion to oxide or another ceramic material) may be optionally coated (pre-coated) with a surface layer. In some designs, plasma or heat-treatment in a controlled environment may be involved in the surface layer formation. The suitable mass and volume fractions of the small wires in such composites depend on the particular application, desired properties, and compaction of the small wires. This typically ranges from around 0.0001 vol. % (and around 0.001 wt. %) to around 90 vol. % (and around 90 wt. %).

Figure 16:
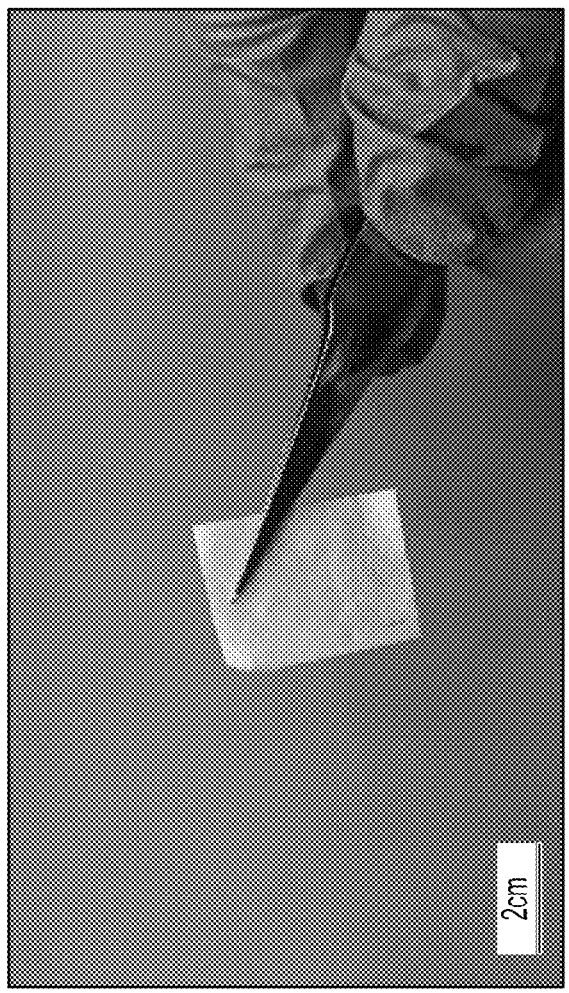

FIG. 16 shows an example of a porous $Al_2O_3$ membrane produced according to the process illustrated in FIG. 15, where small Al ethoxide wires are first produced according to the process illustrated in FIG. 13. These small Al ethoxide wires were first dispersed in an ethanol solution and deposited on a polytetrafluoroethylene (PTFE) substrate by casting to form a porous sheet. By heating this sample in dry air at elevated temperatures (more specifically, by heating in air from room temperature to 800° C. at a rate of 5° C./min, holding at 800° C. for 2 hours, and cooling to room temperature), a flexible porous $Al_2O_3$ membrane was obtained.

In some applications, it may be advantageous for the porous oxide (or porous ceramic) material to be composed of individual layers. It may also be advantageous to exhibit a horizontal (or vertical) alignment of the small wires within an individual layer. In some applications, it may be advantageous for the horizontally aligned small wires to have a different orientation in the subsequent layers (e.g., with an angle anywhere between 0 and 90 degrees in the neighboring layers). Controlling orientation of individual layers provides opportunities to tailor the mechanical properties of the composites in multiple directions and have a different resistance to fracture and tunable bending modulus.

Figure 17:
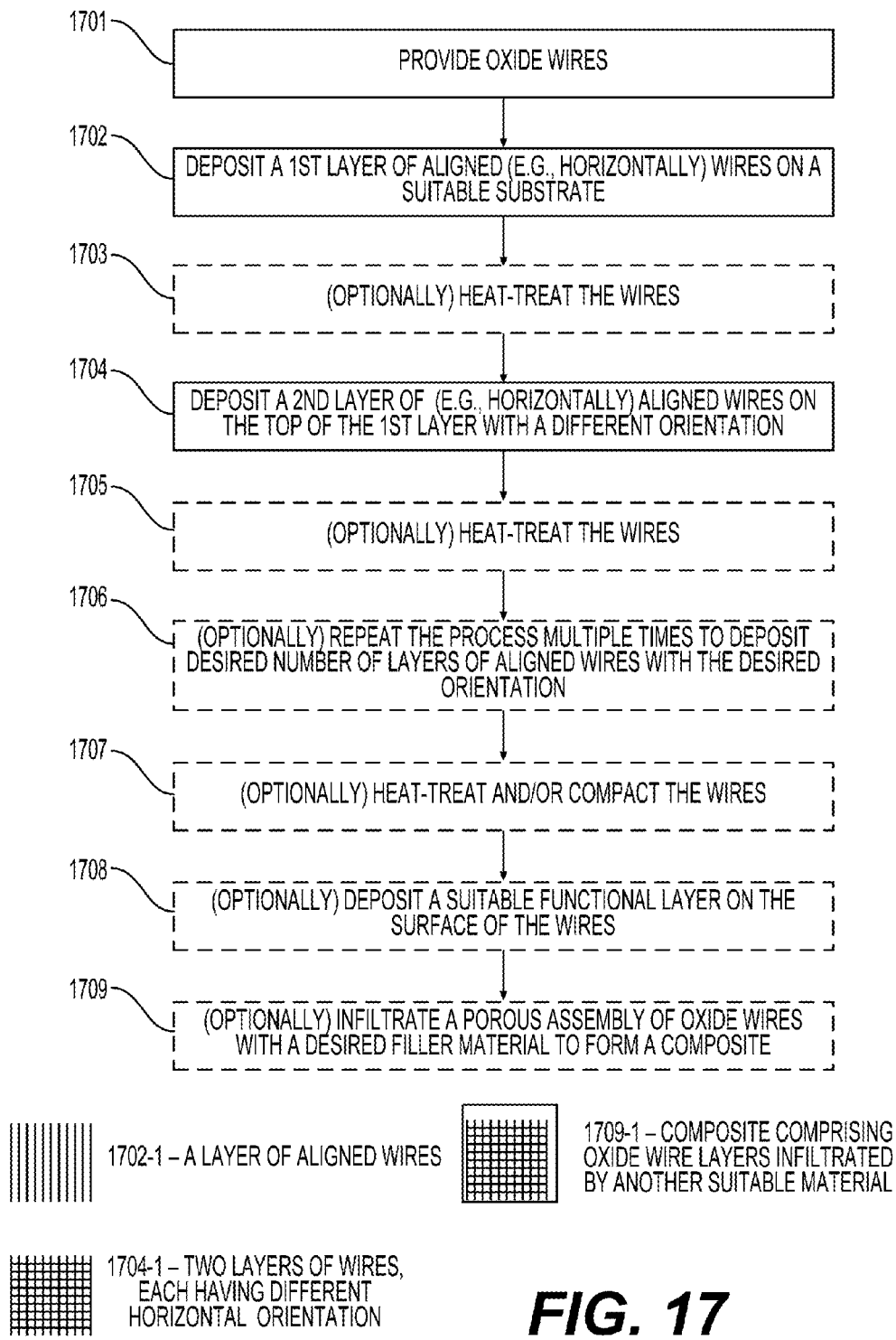

FIG. 17 shows an example process for the formation of a multi-layered porous membrane or a composite comprising a multi-layered porous membrane. Within individual layers, the small wires may be aligned along certain directions or be misaligned. This example process involves providing oxide (or other ceramic) or metallic small wires (block 1701), which may be produced, for example, as described in FIG. 13. These small wires may be deposited on a substrate aligned along the desired direction (block 1702) (e.g., forming a pattern 1702-1, shown schematically as parallel lines). After an optional heat-treatment (optional block 1703) and optional compaction of the small wires in this layer, a second layer of aligned small wires may be deposited on the top of the first layer (block 1704) (e.g., forming a pattern 1704-1, shown schematically as intersecting lines), and the whole assembly may also be further optionally heat-treated (optional block 1705) and optionally compacted. The deposition of individual layers of aligned (or misaligned) small wires may be repeated multiple times until the desired thickness and the desired number of layers is obtained (optional block 1706). After optional heat treatment (optional block 1707), optional compaction, and optional deposition of the functional surface coating(s) (optional block 1708), the multi-layered assembly of small wires may optionally be partially or fully infiltrated with another material (e.g., polymer, metal, ceramic, glass, composite, functional particles, etc.) to form a composite with the desired properties (optional block 1709) (e.g., forming a pattern 1709-1, shown schematically as filled intersecting lines). Such a composite may be flexible, have enhanced mechanical or desired optical properties, or other attractive features. The suitable mass and volume fractions of the small wires in such composites will depend on the particular application, desired properties, and compaction of the small wires. This typically ranges from around 0.0001 vol. % (and around 0.001 wt. %) to around 90 vol. % (and around 90 wt. %).

Other aspects of the present disclosure include the use of oxide (or other ceramic) small wires and porous oxide (or other porous ceramic) materials in several applications. Such uses may provide unique benefits of achieving attractive (and sometimes remarkable) properties at a low cost.

One aspect of the present disclosure includes the use of aluminum oxide (and other oxide as well as other ceramic) small wires (particularly those described herein, including but not limited to porous aluminum oxide small wires) in biocompatible materials. In this case, the utilization of such small wires may favorably enhance chemical, biological, physical, and structural (mechanical) properties, allow control over permeation (of species of interest), control density and/or enhance compatibility with the surrounding host tissues. Depending on the particular application, mechanical properties of interest may include: higher elastic modulus, higher strength, higher hardness, higher wear resistance, higher stiffness, higher toughness, or optimal load transmission. Example applications may include, but are not limited to, composites for (i) external fixators, bone plates, and screws (including those that comprise epoxide, poly(methyl methacrylate), polypropylene, polyethylene, PS, nylon, polybutylterephthalate, polyether ether ketone, and other polymers or titanium, various titanium alloys (e.g., titanium aluminum, titanium aluminum vanadium, titanium aluminum niobium, titanium molybdenum, gold, biocompatible stainless steel (e.g., 316LL), cobalt-chromium-molybdenum alloys, or other biocompatible metals and/or carbon); (ii) joint replacement (including those that comprise examples of polymers, metals, and carbon above); (iii) total hip replacement; (iv) bone cement; (v) dental applications; (vi) catheters; and (vii) prosthetic limbs, to name a few. In addition, the described aluminum oxide nano small wires may be advantageously utilized in superparamagnetic nanocomposites for biology, medicine, diagnostics, and therapy. The suitable volume fraction of small wires in biomaterial composites may range from around 0.05 vol. % to around 70 vol. %.

In some applications (e.g., transparent armor, screens, windshields, displays, among others), the use of aluminum oxide (and other oxide and other optically transparent ceramic) small wires (particularly those described herein) as fillers in optically transparent glasses and glass coatings may be highly advantageous in terms of tuning glass optical properties, increasing glass hardness, wear resistance, scratch resistance, fracture toughness, manufacturability in thin sheet states, and other important properties. When small wires are small in dimensions (e.g., below around 50-100 nm in diameter) and uniformly distributed within a glass, scattering of visible light might be avoided even if the glass matrix exhibits a substantially different refractive index because optical non-uniformities may be sufficiently below half of the visible light wavelengths. However, if optical non-uniformities are larger than around 100 nm, matching the refractive index of the small wires with that of glass may be important to maximize transparency of the small wire-glass composites. This may be accomplished either by tuning the refractive index of a glass or by tuning the refractive index of the small wires. For example, if small wires are composed of 100% solid $Al_2O_3$ small wires with no closed pores they would typically exhibit a refractive index of around n=1.75-1.81 (for visible light). As such, selecting a glass (ceramic) that approximately (preferably within 4% or less; more preferably within 2% or less; or even more preferably within 1% or less) matches its refractive index n may be advantageous for maximizing transparency of the $Al_2O_3$ small wire/glass composites. Illustrative examples of such glasses with matching refractive index may include, but are not limited to, various flint glasses, beryllium oxides, magnesium oxides, various suitable mixtures of oxides comprising at least two (preferably at least three; or even more preferably at least four) of the following oxides: boron oxide, barium oxide, beryllium oxides, bismuth oxide, magnesium oxides, calcium oxide, cesium oxide, rubidium oxide, potassium oxide, aluminum oxide, lanthanum oxide, cerium oxide, lithium oxide, magnesium oxide, manganese oxide, sodium oxide, niobium oxide, neodymium oxide, phosphorous oxide, antimony oxide, silicon oxide, germanium oxide, strontium oxide, tin oxide, titanium oxide, tantalum oxide, hafnium oxide, tungsten oxide, zinc oxide, and zirconium oxide. Examples of suitable commercial glasses include but are not limited to N-BASF64 with n=1.7, N-LAK8 with n=1.72, N-SF18 with n=1.72, N-SF10 with n=1.73, S-TIH13 with n=1.74, N-SF11 with n=1.78, N-SF56 with n=1.78, N-LASF44 with n=1.8, N-SF6 with n=1.81, N-SF57 with n=1.85, N-LASF9 with n=1.85, and many others). In another embodiment, for a given refractive index of a glass (e.g., aluminosilicate-type glass) of, for example, 1.52, a closed internal porosity of porous $Al_2O_3$ small wires may be tuned in order to achieve a matching refractive index (preferably within 4% or less; more preferably within 2% or less; or even more preferably within 1% or less). By increasing the closed pore volume within porous $Al_2O_3$ small wires, one may reduce their effective refractive index from around n=1.75-1.81 to below 1.3, in some applications. In some applications, optically transparent polymers (e.g., particularly those that exhibit a high refractive index, such as polycarbonate, trivex, crown glass, etc.) may be utilized instead of oxide glasses or optically transparent ceramic materials as matrix materials in $Al_2O_3$ small wire-comprising composites. Porous oxide particles (not only $Al_2O_3$) with matching effective refractive index may also be used in optically transparent polymer-oxide composites that exhibit more favorable mechanical properties and scratch resistance than pure polymers. In some applications of transparent materials with enhanced toughness and scratch resistance, polymer small wire, glass small wire, and ceramic small wire composites may be manufactured by first producing a porous scaffold (including both bulk parts of various shapes and sizes and porous sheets or thin membranes) composed of the small wire material that is then infiltrated with a matrix material (such as a suitable polymer, oxide glass, transparent ceramic, etc.). The suitable mass and volume fractions of the small wires in such wire-glass composites typically ranges from around 0.01 vol. % (and around 0.01 wt. %) to around 85 vol. % (and around 85 wt. %).

Examples of suitable uses of such glass small wire composites include, but are not limited to, watches, screens/monitors of various sizes (e.g., computer monitors, cell phone screens, monitors in laptops, ultrabooks, tablets, electronic books, television screens, credit card terminals, monitors of various other electronic devices or components of devices, etc.), various optical lenses (including those used in glasses, cameras, microscopes, spectroscopes and other research tools, etc.), sensors, window glasses, various applications in automotive and transport (windscreens/windshields, backlights, light-weight but reinforced structural components of cars, aircrafts, ships, etc.), various appliances (oven doors, cook tops, etc.), glass bulbs, tableware glass (e.g., drinking glasses, plates, cups, bowls, etc.), jewelry, protection equipment (transparent armor, safety screens, helmets, personal protection equipment, radiation protection screens (e.g., from X-Rays, gamma-rays, etc.)), various interior design and furniture (mirrors, partitions, balustrades, tables, shelves, lighting, etc.), various reinforcement structures, packaging, fiber optic cables, life science engineering, and electrical insulation, to name a few.

In some applications, it may be advantageous to add a particular color to otherwise transparent oxide small wire/glass composites or to the small wires themselves. In some applications, suitable dyes or quantum dots may be attached to the surface of the small wires or be infiltrated into the pores (if present in the small wires). In some applications, it may be advantageous to seal these pores in order to prevent direct contact between the dyes (or quantum dots) and surrounding environment. In some applications, the sealing material may be a glass (e.g., oxide glass, etc.) or a ceramic or a polymer.

In some applications, the use of aluminum oxide (and other oxide and other ceramic) small wires (particularly those described herein, including but not limited to porous aluminum oxide small wires) as well as aluminum oxide (and other oxide based and other ceramic based) porous membranes as fillers in polymer composites (including various polymer-ceramic, polymer-carbon, polymer-metal, polymer-ceramic-metal composites) may be advantageous for enhancing various properties (e.g., mechanical, thermal, dielectrical, etc.) of such polymer-comprising composites. The one dimensional (1D) wire geometry may be particularly advantageous for the formation of dense composites with excellent mechanical properties, flexibility, uniformity and controlled (e.g., either high, medium, or low) volume fraction of the small wires. Depending on the particular application, mechanical properties of interest (at room temperature, elevated temperatures, or low temperatures) may include, but are not limited to: higher elastic modulus, higher strength, higher hardness, higher scratch resistance, higher wear resistance, higher stiffness, higher toughness, better resistance to creep, better resistance to fatigue, and better tribological properties, to name a few. Similarly, the use of small wires as discussed above may allow achieving a desired effective dielectric constant and refractive index in small wire/polymer composites. The suitable weight fraction of the small wires in such polymer-comprising composites depends on the particular application and desired properties, but typically ranges from around 0.01 wt. % to around 95 wt. %.

In some applications, it may be advantageous to add a particular color to otherwise transparent oxide small wire/polymer composites. In some applications, suitable dyes or quantum dots may be attached to the surface of the small wires or be infiltrated into the pores (if present in the small wires). In some applications, it may be advantageous to seal these pores in order to prevent direct contact between the dyes (or quantum dots) and surrounding environment. In some applications, the sealing material may be a glass (e.g., oxide glass, etc.) or a ceramic or a polymer.

A broad range of natural, semi-synthetic, and synthetic polymers may benefit from the use of aluminum oxide small wires and other ceramic as well as metal wires (particularly those described herein). Structure-wise, these polymers may also be classified into linear polymers, branched chain polymers, and cross-linked polymers. These polymers may also be classified into various thermoplastics, thermosets (or resins), elastomers (or rubbers), and fibers (or natural polymers). Selected examples of suitable thermoplastics include, but are not limited to, polyethylene (PE), polyphenylene oxide (PPO), polyphenylene sulfide (PPS), polypropylene (PP), polyvinyl chloride (PVC), polyether sulfone (PES), polyetherether ketone (PEEK), polyetherimide (PEI), polycarbonate (PC), various polyamides (e.g., nylon), various polyesters (e.g., aliphatic polyester), acrylic (poly(methyl methacrylate), PMMA), polytetrafluoroethylene (PTFE), polybenzimidazole (PBI), polyacrylonitrile (PAN), polybuthadiene, polystyrene (PS), polyoxymethylene (POM), and co-polymers of the above polymers, among others. Selected examples of suitable thermoset polymers include, but are not limited to, various alkyds or polyester fiberglass polymers and polyester resins, various amino (urea, melamine) polymers (including urea-formaldehyde, phenol formaldehyde, melamine formaldehyde, etc.), various epoxy resins (including those after esterification and other modifications—e.g., vinyl ester), various phenolic resins (bakelite or phenol-formaldehyde (PF)), various polyimides, various silicones, various polyurethanes, polyisocyanurate (PIR), various rubbers/elastomers (vulcanized rubber, neoprene, nitrile, styrene butadiene, etc.), various heterocyclic compounds (e.g., polyhexahydrotriazine), and cyanate esters, to mention a few. Other specific examples of other suitable polymers include, but are not limited to, various (para-) aramid fibers, poly(vinyl alcohol) (PVA), various proteins and polypeptides (including enzymes), chitin (poly (N-acetylglucosamine)), silk (including spider silk) and various polysaccharides (including starch, cellulose and carboxymethyl cellulose, alginic acid and salts of alginic acid), to name a few.

Suitable methods for the synthesis of composites comprising aluminum oxide small wires (particularly those described herein, including but not limited to porous aluminum oxide small wires) and other ceramic small wires and metal small wires may include, but are not limited to: various solution mixing techniques, solution blending, melt blending, in-situ polymerization, solid-state shear pulverization, and vacuum (e.g., resin) infusion, among others. Solution blending involves dispersion of small wires in a suitable solvent, mixing with a suitable polymer (at room temperature or an elevated temperature), and recovering the composite by precipitating or casting a film or a bulk sample or by other suitable methods. A wet annealing method may be considered as a variation of the solution blending—it involves partially drying a small wire/polymer suspension on a substrate and then increasing the temperature to above the glass transition temperature rapidly to complete the drying process. Melt blending uses high temperature and high shear forces to disperse small wires in a polymer matrix. At high concentrations of small wires the viscosities of the composites may be relatively high, which should be taken into consideration (for some blending methods, too high of a viscosity may reduce efficiency of uniform mixing). In-situ polymerization involves dispersing small wires in a monomer followed by polymerizing the monomers. It is noted that functionalization of small wires may assist in improving the dispersion of the nanotubes in a monomer (and similarly in a solvent for solution mixing and in a polymer for melt blending). Strong covalent bonding may be formed between small wires (particularly if they are functionalized) and the polymer matrix (e.g., by using various condensation reactions). For example, epoxy nanocomposites produced using in-situ polymerization methods involving dispersion of small (optionally functionalized) wires in a resin followed by curing the resin with a hardener may allow formation of composites with a strongly enhanced tensile modulus and other properties even with a small mass fraction (e.g., less than 10 wt. %) of small oxide wires. In some applications, the reactive agents may be first infiltrated into the pores of the porous small wires before being subsequently polymerized. In some applications, one may utilize reduced temperatures to increase viscosity of the suspension to the level when processing effectively proceeds in the solid state. Solid-state mechano-chemical pulverization/mixing processes may be used to mix small wires with polymers. Pulverization methods may be used alone or followed by melt mixing. This may induce grafting of the polymer on the surface of the small wires, which may result in the improved dispersion, improved interfacial adhesion, improved tensile modulus, improved hardness, and other positive improvements in the mechanical properties of the small wire/polymer composites. In another suitable method, small wires may be first processed into dry porous membranes or porous solid bodies and laid into a suitable mold. The polymer (resin) is then infiltrated (infused or sucked) into the porous membranes/bodies comprising mold by applying negative pressure (e.g., vacuum). Excess resin may be removed out of the bodies by applying negative pressure (e.g., vacuum).

Small wire/polymer composite fibers may be produced by melt fiber spinning, where the composite melt may be extruded through a spinneret hole, and the extruded rod is air cooled and drawn under tension by a windup spool to produce aligned composite fibers. Electrospinning is yet another method to produce composite (nano)fibers using electrostatic forces.

Examples of suitable uses of such small wire/polymer composites include, but are not limited to, components of musical instruments or whole musical instruments (for example, violin bows, guitar pick-guards, drum shells, bagpipe chanters, cellos, violas, violins, acoustic guitars, electric guitars, guitar picks, ukuleles, etc.), bags and cases (for example, laptop cases, backpacks, purses, etc.), cases, frames and components of various electronic devices (for example, laptops, ultrabooks, tablets, servers, printers, scanners, electronic books, monitors, televisions, credit card terminals, cameras, microscopes, spectroscopes and other research tools, monitors of various other electronic devices or components of devices, etc.), audio components (for example, turntables, loudspeakers, etc.), sporting goods and sporting good components (for example, components of bicycles, kite systems, etc.), various firearms use (for example, to replace certain metal, wood, and fiberglass components, etc.), components of automotive, aerospace and aircraft, ship, and other transport devices (for example, components of cars, buses, planes, ships and boats, spacecraft, drones, including rotor blades and propellers, etc.), various legs, rods and poles (for example, tripod legs, tent poles, fishing rods, billiards cues, walking sticks, poles for high reach, such as the ones used by window cleaners and water fed poles, posts that are used in restoring root canal treated teeth, etc.), many other light and durable consumer or military items (for example, handles of knives and tools, various toys, cases for various devices, tents, etc.), clothes and components of clothes (jackets, coats, shirts, pants and tights, hats, gloves, masks, stockings, buttons, etc.), footwear and components of footwear (boots, shoes, sandals, slippers, wides, narrows, etc.), cases of watches and other wearable devices, furniture, frames of reading glasses, components of various appliances (ovens, stoves, blenders, grinders, vacuum cleaners, refrigerators, dryers, washing machines, etc.), tableware, jewelry, components of various protection equipment (safety screens, helmets, personal protection equipment, etc.), furniture and design components (chairs, mirrors, partitions, balustrades, tables, shelves, lighting), electrical insulation materials, thermal insulation materials, fire resistant materials, tires, and various protective (for example, against corrosion or chemical attack) coatings on metal or wood or ceramic parts, to provide a few examples.

In some applications, the use of aluminum oxide (and other oxide as well as other ceramic and metal) small wires (particularly those described herein) in combination with carbon small wires (carbon (nano)fibers or carbon nanotubes) or carbon platelets (graphene, exfoliated graphite, etc.) may provide even more advantages than using aluminum oxide (or other ceramic or metal) small wires (or carbon small wires/platelets/tubes) alone in various composites (such as ceramic composites, glass composites, metal composites, polymer composites, carbon composites, etc.). The utility may depend on the particular application and chemistry. For example, in some cases, carbon may provide the needed electrical conductivity to the composite, but may be hard to disperse uniformly. The addition of aluminum oxide (or other ceramic small wires) may assist in such a dispersion and additionally enhance the strength of the composite. In other cases (applications), the combination of oxide small wires and carbon may enhance thermal stability (when compared to only using carbon), enhance catalytical activity (when compared to either only carbon or only oxide), enhance the modulus of toughness, etc. In yet another case, it may be desirable to provide enhanced mechanical performance and electrical connectivity within a composite with the smallest volume fraction of small wires, but conductive carbon may undesirably induce certain side reactions (e.g., as in battery electrodes). Combining aluminum oxide (or other suitable ceramic) small wires with carbon small wires (or carbon nanotubes, graphene, etc.) may provide the desired mechanical property enhancement and sufficient conductivity to the composite, while minimizing side reactions induced by carbon.

In some applications, the use of aluminum oxide (and other oxide and other ceramic and metal) small wires and other porous materials (particularly those described herein, including but not limited to porous aluminum oxide small wires and other porous membranes and particles composed of ceramic or metal(s)) in various types of solar cells (e.g., in perovskite solar cells, in organic solar cells, tin sulfide solar cells, etc.) and light emitting diodes (e.g., in organic LEDs, perovskite LEDs, various porous LEDs including GaN-based ones, etc.) may be advantageous in terms of improving their performance characteristics and long-term stability. In some applications, catalyst-free formation of organometallic compounds may be very advantageous for applications in organic solar cells and organic light emitting diodes.

In some applications of the present disclosure, the use of porous oxide (e.g., aluminum oxide) membranes (or porous ceramic membranes or, in some cases, porous metal membranes), particularly those produced according to the methods described herein (including those comprising bonded small porous (as well as dense, essentially pore-free) wires) as separation membranes may be advantageous. Such membranes may offer excellent mechanical properties (high strength, high toughness, high modulus, excellent creep and fatigue resistance), excellent thermal stability, high permeability, excellent chemical stability, high durability, lightweight, low cost, high uniformity, good wetting by a broad range of liquid materials, good flexibility, and many other attractive attributes. Conventional aluminum oxide membranes are produced by anodization of aluminum. This method suffers from long synthesis procedures and very high cost, while the produced membranes are typically very brittle, difficult to handle, and form cracks upon bending. Furthermore, the pores in such membranes are typically straight (see-through), which may be undesirable in some applications. In addition, such conventional membranes are difficult to mass-produce thinly (the minimum thickness is typically at least 50 microns). In contrast, the suitable thickness of the disclosed membranes herein may range from around 1 micron to around 20 mm for standalone membranes and from around 100 nm to around 5 mm for membranes deposited on another (e.g., porous) substrate. In some applications, it may be advantageous for such membranes to additionally comprise 0.1-90 wt. % polymer, 0.1-80 wt. % metal, or 0.1-80 wt. % carbon (e.g., for enhancing mechanical properties, for enhancing separation properties, or for other functionality, such as anti-bacterial, catalytic, etc., to name a few). Depending on the particular application and membrane composition, the suitable porosity in the disclosed membranes may range from around 0.001 vol. % up to around 99 vol. %. These separation membranes may be utilized for various filtration applications separating various particles (e.g., in the liquid or gaseous suspension state; including, but not limited to, various soft matter (including bio-related) particles, various ceramic particles, various carbon particles, various composite particles, dust, etc., the size of which may range from sub-mm to micron-scale and all the way up to nanoparticles), separating various liquids and gases (particularly if additionally comprising metals or polymers), among other species. These membranes may also be utilized in various applications requiring electrical insulation (e.g., in various electrochemical and electrical devices, including energy storage and energy harvesting devices, sensors, etc.). These membranes may also be utilized in applications requiring air and water filtration, including those where killing bacteria and bacteria spores is important. For these applications, it may be advantageous to deposit antibacterial (or anti-fungus) particles or coatings on the inner (and/or outer) surface of the porous membranes. Copper, its various alloys (e.g., brasses, bronzes, cupronickel, copper-nickel-zinc, etc.) and its various complexes (including those that comprise halogen atoms, such as Cl or Br), silver and silver alloys and various silver complexes, various antifungal complexes of Ni and Au, various organosilanes, various quaternary ammonium compounds (including those covalently bonded to a membrane surface or to a polymer layer on the membrane surfaces), and antifungal peptides, among others, are illustrative examples of materials suitable for use in such antibacterial or anti-fungus particles and coatings. Titanium oxide coatings on the membrane surface may also be used for catalytic decomposition of organic matter. Similarly, formation and utilization of porous membranes comprising copper, its various alloys (e.g., brasses, bronzes, cupronickel, copper-nickel-zinc, etc.) and its various complexes (including those that comprise halogen atoms, such as Cl or Br), silver and silver alloys and various silver complexes, various antifungal complexes of Ni and Au, titanium oxide and other suitable compounds as main membrane constituent(s) (not just as surface layer(s) or surface particles) may be advantageous.

The use of porous oxide (e.g., aluminum oxide) and other suitable electrically isolative ceramic membranes, particularly those produced according to the methods herein (including those comprising bonded small porous (as well as dense, essentially pore-free) wires), as separator membranes in electrochemical energy storage applications (e.g., fuel cells, batteries, supercapacitors, hybrid devices, etc.) may be particularly advantageous in view of the growing importance of these applications and thus will be described in more detail. The suitable thickness of such membranes may range from around 0.1 microns to around 200 microns (typically more desirable, from around 0.5 microns to around 100 microns). Advantages of using small aluminum oxide wires as compared to regular aluminum oxide particles include flexibility, strength, the ability to achieve very high porosity (e.g., over 70%, which may be important for high permeability), the ability to achieve a small size of the pores (which may be important for the prevention of potential Li dendrite penetration) and the ability to prepare thin membranes. Advantages of using porous small wires as compared to dense small wires include higher porosity (and thus higher permeation) for the same wire packing density. In addition, porous small wires may pack less densely compared with regular wires due to their higher surface roughness and lower density, which further increases separator permeation. Advantages of the described process (e.g., versus casting of individual wires) include bonding between individual wires, which helps to maintain robustness and resistance to fracture of the separator (even if it is very thin), while keeping it flexible. In some applications, it may be advantageous for such membranes to additionally comprise 0.1-10 wt. % polymer or 0.01-10 wt. % of another ceramic (e.g., for enhancing mechanical properties). Depending on the particular application, and membrane composition, the suitable porosity in the disclosed membranes may range from around 5 vol. % up to around 99.9 vol. % (more commonly from around 30 vol. % to around 95 vol. %), where typically higher porosity may be desired for thicker separator membranes or for applications requiring faster ion transport. Such membranes in energy storage applications may be infiltrated with a liquid or a solid electrolyte when used in devices. Superior strength, puncture resistance, outstanding thermal stability, low thermal expansion coefficient, relatively high dielectric constant, low cost, scalable manufacturability in thin form (down to 0.1 microns), good wetting properties for a broad range of materials, stability against reduction at low potentials (e.g., as low as 0 V vs. Li/Li$^+$ in the case of aluminum oxide) and against oxidation at high potentials (e.g., as high as 10 V vs. Li/Li$^+$), resistance against dendrite growth and other positive attributes of the disclosed membranes make them particularly attractive in a broad range of energy storage applications, including but not limited to various metal ion (such as Li-ion, Na-ion, Mg-ion, etc.) based energy storage devices (e.g., batteries including Li and Li-ion batteries, Na and Na-ion batteries, Mg and Mg-ion batteries, electrochemical capacitors, hybrid devices, etc.), to name a few.

Conventional polymer separators for Li-ion batteries suffer from limited mechanical strength and low thermal stability, which may lead to thermal runaway and cell explosions. Formation of flexible, strong, and thermally stable ceramic separators may overcome serious limitations of polymer separators.

FIGS. 18A-18E, 19, and 20 show example aspects of the fabrication and characterization of a flexible binder-free nonwoven fabric separator composed of γ-Al$_2$O$_3$ nanowires and produced according to the process illustrated in FIG. 15, where small Al ethoxide wires are first produced according to the process illustrated in FIG. 13.

Figure 18A:
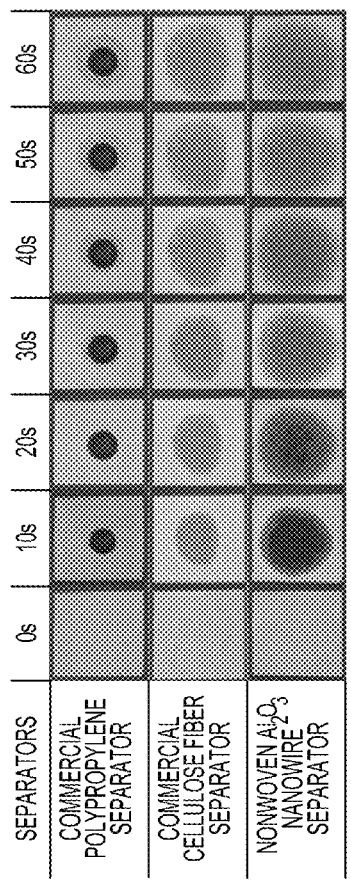
FIGS. 18A-18E, 19, and 20 illustrate various aspects and characterizations of the formation of porous oxide membranes and bulk samples out of nanowires (small wires) and the formation of composites comprising these oxide materials.
Figure 18B:
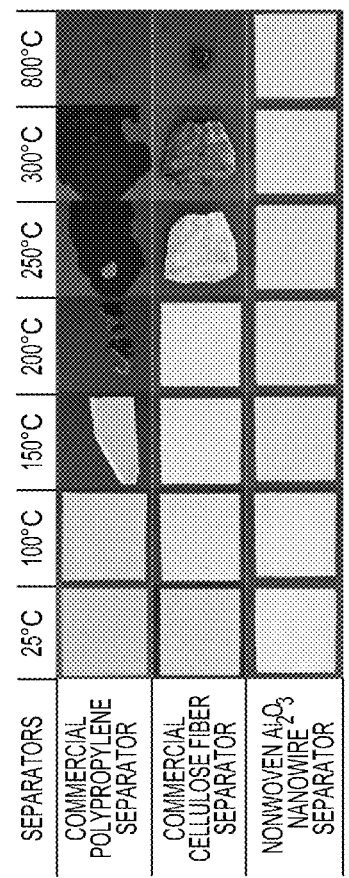
Figure 18C:
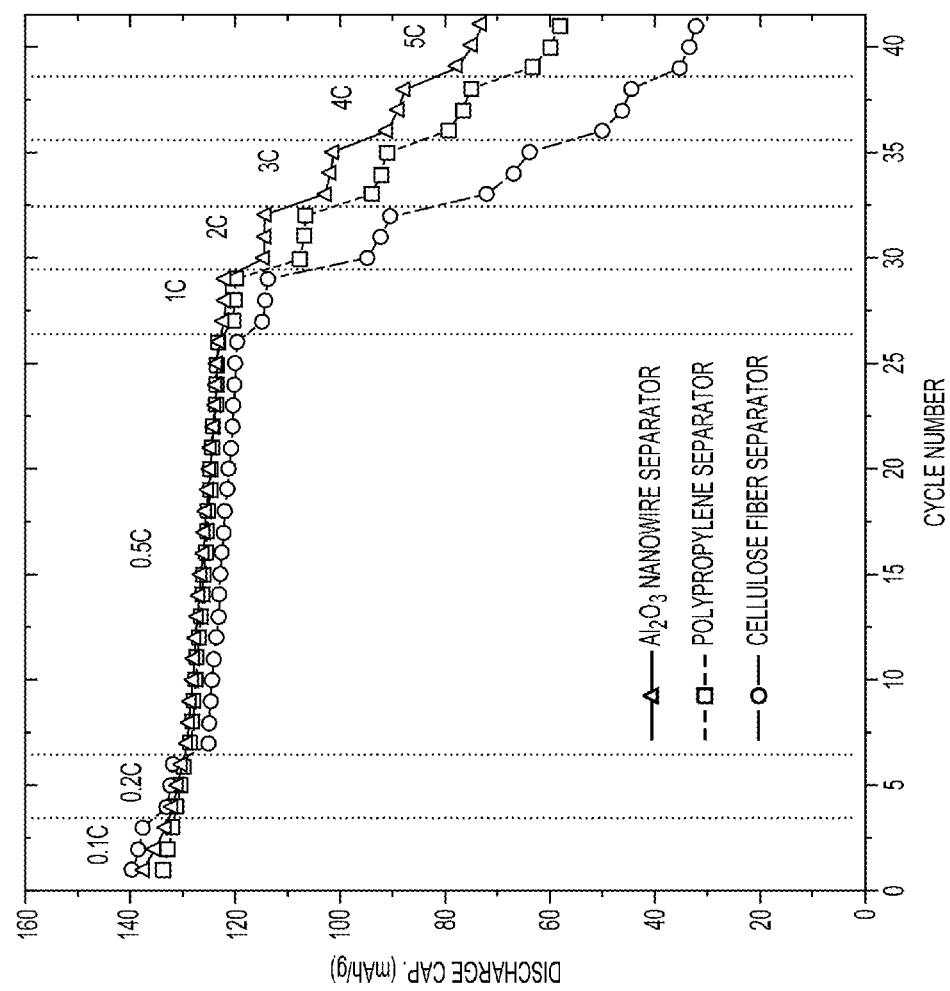
Figure 18D:
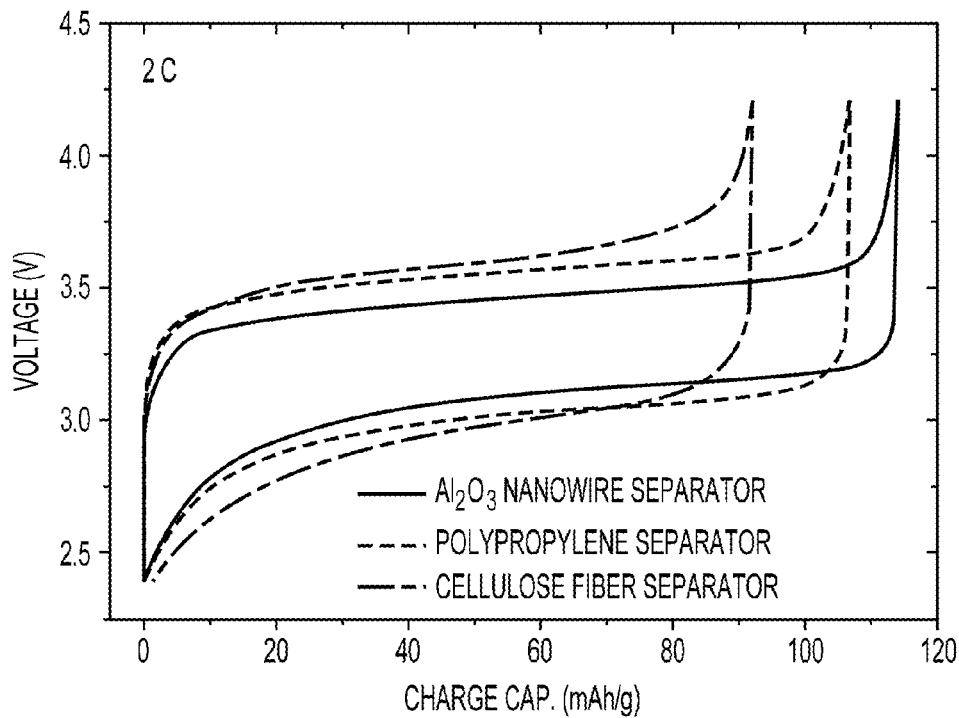
Figure 18E:
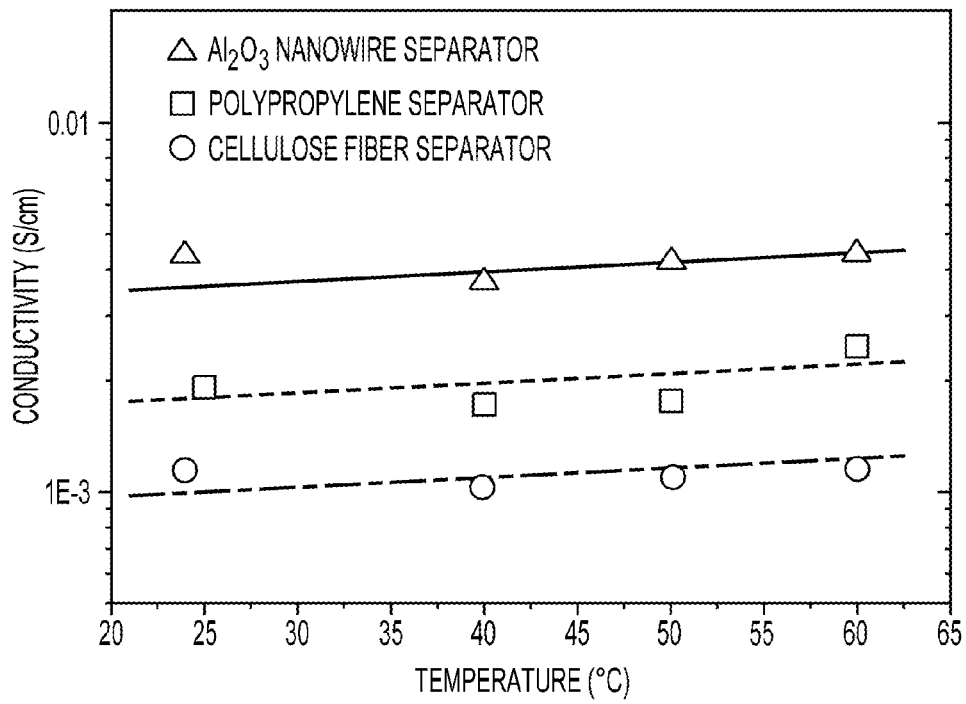
Figure 19:
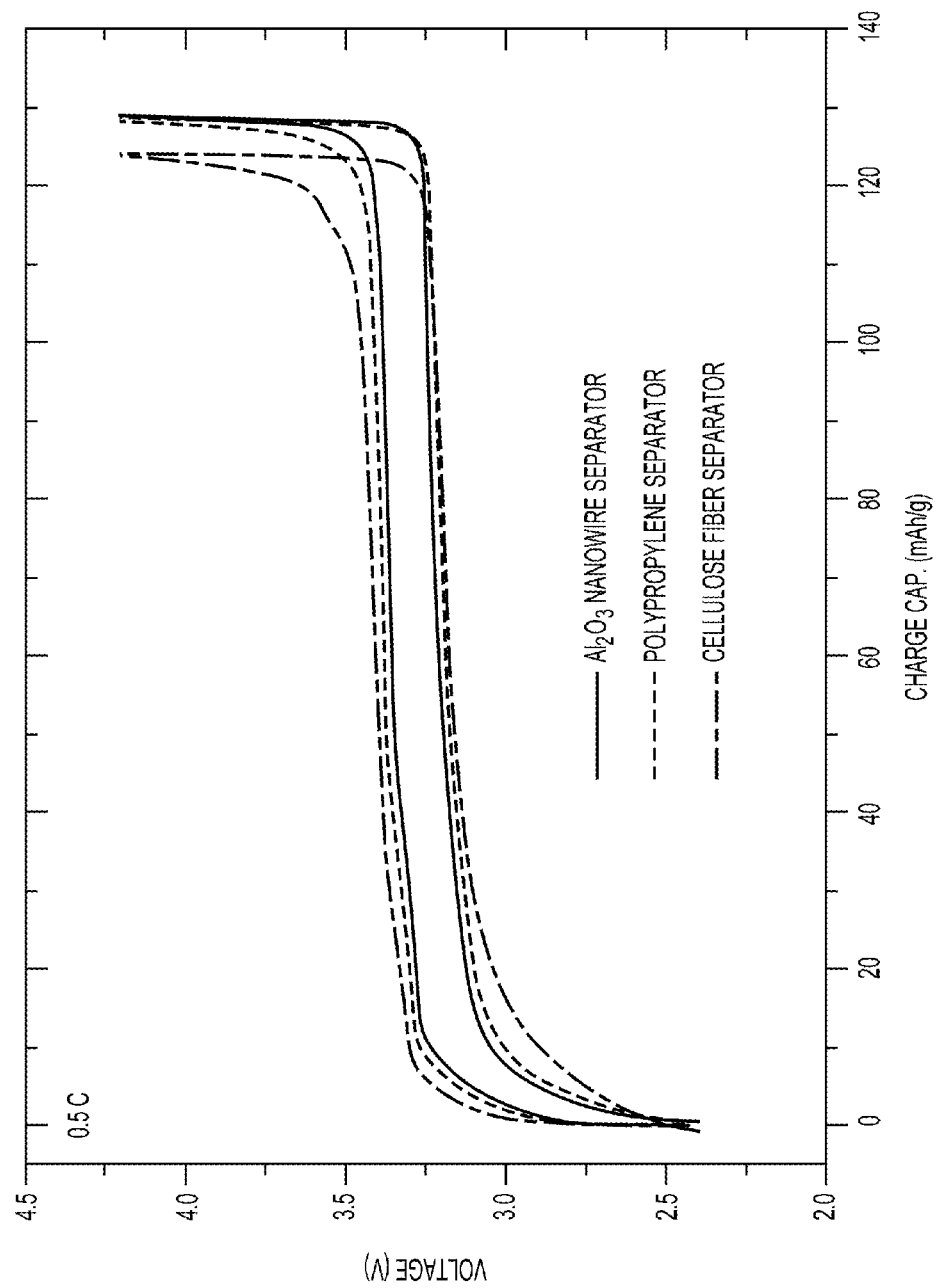

FIG. 18A compares results of simple wetting tests on a commonly used commercial olefin (polypropylene, PP) separator (top), a less common cellulose fiber (CF) separator (middle row), and a nonwoven γ-Al$_2$O$_3$ nanowire separator produced in accordance with the techniques described herein (bottom row). In this experiment, 5 μL of a commonly used commercial electrolyte (1M solution of LiPF$_6$ in carbonates) was dropped onto the separators and the wetted area was measured as a function of time. Due to higher polarity (the presence of strong surface dipoles), the wetting rate of the γ-Al$_2$O$_3$ separator is significantly higher, as determined by both the final wetting area and the speed of wetting. Additionally, the uniformity of wetting is increased because the as-produced γ-Al$_2$O$_3$ nanowire nonwoven membrane material is non-directional. FIG. 18B shows results of thermal stability tests performed starting at room temperature and increasing to 800° C. with separator samples placed into the furnace for 2 minutes at each temperature. The results effectively demonstrate the clear advantage of having a flexible porous ceramic separator with operating temperatures in excess of 800° C. (which may be achieved in the case of cell failure). In contrast, the most commonly used olefin separators typically start melting at around 120° C. and oxidize at around 300° C. Finally, the strength of ceramic fibers is known to significantly exceed that of the olefins, which allows formation of thinner separators in lithium ion batteries without sacrifice of their mechanical properties. This, in turn, increases cell energy density. For example, reduction in separator thickness from 25 to 5 μm leads to a 13-15% increase in cell energy density, which typically translates into a similar reduction in cell cost on the cost-per energy basis. FIGS. 18C, 18D, and 19 show electrochemical performance of full cells with a graphite anode, lithium iron phosphate (LFP) cathode, and all three types of separators. While cells with all three types of separators exhibited comparable performance at low (0.1 C to 0.5 C) current densities, the cells with Al$_2$O$_3$ nanowire separators show significantly higher capacities retained at high (1 C to 5 C) discharge rates. The lack of detectable oxidation during cell charging to 4.2 V shows the requisite chemical compatibility of the Al$_2$O$_3$ nanowire separator. Noticeably smaller 2 C charge-discharge hysteresis may be observed in cells with Al$_2$O$_3$ nanowire separator, which can be advantageous for various applications. Such a difference in hysteresis suggests better transport properties and lower cell polarization provided by the Al$_2$O$_3$ nanowire separator. FIG. 18E shows results of independent electrochemical impedance spectroscopy (EIS) testing of these three separators using symmetric coin cells with stainless steel working and counter electrodes. They showed a consistently higher conductivity of Al$_2$O$_3$ nanowire separators, thus demonstrating their additional advantage in battery applications.

Figure 20:
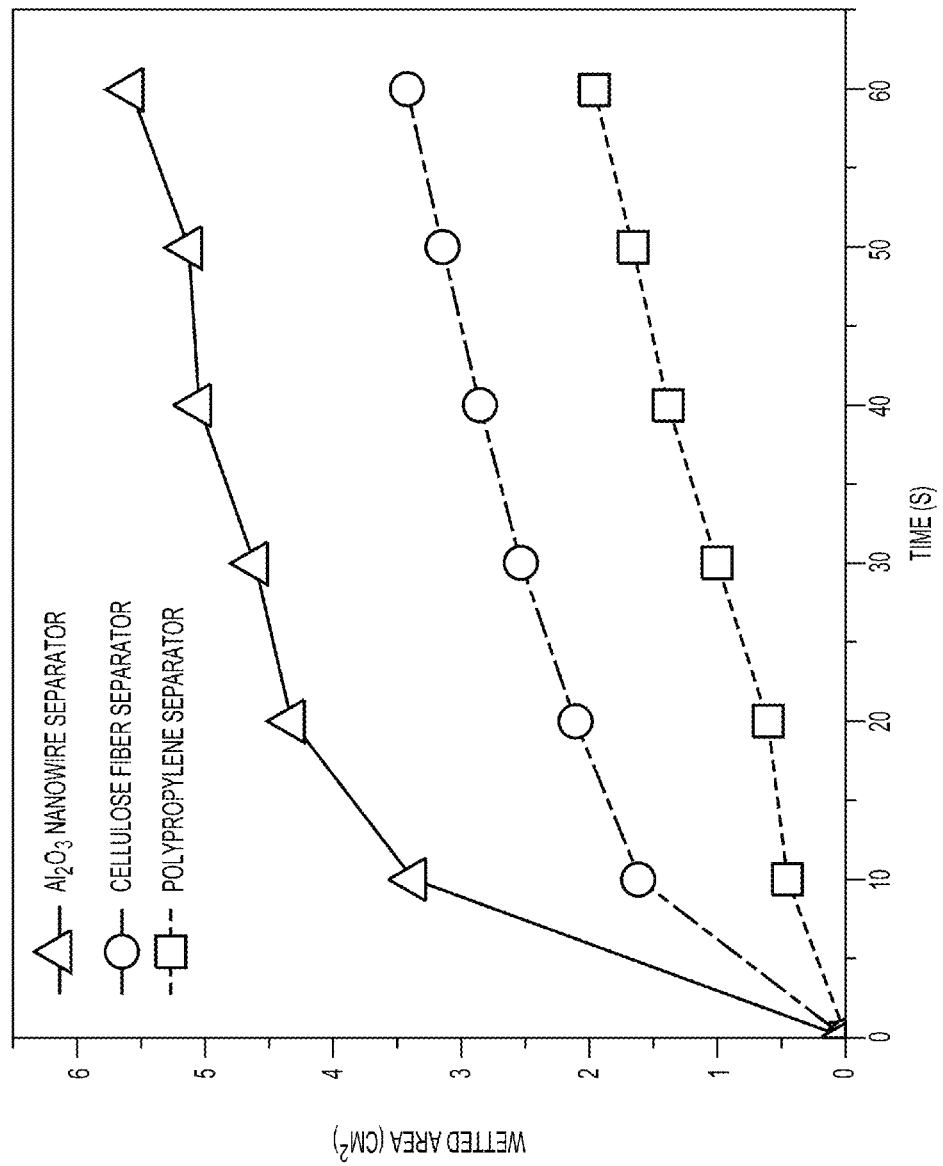

FIG. 20 shows results of a numerical analysis of the changes in the electrolyte wetted area of the three separators from FIG. 18A. Faster wetting of the ceramic (e.g., Al$_2$O$_3$) separators may be advantageous in applications that benefit from reduced cell polarization and faster charge or discharge rate performance.

Overall, the use of extra-thin (e.g., less than 5-10 μm) and highly porous (e.g., porosity greater than 75%) aluminum oxide (and other suitable oxide and suitable ceramic) membranes may allow one to noticeably increase the rate capability and energy density of Li and Li-ion batteries as well as that of other batteries, while increasing or maintaining the required level of safety. This level of porosity, beneficial for high rate capabilities, in combination with mechanical integrity and flexibility is only attainable using small wire-like structures because regular (e.g., near spherical) particle-based ceramic structures require substantially denser packing to produce a mechanical network and are typically not very flexible. By moving away from the typical use of polymers in the Li-ion battery separator, the thinner (e.g., to around 5 μm) ceramic separators (such as those described herein) will demonstrate higher strength and fracture toughness than thicker (e.g., a 20 μm thick) polymer separator with ceramic coating(s), while also reducing the thickness of the Anode/Separator/Cathode stack by approximately 10%, thereby increasing the energy density of the Li-ion battery by 10% —a major benefit. Increased cell energy density will also reduce the system costs ($/kWh) of battery packs as, for example, 10% fewer cells may be packaged and monitored for the same capacity. Due to their high stability at high potentials, such membranes may be used in combination with high voltage cathodes (e.g., cathodes having an average lithiation potential from around 3.9 to around 5.6 V vs. Li/Li$^+$) in Li and Li-ion battery cells. It is noted that in addition to using a standalone porous aluminum oxide membrane, small wires (e.g., made of aluminum oxide or porous aluminum oxide) may be directly deposited on at least one of the electrodes by using casting or spray deposition or by field-assisted deposition or dip coating, or another suitable method. Such deposited wires may serve as an integrated (thin and flexible) membrane separating anodes and cathodes from direct electrical contact, while providing small resistance to ion transport and occupying a relatively small space.

In addition to $Al_2O_3$ membranes, other ceramic membranes (including those produced from or comprising small wires, including porous small wires) may be utilized as separators in Li-ion and other batteries. These include MgO, $ZrO_2$, and many others. The important parameters are mechanical properties, stability of the ceramic membrane in electrolyte and (in case of direct contact with positive or negative electrodes) the lack of electrochemical side reactions (such as significant lithiation or dissolution, in contact with electrodes).

In some applications, it may be advantageous to deposit a porous polymer layer on one or both sides of the ceramic ($Al_2O_3$, MgO, $ZrO_2$, $WO_2$, $W_2O_3$, etc.) separator membrane in order to further reduce small side reactions with electrodes. For example, when such membranes are used in Li or Li-ion (or Na or Na-ion or other metal or metal-ion) batteries, depositing such a porous polymer layer (e.g., porous ethylene, porous propylene, porous aramid, porous cellulose, etc.) on the anode side of the membrane may prevent undesirable side reactions (e.g., lithiation, reduction, etc.) between the anode and the ceramic separator. Similarly, formation of such a porous polymer layer on the cathode side of the membrane may reduce potential undesirable oxidation reactions. A suitable thickness of such a porous polymer layer may range from around 10 nm to around 10 microns. In some applications of Li and Li-ion (or other metal or metal-ion batteries), it may be advantageous to deposit a thin (e.g., from about 1 nm to about 200 nm), mostly nonporous (dense) polymer layer on the inner surface of the membrane (e.g., around individual or bonded wires) to prevent direct Li contact with the ceramic wires (e.g., in case of Li dendrite formation). It may be further preferable for such a polymer layer to be stable in contact with Li and exhibit high interfacial energy at the polymer/Li interface. In this case, formation of the Li dendrite would result in a substantial increase in the energy of the system and its growth may be significantly reduced or eliminated. In contrast, direct contact of Li with many ceramic materials may result in the formation of a low-energy interface, which would reduce the surface energy of the Li dendrite and thus undesirably favor its propagation.

In some applications, it may be advantageous for the porous polymer layer on one or both sides of the ceramic ($Al_2O_3$, MgO, $ZrO_2$, $WO_2$, $W_2O_3$, etc.) membrane to be thermally responsive (or comprise a thermally responsive layer) and close pores above a certain temperature. This may provide an additional safety feature of the cell because above a certain temperature (e.g., selected in the range from about 70 to about 150° C., for typical applications; for some applications, above 100° C.) the membrane would shut the current flow. In some designs, a thermally responsive layer may comprise a thermoplastic that melts above a critical temperature (e.g., selected in the range from about 70 to about 150° C., for typical applications) to cut off Li ion conduction.

In some applications, the use of oxide (e.g., aluminum oxide, magnesium oxide, zirconium oxide, etc.) or other suitable ceramic small wire (including but not limited to porous small wires) membranes (particularly in combination with the above-discussed polymer coatings) in metal anode-based battery cells in medium sized (from around 10 mAh to around 200 mAh), large (from around 200 mAh to around 10,000 mAh), or extra-large (above around 10,000 mAh) cells may be particularly advantageous. Example of suitable metal anode-based battery cells include, but are not limited to, cells with a Li anode (e.g., as in Li metal batteries), Mg anode (e.g., as in Mg metal batteries), Na anode (e.g., as in Li metal batteries), Zn anode (many battery chemistries comprising Zn or Zn alloy anodes and electrolytes that do not induce dissolution or reduction of small wire membranes), and K anode (e.g., as in K metal batteries), to name a few. Rechargeable metal anode batteries may particularly benefit from this membrane technology. Metal anodes in such rechargeable battery cells typically undergo metal stripping (dissolution into electrolyte as ions) during discharging and re-plating during charging. This process typically leads to the formation of dendrites that may induce internal shorting, which may lead to battery failure (and, in some cases, to various safety risks such as fires, particularly known in Li battery chemistries). The use of solid electrolytes or surface layer protection with a solid ceramic protective layer is often expensive, not always feasible, and does not always protect the cell from dendrite penetration (particularly in situations where the battery may be shocked or exposed to various stresses, as when used in transportation). While it is common in battery research for scientists to utilize so-called half cells with metal anodes (e.g., Li half cells) in order to evaluate the performance of their electrode materials or separators (typically in very small coin cells having a capacity below 10 mAh), the use of metal anodes in commercial cells (particularly in rechargeable cells with liquid aqueous and organic electrolytes) is rare because of their higher cost as well as reliability and safety concerns (larger sized cells would release more energy during dendrite-induced thermal runaway and rapid disassembling, particularly when flammable organic electrolytes are utilized). The use of small wire membranes as described herein (e.g., porous aluminum oxide, magnesium oxide, or zirconium oxide membranes, to provide a few examples) with a relatively high elastic modulus of the membrane material, high porosity, and (potentially importantly) small (e.g., below 2 microns, more preferably below 0.25 microns, on average) and tortuous pores may greatly suppress or eliminate dendrite growth, while providing relatively fast metal (e.g., Li, Mg, Zn, etc.) deposition (plating) and thus high power density. While a detailed understanding of this phenomena is still lacking, it may be related to the associated increase in surface area (and thus surface energy) of a dendrite, which leads to a high energy barrier for dendrite formation, particularly if the individual wires are coated with a suitable polymer layer (e.g., a polymer that is stable in direct contact with a metal anode, exhibits high elastic modulus and exhibits high interfacial energy in such a contact). While metal dendrites may penetrate through many polymer membranes (during metal dendrite growth in a cell with a polymer separator membrane), the metals dendrites are typically too soft to penetrate through individual small oxide wires (e.g., small aluminum oxide wires) even if these are coated with polymer layers. Therefore, metal dendrite formation may require dendrites to grow around the small wires (within small and tortuous pores formed between the small wires in a membrane), which significantly increases the dendrite specific surface area. The small features of the membrane walls, its roughness, its dielectric properties, or its surface properties may also be responsible for the suppression of dendrite growth.

In some applications, the use of oxide (e.g., aluminum oxide, magnesium oxide, zirconium oxide, etc.) and other suitable ceramic small wires (including but not limited to porous small wires) membranes in battery cells comprising so-called "conversion"-type (including so-called "chemical transformation"-type) electrode materials (particularly in medium sized, from around 10 mAh to around 200 mAh), large (from around 200 mAh to around 10,000 mAh) or extra-large (above around 10,000 mAh) cells) may be particularly advantageous. In contrast to so-called "intercalation" electrodes, conversion materials break and create new chemical bonds during insertion and extraction of ions (e.g., Li ions in the case of Li-ion and Li-metal batteries). Two types of conversion reactions may be distinguished for Li chemistries:

Type A (true conversion): $M'X_z + yLi \leftrightarrow M + zLi_{(y/z)}X$ (Eq. 1)

Type B (chemical transformation): $yLi + X' \leftrightarrow Li_yX$, (Eq. 2)

where M'=cation, M=reduced cation material, and X'=anion.

For the type A cathodes, M' are typically transition metal ions, such as $Fe^{3+}$, $Fe^{2+}$, $Ni^{2+}$, $Cu^{2+}$, $Co^{2+}$, $Bi^{2+}$, $Ag^+$, $Mn^{3+}$, etc., while X' are typically halogen ions (such as $F^-$, $Cl^-$, $Br^-$, and $I^-$) or chalcogenide ions (such as $S^{2-}$, $Se^{2-}$, etc.). X' may also be $O^{2-}$. Suitable examples of "conversion"-type active electrode materials include, but are not limited to, various metal halides and oxi-halides, various chalcogenides (including, but not limited to, $Li_2S$ and S), various metal oxides, various metal hydroxides and oxyhydroxides, their mixtures and alloys, etc. During operation of rechargeable cells, conversion-type electrodes typically exhibit some undesirable interactions with electrolytes. For example, liquid electrolytes may induce dissolution or etching of such electrode materials (the dissolution of lithium polysulfides in lithium-sulfur cells is particularly well-known; the dissolution of metal components of the conversion-type electrodes is another example). In addition to the loss of active material in the electrode (e.g., in a cathode), the components of the dissolved species may travel to an opposite electrode (e.g., to an anode) and induce undesirable damage to its surface (e.g., damage to the anode solid electrolyte interphase) or at least partially block ionic pathways to the anode, leading to an undesirable increase in resistance and reduction of capacity of a cell. The use of the above-described small wire membrane may alleviate such negative effects by adsorbing dissolved species on its surface or by adsorbing harmful electrolyte components (e.g., fluorine and fluorine-containing ions, various halogen and halogen-containing ions, $H_2O$, etc.) on its surface or by other mechanisms. High specific surface area resulting from the small diameter of the small wires may be advantageous for maximizing its positive impact.

In some applications, the use of oxide (e.g., aluminum oxide, magnesium oxide, zirconium oxide, etc.) and other suitable ceramic small wires (including but not limited to porous small wires) membranes in metal and metal-ion (e.g., in Li and Li-ion) battery cells comprising so-called "alloying" active materials (e.g., Si, Sn, P, Al, Ge, Sb, Bi, etc.) may be advantageous. The inventors have found that the presence of traces of water, hydro-halide (e.g., HF) acid, fluorine ions, and other halide-comprising ions in liquid organic electrolytes may induce undesirable damage to the surface of such materials (particularly strong damage to Si, Sn, and Ge) during cell operation. The use of the above-described small wire membrane may alleviate such negative effects by adsorbing harmful electrolyte components (e.g., fluorine and fluorine-containing ions, various halogen and halogen-containing ions, $H_2O$, etc.) on its surface or by other mechanisms. High specific surface area resulting from the small diameter of the small wires may be advantageous for maximizing its positive impact. In addition, stresses and additional heat originating from the volume changes in "alloying" or "conversion" active materials during cycling may induce damage in polymer separators. The use of more robust ceramic separators instead of traditional polymer separators may thus be advantageous in terms of cell stability and performance.

In some applications, the use of oxide (e.g., aluminum oxide, magnesium oxide, zirconium oxide, tungsten oxide, tantalum oxide, etc.) and other suitable ceramic small wires (including but not limited to porous small wires) membranes in metal and metal-ion (e.g., in Li and Li-ion) battery cells comprising high voltage cathode materials (e.g., materials with average Li extraction potential in the range from around 3.8 V to around 5.8 V vs. $Li/Li^+$ or cathode materials with a maximum charge potential from around 4.4 V to around 6.2 V vs. $Li/Li^+$). At elevated potentials (typically above around 3.8-4.3 V vs. $Li/Li^+$) such a cathode may exhibit some undesirable interactions with electrolytes, such as, for example, dissolution or etching of metal components (e.g., Mn, Co, Ni, etc.) of such cathodes. Such reactions may be particularly harmful if traces of hydro-halide (e.g., HF) acid, fluorine ions, and other halide-comprising ions are present in liquid electrolyte. The use of the above-described small wire membrane may elevate such negative effects by adsorbing harmful electrolyte components (e.g., fluorine and fluorine-containing ions, various halogen and halogen-containing ions, etc.) on its surface or by other mechanisms. High specific surface area resulting from the small diameter of the small wires may be advantageous for maximizing its positive impact.

In some applications, the use of an ionically permeable (e.g., porous) polymer layer between the oxide (e.g., aluminum oxide, magnesium oxide, zirconium oxide, etc.) small wires (including but not limited to porous small wires) membranes and at least one of the electrodes may be beneficial for their use as separators in electrochemical cells (e.g., battery cells). Such a polymer layer may be deposited on a membrane or on an electrode or simply sandwiched between the ceramic membrane and at least one of the electrodes. Such a polymer layer may serve different useful functions. In one example, it may reduce stress concentration at the interface between an electrode and the porous oxide separator (because polymers are typically softer and more deformable compared to oxides). This may lead to enhanced reliability during cell assembling when the cell stack is pressurized and to a more reliable cell operation. In another example, such a polymer layer may make the oxide separator easier to handle (e.g., during cell assembling or oxide membrane production). In yet another example, such a polymer layer may enhance adhesion between the oxide membrane and an electrode (e.g., essentially serving as a gluing/adhesive layer). In yet another example, such a polymer layer may enhance electrochemical stability of the oxide membrane. As described above, for example, in the case of Li or Li-ion batteries the use of a polymer layer between an oxide membrane and an anode may prevent reduction of the oxide by Li or other unfavorable interactions at low potentials (e.g., below around 0.1-2 V vs. $Li/Li^+$, depending on an oxide and electrolyte chemistry). In this case, not only aluminum, magnesium, and zirconium oxides, but also many other oxides that are typically unstable or significantly less table in contact with Li may be utilized (e.g., silicon oxides, zinc oxides, iron oxides, magnesium oxides, cadmium oxides, copper oxides, chromium oxides, titanium oxide, various combination of oxides, etc.). If a polymer layer is placed between an oxide membrane and a cathode, it may prevent or minimize various undesirable interactions between an oxide and electrolyte or a cathode at higher potentials (e.g., above around 3-4 V vs. $Li/Li^+$, depending on the oxide and electrolyte chemistry). In yet another example, such a polymer layer may serve as an additional safety mechanism. For example, it may prevent ion transport (e.g., by closing the pores or by becoming impermeable by the electrolyte solvent, or by other mechanisms) if heated above a critical temperature (or cooled below a critical temperature). The suitable porosity of such a polymer layer may range from around 0 to around 99 vol. % (more preferably, from around 10 to around 90 vol. %). The suitable thickness of such a polymer layer may range from around 5 nm to around 20 microns (more preferably, from around 10 nm to around 10 microns). Thicknesses smaller than around 5 nm may typically reduce the usefulness of such a polymer layer, while thickness larger than around 20 microns undesirably increase the total separator stack thickness and may also induce harmful effects (e.g., polymer shrinking during heating may also damage an oxide membrane). The polymer layer may be a part of a multilayer (oxide wire-comprising) membrane or be deposited on at least one of the electrodes or be prepared as a stand-alone film. The composition of the polymer layer may depend on a particular functionality that is desirable and a particular chemistry of an electrochemical cell, and may be selected from the list of polymer compositions discussed in conjunction with the polymer composites described herein.

In some applications, the use of oxide (e.g., aluminum oxide, magnesium oxide, zirconium oxide, etc.) or other suitable ceramic small wires (including but not limited to porous small wires) as thermally stable, electrically isolative mechanical reinforcement in electrodes, solid (e.g., polymer, ceramic, glass-ceramic, or composite) electrolyte and separators of various batteries (e.g., Li and Li-ion batteries, Na and Na-ion batteries, etc.) and other electrochemical energy storage devices may also be highly advantageous. Small wires may enhance mechanical strength, fatigue resistance, and overall durability of the electrodes without providing undesirable electrochemically active surface area for decomposition of electrolyte due to the lack of electrical conductivity in aluminum oxide and other oxides, in contrast to, for example, carbon nanotubes or carbon fibers and nanofibers. In addition, the use of oxide (e.g., aluminum oxide, magnesium oxide, etc.) or other suitable ceramic small wires may be advantageous for providing (and maintaining during cycling) fast ionic pathways within electrodes. For example, pores in the porous oxide (e.g., aluminum oxide or magnesium oxide, etc.) small wires may be utilized as pathways for ion access from the top surface to the bulk of the electrode. Since these pores may remain filled with electrolyte but empty from electrolyte decomposition products and since mechanical strength of the oxide may be sufficiently large to withstand volume changes in the electrodes during operation without inducing collapse of the pores, such pores may be successfully utilized for maintaining high ionic conductivity within the electrode during cycling. In some applications, the use of oxide (e.g., aluminum oxide or magnesium oxide) small wires (including but not limited to porous small wires) in combination with carbon nanotubes, carbon fibers (nanofibers), carbon small wires, and other carbon particles may be advantageous. The oxide wires may help to disperse binder and/or carbon particles within the electrode and enhance mechanical stability of the electrodes (particularly important for electrodes comprising high capacity (e.g., greater than about 400 mAh/g in the case of anodes and greater than about 250 mAh/g in the case of cathodes) or high volume changing (e.g., greater than about 10 vol. %) active materials), while conductive carbon may enhance electrical connectivity between individual electrode particles comprising active materials.

In some applications, the use of the various small wire comprising composites (particularly those described herein) in the form of fibers, nanofibers, threads, ropes, and fabrics may be advantageous. Such fibers may be produced, for example, by spinning, melt-spinning or electrospinning, extrusion or other suitable methods of composite fiber fabrications.

In some applications, the use of small oxide (e.g., aluminum oxide, magnesium oxide, or other oxide) and ceramic wires and oxide (e.g., aluminum oxide or other oxide) and ceramic membranes, particularly those produced according to the methods herein, in small wire/ceramic composites is advantageous.

In some applications, the use of metal (such as aluminum, magnesium, titanium, etc.) oxyhydroxides, hydroxides, and oxides in the form of small wires (particularly those described herein, including porous small wires) or in the form of porous membranes as fillers in asphalts and concretes (including asphalt concretes) may be advantageous in terms of increasing strength, toughness, fatigue resistance, improving dynamic modulus, moisture susceptibility, creep compliance, rutting resistance and freeze-thaw resistance, reducing manufacturing time and energy consumption, and providing other benefits compared to the use of regular (small wire-free) asphalt, brick (and other masonry structures), or concrete compositions. Furthermore, the application of such small wires may provide better durability and properties when compared to more traditional fiber-reinforced concretes with typical polypropylene fibers, polyester fibers, asbestos fibers, cellulose fibers, carbon fibers, glass fibers, and nylon fibers. In some applications, it may be advantageous to use metal (such as aluminum, magnesium, titanium, and other metal) oxyhydroxides, hydroxides, and oxides in the form of small wires (particularly those described herein, including porous small wires) or in the form of porous membranes in combination with polymer (e.g., polypropylene, polyester, cellulose, nylon), mineral (e.g., asbestos), carbon, or glass fibers. The suitable mass fraction of small wires in asphalts and concretes may range from around 0.001 wt. % to around 40 wt. %. In some applications, it may be advantageous to use small wire/polymer composites or porous membranes/polymer composites (such as aluminum) oxide/polymer composites, particularly those described herein, including porous small wires) (for example, in the form of fibers, timber structures, rods, etc.) as reinforcements in structural applications (such as concretes, asphalts, buildings, etc.).

In some applications, the use of aluminum oxide (and other oxide) and other ceramic (e.g., carbide) small wires (particularly those described herein) as fillers in various metals and metallic alloys may be highly advantageous in terms of increasing hardness, strength (and specific strength), fatigue resistance, elastic modulus, wear resistance, scratch resistance, thermal stability, creep resistance, fracture toughness, manufacturability in thin foil states, and other important properties of metals and metal alloys. The applications of such small wire/metal composites may include cases for a broad range of devices, sporting goods, various medical tools, various cutting tools (including cutting blades), various components of electronic devices, various conductive small wires, jewelry, various components of transportation devices (including but not limited to land, sea, and air and space transportation), various constructions and load-bearing applications, various energy storage devices, various protection devices, and various engines and turbines, to name a few. Examples of suitable lightweight metals and metal alloys include, but are not limited to, aluminum and various aluminum alloys, magnesium and various magnesium alloys, titanium and various titanium alloys, and beryllium and various beryllium alloys. Examples of suitable structural (including piping, plumbing, gearing, valves, engines, turbines, etc.) metals and metal alloys include, but are not limited to, iron and iron alloys (e.g., various steels, including carbon steel and stainless steel, among others), copper and copper alloys, aluminum and aluminum alloys, magnesium and various magnesium alloys, zinc and zinc alloys (e.g., for soldering or surface coatings), tin and tin alloys (e.g., for soldering), lead and lead alloys (e.g., for soldering), vanadium and vanadium alloys (mostly as components of other alloys), chromium and chromium alloys (mostly as components of other alloys), tungsten and tungsten alloys (e.g., in armor, in gas turbines, etc.), and nickel and nickel alloys. Examples of suitable metal and metal alloys for use in current collectors and conductive small wires and other applications requiring high electrical conductivity include, but are not limited to, gold and gold alloys, silver and silver alloys, aluminum and aluminum alloys, copper and copper alloys, platinum and platinum alloys, molybdenum and molybdenum alloys, zinc and zinc alloys, lithium and lithium alloys, tungsten and tungsten alloys, brass, nickel and nickel alloys, titanium and titanium alloys, and palladium and palladium alloys, to name a few. Examples of suitable metal and metal alloys for use in jewelry and jewelry-related (e.g., watches and portable and wearable electronic devices) applications include, but are not limited to, gold and gold alloys (e.g., 10 karat, 12 karat, 14 karat, 18 karat, 22 karat, 24 karat, etc., various types of white gold and rose gold alloys, etc.), platinum and platinum alloys, silver and silver alloys, various nickel alloys (e.g., so-called "nickel-silver," which comprises Ni, Cu, and Zn), palladium and palladium alloys, rhodium and rhodium alloys, tungsten and tungsten alloys, titanium and titanium alloys, various stainless steels, and copper and copper alloys (including brass), to name a few. Examples of suitable high temperature corrosion resistant alloys include, but are not limited to, various nickel-based super-alloys, molybdenum alloys, tungsten and tungsten alloys, stainless steels, and tantalum alloys and titanium alloys, to name a few examples. Examples of other suitable metal and metal alloys include, but are not limited to, metals and alloys comprising at least one of the following elements: Cr, Mn, Co, Y, Zr, Nb, Mo, Tc, Ru, Rh, Pd, Cd, In, Ga, Sn, Hf, Ta, Re, Os, Ir, Hg, Rf, Db, Sg, Bh, Hs, Mt, La and various elements in the lanthanide series, Ac and various elements in the actinide series, and various shape memory alloys, to name a few. The suitable mass fraction of small wires in metal-wire composites may range from around 0.002 wt. % to around 85 wt. %.

In some applications, it may be advantageous to add a particular color to oxide small wire/metal composites to modify the otherwise "regular metallic" color. For example, it may be advantageous for "colored" (e.g., black, white, blue, red, green, velvet, yellow, gold, silver, or other color) cases and frames of various electronic devices (laptops, ultrabooks, tablets, electronic books, televisions, credit card terminals, cameras, microscopes, spectroscopes and other research tools, monitors of various other electronic devices or components of devices, etc.), cases of watches and other wearable devices, furniture, frames of reading glasses, components of automotive, aerospace, ship and other transport devices (cars, buses, planes, ships, spacecraft, drones, etc.), components of various appliances (oven doors, cook tops, etc.), tableware glass, jewelry, components of various protection equipment (safety screens, helmets, personal protection equipment, etc.), various sporting goods, various interior design and furniture (mirrors, partitions, balustrades, tables, shelves, lighting) and other devices where it is desirable to not reveal scratches. It may be desirable for the metals and small wire/metal composites to exhibit a uniform color throughout the metal (small wire/metal, porous oxide-metal) part(s) or at least through a sufficiently thick surface layer (typically at least 1 micron or more, preferably 10 microns or more) instead of introducing it to a thin layer on the surface (e.g., by anodization) or using a relatively soft polymer-based paint on the surface. Conventionally, various dyes are difficult to introduce (without damage to the dyes) and distribute uniformly within a metal (particularly without reducing metal mechanical properties). The present disclosure overcomes this limitation. For example, in some applications, suitable dyes or quantum dots may be attached to the surface of the oxide small wires or be infiltrated into the pores (if present in small wires) prior to the formation of the small wire/metal composites. In some applications, it may be advantageous to seal these pores in order to prevent direct contact between the dyes (or quantum dots) and metal. In some applications, the sealing material may be a glass (e.g., oxide) or a ceramic (e.g., an oxide, a nitride, or a carbide, to provide a few examples). In some applications, porous oxides of not elongated shape (not small wires) and other porous materials may be utilized for the purpose of introducing a color to a metal or metal-ceramic composite. In some applications, instead of dyes, particles or coatings may be utilized (e.g., carbon particles or carbon coating for "black" color).

Examples of suitable methods for the formation of small wire (e.g., aluminum oxide small wire, among other oxides and other ceramic small wire)/metal composites include, but are not limited to, plating and electroplating (e.g., through small wire-comprising or small wire-based membranes or small wire-based porous bulk samples), melt-infiltration (e.g., into small wire-comprising or small wire-based membranes or small wire-based porous bulk samples), physical vapor deposition (sputtering, pulse-laser deposition, etc.), chemical vapor deposition, various mechanical alloying methods (e.g., ball milling, friction stir, etc.), various powder metallurgy methods (including, but not limited to, various sintering methods, such as spark plasma and plasma-activated sintering and magnetic-field-assisted sintering, pulsed current hot pressing, hot isostatic pressing, hot pressing, etc.), various casting methods (e.g., pressure casting, hot pressing including vacuum hot pressing, squeeze casting, etc.), sheath rolling, and ultrasonic consolidation, to name a few. As mentioned above, in order to tune the small wire/metal interface strength, in order to improve wetting of metals on the small wire surface, or in order to tune other properties of the small wire/metal interface (or interphase), it may be advantageous to pre-coat the small wire surface with coatings of other materials (e.g., by carbon, by ceramic—e.g., carbides (such as boron carbide, aluminum carbon, etc.) or by metals (e.g., by metals other than the "main" metal of the small wire-metal composites)).

In some applications, it may be advantageous to utilize some of the above-described lightweight small wire (e.g., aluminum oxide small wire, among other oxides and other ceramic small wire)/metal composites in ballistic protection applications (e.g., in bulletproof or stab-protective vests or bulletproof structural materials, such as plates, etc.). Lightweight alloys (such as aluminum alloys, magnesium alloys, titanium alloys, beryllium alloys, their combinations, etc.) and (in the case of plates) steel may be particularly advantageous for use in such composites. As mentioned above, it may be advantageous to pre-coat the small wire surface with coatings of other materials (e.g., by carbides (such as boron carbide, silicon carbide, aluminum carbon, among others), borides, etc.), by metals (e.g., by metals other than the "main" metal of the small wire/metal composites), or by polymers) in order to optimize mechanical properties of the small wire/metal composites and improve wetting of metals on the small wire surface. In some ballistic applications, polymers may be used instead of metals in such composites. Examples of suitable polymers include, but are not limited to, nylon, polyethylene, polyacrylonitrile (PAN), aramids (such as p-phenylene terephthalamides (PPTA)), polybenzoxazole, poly(pyridobisimidazole) (such as commercially available Kevlar® (e.g., Kevlar 49, 149, etc.), Zylon® HM, M5® (PIPD), Twaron®, Technora®, Zylon®, etc), silk, spider silk, among others. In some ballistic applications, ceramic, carbon, and glass may be used instead of metals in such composites. In some applications, the small wire-comprising composites may be in the form of fibers or fabrics. In some ballistic applications, silicon carbide, boron carbide, or carbon small wires or platelets (or plates) as well as aluminum oxide platelets (or plates) may be utilized in addition to aluminum oxide small wires in such composites. The suitable mass and volume fractions of the small wires in ballistic protection composites may range from around 0.01 vol. % (and around 0.01 wt. %) to around 80 vol. % (and around 80 wt. %).

In some applications, the use of aluminum oxide (or other oxides and other ceramic) small wires (particularly those described herein) or porous bodies or porous membranes in catalyst applications may be advantageous. The use of oxide or ceramic small wires in combination with carbon particles (such as carbon nanotubes, exfoliated graphite, graphene, porous carbon particles, carbon nanoparticles, etc.) or carbon coatings may be advantageous.

In some applications, it may advantageous to use aluminum oxide (and other oxide as well as other suitable ceramic) small wires (particularly those described herein) or porous bodies or porous membranes as substrates for catalysts utilized for the photodegradation of toxic organic pollutants. Benefiting from the high surface area, good dispersion, and chemical stability of these oxide small wires, the catalysts (e.g., $TiO_2$, ZnO, $Bi_2O_3$, $BiVO_4$, etc.) may exhibit high and stable photocatalytic activity for the degradation and mineralization of various toxic organic pollutants. Good mechanical stability, thermal stability, high porosity, and high permeability of the small oxide wires-based porous substrates (e.g., membranes) make them particularly attractive for such applications.

In some applications, some or all of the pores in the porous ceramic (e.g., oxide) small wires may be infiltrated with functional fillers for improved performance in various applications. Examples of useful functional fillers may include: (i) magnetic (e.g., ferrimagentic materials, ferromagnetic materials, etc.) materials, (ii) superconductive materials, (iii) piezoelectric materials, (iv) ferroelectric materials (including pyroelectric materials), (v) various other markers or sensing materials (detectors), (vi) various optical materials, (vii) strong dielectrics, and others. Magnetic fillers may be used to orient the small wires along the desired direction by application of a magnetic field (which may be advantageous, e.g., in making improved composites or during the operation of the materials or devices, or both). Magnetic fillers may make it easier to assemble cells with ceramic small wire-based separators. Porous wires filled with magnetic materials and thus attaining magnetic properties may be used as soft or hard magnets (depending on the filler) and be used in corresponding applications (e.g., transformers, inductors, electric machines, electromagnet cores, relays, magnetic recording heads, magnetic amplifiers, filters, etc., for soft magnets or magnetic recording (storage) media, permanent magnets (e.g., integrated in multifunctional materials), loudspeakers and headphones, phone receivers, starter motors, servo motors, stepper and other motors, MRI scanners, etc. for hard magnets). Superconductive materials (e.g., filled within interconnected pores of the, e.g., small oxide wires or other ceramic wires or metal organic wires or metallic wires) may allow these to attain superconductive properties (e.g., below a critical temperature or below a critical magnetic field) and used in functional (or multifunctional) devices. Confinement of the superconductive materials within the (nano)pores of the small wires may provide additional performance (or stability) advantages and improve the mechanical (or other) properties of the superconductors. The produced filled porous wire composites may be parts of other materials or devices. Piezoelectric fillers may make the wires attain piezoelectric properties. Porous wires filled with piezoelectric materials and thus attaining piezoelectric properties may also be used, e.g., in piezoelectric transducers, crystal oscillators, delay lines, filters, accelerometers, earphones, speakers, microphones, and spark generators, to name a few. The confinement of the piezoelectric materials into the pores (e.g., interconnected pores) of the wires may enhance their performance or stability, or allow formation of 1D (wire-shaped) piezoelectric materials or 2D (membrane-shaped) ferroelectric materials, or may allow attaining multifunctional properties. Ferroelectric fillers may make the wires attain ferroelectric properties. These properties may help to orient the wires along the desired direction(s) by applying an electric field (which may be advantageous, e.g., in making improved composites or during the operation of the materials or devices, or both). Porous wires filled with ferroelectric materials and thus attaining ferroelectric properties may also be used, e.g., in electronic circuits, electro-optic modulators, high-k-dielectrics, capacitors (e.g., with tunable or non-tunable capacitance), ferroelectric random access memory, ferroelectric tunnel junction devices, sensors, multiferroics, fire (or heat) sensors, sonar, vibration sensors, fuel injectors, etc. Pyroelectric fillers is a sub-class of the ferroelectric fillers, in which the dipole moment depends on temperature. These are particularly useful as radiation or heat detectors. The confinement of the ferroelectric materials into the pores (e.g., interconnected pores) of the small porous wires may enhance their performance or stability, or allow formation of 1D (wire-shaped) ferroelectric materials or 2D (membrane-shaped) ferroelectric materials, or may allow attaining multifunctional properties.

In some designs, it may be advantageous for the small oxide wires (including the small wires produced according to the disclosed methods) to be processed into thermally stable (e.g., to above 1200° C.) and ultra-strong yards, ropes, sheets, and fabrics (e.g., based on $Al_2O_3$, $ZrO_2$, or MgO small wires).

The foregoing description is provided to enable any person skilled in the art to make or use embodiments of the present invention. It will be appreciated, however, that the present invention is not limited to the particular formulations, process steps, and materials disclosed herein, as various modifications to these embodiments will be readily apparent to those skilled in the art. That is, the generic principles defined herein may be applied to other embodiments without departing from the spirit or scope of the invention.

The invention claimed is:

1. A catalyst-free synthesis method for the formation of a metalorganic compound comprising a first metal, the method comprising:
    selecting a second metal and an organic solvent, wherein the second metal is selected to (i) be more reactive with respect to the organic solvent than the first metal and (ii) form, upon exposure of the second metal to the organic solvent, a reaction by-product comprising the second metal that is more soluble in the organic solvent than the metalorganic compound comprising the first metal;
    producing an alloy comprising the first metal and the second metal;
    treating the alloy with the organic solvent in a liquid phase or a vapor phase to form a mixture comprising (i) the reaction by-product comprising the second metal and (ii) the metalorganic compound comprising the first metal; and
    separating the metalorganic compound from the mixture in the form of a solid.

2. The method of claim 1, wherein the second metal has a reactivity with respect to the organic solvent that is at least five times higher than that of the first metal.

3. The method of claim 1, wherein:
    the organic solvent is in the form of a liquid; and
    the treating is performed at a temperature in the range of about −20° C. to about +200° C.

4. The method of claim 1, wherein the first metal is selected from the group consisting of Ti, Cr, Fe, Co, Ni, Cu, Zr, Nb, Mo, Ru, Rh, Pd, Ag, Ta, W, Re, Os, Ir, Pt, Al, Zn, Cd, In, Sn, Sb, Bi, P, La, Ce, Ca, Mg, Sr, and Be.

5. The method of claim 4, wherein the second metal is selected from the group consisting of Li, K, Ca, and Na.

6. The method of claim 1, wherein the metalorganic compound comprises porous particles.

7. The method of claim 1, wherein the metalorganic compound comprises elongated particles.

8. The method of claim 7, wherein the elongated particles exhibit a width in the range of about 2 nm to about 10 microns, a length in the range of about 50 nm to about 50 mm, and a corresponding width-to-length aspect ratio in the range of about 1:4 to about 1:10,000,000.

9. The method of claim 7, wherein the metalorganic compound is an alkoxide.

10. The method of claim 1, further comprising converting the metalorganic compound to a metal oxide compound in the form of elongated particles.

11. The method of claim 10, wherein the elongated metal oxide particles are porous.

12. The method of claim 10, wherein the converting is performed at a temperature in the range of about −20° C. to about +1500° C. in an oxygen-containing environment.

13. The method of claim 10, further comprising depositing a coating layer on a surface of the elongated metal oxide particles or a precursor thereof.

14. The method of claim 13, wherein the coating layer is a metal, a polymer, or a ceramic material.

15. The method of claim 13, wherein the coating layer is deposited via chemical vapor deposition or atomic vapor deposition.

16. The method of claim 1, further comprising:
    forming elongated particles of the metalorganic compound into a membrane or body; and
    converting the elongated metalorganic compound particles into elongated metal oxide compound particles to form a porous oxide membrane or body.

17. The method of claim 16, wherein the converting partially bonds at least some of the elongated metal oxide compound particles to each other.

18. The method of claim 16, further comprising infiltrating the porous oxide membrane or body with a filler material.

19. The method of claim 18, wherein the filler material is a metal.

20. The method of claim 18, wherein the filler material is a glass.

21. The method of claim 18, wherein the filler material is a polymer.

22. The method of claim 16, further comprising integrating the porous oxide membrane or body into an electrochemical energy storage device as a separator.

23. The method of claim 22, further comprising depositing a polymer layer onto the surface of the porous oxide membrane or body.

24. The method of claim 23, wherein the polymer layer closes the pores of the porous oxide membrane or body to prevent ion transport at temperatures above a threshold temperature in the range of about 70° C. to about 130° C.